(12) United States Patent
Gilmore et al.

(10) Patent No.: US 11,337,686 B2
(45) Date of Patent: *May 24, 2022

(54) OFF-CENTER TISSUE ANCHORS

(71) Applicant: 4Tech Inc., Waltham, MA (US)

(72) Inventors: Michael Gilmore, County Galway (IE);
Paolo Denti, Opera (IT); John Mullins, County Galway (IE); Charlotte Murphy, County Galway (IE); Kevin Lynn, County Galway (IE); Andrea Guidotti, Zurich (CH); Hugo Vanermen, Knocke-le-Zoute (BE); Thomas Campbell, County Mayo (IE)

(73) Assignee: 4Tech Inc., Clayton, DE (US)

( * ) Notice: Subject to any disclaimer, the term of this patent is extended or adjusted under 35 U.S.C. 154(b) by 273 days.

This patent is subject to a terminal disclaimer.

(21) Appl. No.: 16/724,796

(22) Filed: Dec. 23, 2019

(65) Prior Publication Data

US 2020/0121312 A1 Apr. 23, 2020

Related U.S. Application Data

(63) Continuation of application No. 16/573,328, filed on Sep. 17, 2019, now Pat. No. 10,588,618, which is a
(Continued)

(51) Int. Cl.
*A61B 17/04* (2006.01)
*A61F 2/24* (2006.01)
(Continued)

(52) U.S. Cl.
CPC ...... *A61B 17/0401* (2013.01); *A61B 17/0057* (2013.01); *A61B 17/00234* (2013.01);
(Continued)

(58) Field of Classification Search
CPC ..... A61F 2/2442; A61F 2/2478; A61F 2/2481
See application file for complete search history.

(56) References Cited

U.S. PATENT DOCUMENTS

| 3,874,388 A | 4/1975 | King et al. |
| 4,007,743 A | 2/1977 | Blake |

(Continued)

FOREIGN PATENT DOCUMENTS

| WO | 1997041778 A1 | 11/1997 |
| WO | 2001010306 A1 | 2/2001 |

(Continued)

OTHER PUBLICATIONS

JPO, Office Action issued in Japanese Patent Application Serial No. 525540/2017, dated Oct. 15, 2019 (English translation).
(Continued)

*Primary Examiner* — Ryan J. Severson
(74) *Attorney, Agent, or Firm* — UltimatEdge IP Law Group, P.C.; Dean G. Stathakis; Vito A. Canuso, III

(57) ABSTRACT

A method is provided including introducing, during a transcatheter procedure, a tissue anchor into a cardiac chamber of a heart of a subject, while a tissue-coupling element of the tissue anchor is constrained by a deployment tool. The tissue-coupling element is delivered distally through a cardiac wall. The tissue anchor is at least partially released from the deployment tool such that the tissue-coupling element is unconstrained by the deployment tool. After the tissue-coupling element is delivered through the cardiac wall and the tissue anchor is at least partially released from the deployment tool, whether the tissue-coupling element overlies a coronary blood vessel is ascertained, and, if the tissue-coupling element overlies the coronary blood vessel, the tissue anchor is rotated until the tissue-coupling element no longer overlies the coronary blood vessel. Thereafter, the tissue-coupling element is proximally pulled by applying tension to the tissue anchor. Other embodiments are also described.

7 Claims, 44 Drawing Sheets

Related U.S. Application Data continuation of application No. 15/619,881, filed on Jun. 12, 2017, now Pat. No. 10,463,358, which is a continuation of application No. 15/104,467, filed as application No. PCT/IB2015/002354 on Dec. 2, 2015, now Pat. No. 9,907,547.

(60) Provisional application No. 62/167,660, filed on May 28, 2015, provisional application No. 62/086,269, filed on Dec. 2, 2014.

(51) Int. Cl.
| | |
|---|---|
| A61B 17/068 | (2006.01) |
| A61B 17/10 | (2006.01) |
| A61F 2/82 | (2013.01) |
| A61B 17/00 | (2006.01) |
| A61F 2/915 | (2013.01) |
| A61B 17/064 | (2006.01) |

(52) U.S. Cl.
CPC ............ *A61B 17/068* (2013.01); *A61B 17/10* (2013.01); *A61F 2/2442* (2013.01); *A61F 2/2478* (2013.01); *A61F 2/82* (2013.01); *A61F 2/915* (2013.01); A61B 2017/00243 (2013.01); A61B 2017/00309 (2013.01); A61B 2017/00477 (2013.01); A61B 2017/00575 (2013.01); A61B 2017/00592 (2013.01); A61B 2017/00615 (2013.01); A61B 2017/00632 (2013.01); A61B 2017/0409 (2013.01); A61B 2017/0417 (2013.01); A61B 2017/0419 (2013.01); A61B 2017/0443 (2013.01); A61B 2017/0464 (2013.01); A61B 2017/0645 (2013.01); A61B 2017/0649 (2013.01); A61F 2230/0091 (2013.01)

(56) References Cited

U.S. PATENT DOCUMENTS

| | | | |
|---|---|---|---|
| 5,730,127 | A | 3/1998 | Avitall |
| 5,755,760 | A | 5/1998 | Maguire et al. |
| 5,823,955 | A | 10/1998 | Kuck et al. |
| 6,010,113 | A | 1/2000 | Rotering |
| 6,214,002 | B1 | 4/2001 | Fleischman et al. |
| 6,260,552 | B1 | 7/2001 | Mortier et al. |
| 6,572,612 | B2 | 6/2003 | Stewart et al. |
| 6,602,288 | B1 | 8/2003 | Cosgrove et al. |
| 6,616,684 | B1 | 9/2003 | Vidlund et al. |
| 6,629,534 | B1 | 10/2003 | St. Goar et al. |
| 6,635,068 | B1 | 10/2003 | Dubrul et al. |
| 6,743,198 | B1 | 6/2004 | Tihon |
| 6,746,472 | B2 | 6/2004 | Frazier et al. |
| 6,752,813 | B2 | 6/2004 | Goldfarb et al. |
| 6,926,714 | B1 | 8/2005 | Sra |
| 7,056,333 | B2 | 6/2006 | Walshe |
| 7,077,861 | B2 | 7/2006 | Spence |
| 7,166,127 | B2 | 1/2007 | Spence et al. |
| 7,311,705 | B2 | 12/2007 | Sra |
| 7,435,248 | B2 | 10/2008 | Taimisto et al. |
| 7,597,703 | B2 | 10/2009 | Sater |
| 7,618,449 | B2 | 11/2009 | Tremulis et al. |
| 7,850,685 | B2 | 12/2010 | Kunis et al. |
| 7,892,214 | B2 | 2/2011 | Kagan et al. |
| 7,992,567 | B2 | 8/2011 | Hirotsuka et al. |
| 8,025,495 | B2 | 9/2011 | Hardert et al. |
| 8,029,518 | B2 | 10/2011 | Goldfarb et al. |
| 8,105,352 | B2 | 1/2012 | Egnelöv et al. |
| 8,142,493 | B2 | 3/2012 | Spence et al. |
| 8,172,898 | B2 | 5/2012 | Alferness et al. |
| 8,186,355 | B2 | 5/2012 | Van Der Burg et al. |
| 8,197,441 | B2 | 6/2012 | Webler et al. |
| 8,295,902 | B2 | 10/2012 | Salahieh et al. |
| 8,398,672 | B2 | 3/2013 | Kleshinski et al. |
| 8,425,402 | B2 | 4/2013 | Annest et al. |
| 8,491,455 | B2 | 7/2013 | Annest et al. |
| 8,523,881 | B2 | 9/2013 | Cabiri et al. |
| 8,568,445 | B2 | 10/2013 | Pipenhagen et al. |
| 8,641,704 | B2 | 2/2014 | Werneth et al. |
| 8,777,904 | B2 | 7/2014 | Kassab et al. |
| 9,301,740 | B2 | 4/2016 | Thielen et al. |
| 9,480,559 | B2 | 11/2016 | Vidlund et al. |
| 9,629,619 | B2 | 4/2017 | Tenerz |
| 9,907,547 | B2 | 3/2018 | Gilmore et al. |
| 9,999,713 | B2 | 6/2018 | Solem |
| 10,441,267 | B2 | 10/2019 | Gilmore et al. |
| 10,463,358 | B2 | 11/2019 | Gilmore et al. |
| 2002/0013571 | A1 | 1/2002 | Goldfarb et al. |
| 2003/0069570 | A1 | 4/2003 | Witzel et al. |
| 2003/0078465 | A1 | 4/2003 | Pai et al. |
| 2003/0144732 | A1 | 7/2003 | Cosgrove et al. |
| 2003/0233142 | A1 | 12/2003 | Morales et al. |
| 2004/0186566 | A1 | 9/2004 | Hindrichs et al. |
| 2004/0260317 | A1 | 12/2004 | Bloom et al. |
| 2005/0096666 | A1 | 5/2005 | Gordon et al. |
| 2005/0143770 | A1 | 6/2005 | Carter et al. |
| 2005/0251208 | A1 | 11/2005 | Elmer et al. |
| 2006/0142797 | A1 | 6/2006 | Egnelov |
| 2006/0276871 | A1 | 12/2006 | Lamson et al. |
| 2007/0027533 | A1 | 2/2007 | Douk |
| 2007/0066863 | A1 | 3/2007 | Rafiee et al. |
| 2007/0067027 | A1 | 3/2007 | Moaddeb et al. |
| 2007/0118151 | A1 | 5/2007 | Davidson |
| 2007/0123936 | A1 | 5/2007 | Goldin et al. |
| 2007/0144539 | A1 | 6/2007 | Van Der Burg et al. |
| 2007/0185532 | A1 | 8/2007 | Stone et al. |
| 2007/0185572 | A1 | 8/2007 | Solem et al. |
| 2007/0233239 | A1 | 10/2007 | Navia et al. |
| 2007/0244554 | A1 | 10/2007 | Rafiee et al. |
| 2007/0244556 | A1 | 10/2007 | Rafiee et al. |
| 2008/0027446 | A1 | 1/2008 | Stone et al. |
| 2008/0058866 | A1 | 3/2008 | Young et al. |
| 2008/0167714 | A1 | 7/2008 | St. Goar et al. |
| 2008/0228267 | A1 | 9/2008 | Spence et al. |
| 2009/0054926 | A1 | 2/2009 | Pipenhagen et al. |
| 2009/0093670 | A1 | 4/2009 | Annest et al. |
| 2009/0112052 | A1 | 4/2009 | Lund et al. |
| 2010/0217309 | A1 | 8/2010 | Hansen et al. |
| 2010/0217312 | A1 | 8/2010 | Hill et al. |
| 2011/0029071 | A1 | 2/2011 | Zlotnick et al. |
| 2011/0098727 | A1 | 4/2011 | Kaiser et al. |
| 2011/0106245 | A1 | 5/2011 | Miller et al. |
| 2011/0184510 | A1 | 7/2011 | Maisano et al. |
| 2011/0319989 | A1 | 12/2011 | Lane et al. |
| 2012/0035712 | A1 | 2/2012 | Maisano et al. |
| 2012/0101525 | A1 | 4/2012 | Jenson et al. |
| 2012/0123531 | A1 | 5/2012 | Tsukashima et al. |
| 2012/0158053 | A1 | 6/2012 | Paulos |
| 2012/0172928 | A1 | 7/2012 | Eidenschink et al. |
| 2012/0179086 | A1 | 7/2012 | Shank et al. |
| 2013/0018459 | A1 | 1/2013 | Maisano et al. |
| 2013/0030522 | A1 | 1/2013 | Rowe et al. |
| 2013/0060279 | A1 | 3/2013 | Yassinzadeh |
| 2013/0253640 | A1 | 9/2013 | Meiri et al. |
| 2013/0296925 | A1 | 11/2013 | Chanduszko et al. |
| 2013/0325115 | A1 | 12/2013 | Maisano et al. |
| 2014/0114390 | A1 | 4/2014 | Tobis et al. |
| 2014/0163608 | A1 | 6/2014 | Osypka |
| 2014/0214159 | A1 | 7/2014 | Vidlund et al. |
| 2014/0275756 | A1 | 9/2014 | Bender et al. |
| 2014/0275865 | A1 | 9/2014 | Tammam et al. |
| 2015/0018876 | A1 | 1/2015 | Ewers et al. |
| 2015/0025553 | A1 | 1/2015 | Del Nido et al. |
| 2015/0119936 | A1 | 4/2015 | Gilmore et al. |
| 2015/0157329 | A1 | 6/2015 | Rudakov et al. |
| 2016/0262741 | A1 | 9/2016 | Gilmore et al. |
| 2017/0209137 | A1 | 7/2017 | Gilmore et al. |
| 2017/0273681 | A1 | 9/2017 | Gilmore et al. |

(56) References Cited

U.S. PATENT DOCUMENTS

| | | | |
|---|---|---|---|
| 2019/0069891 A1 | 3/2019 | Gilmore et al. | |
| 2019/0083085 A1 | 3/2019 | Gilmore et al. | |

FOREIGN PATENT DOCUMENTS

| | | | |
|---|---|---|---|
| WO | 2004069055 A2 | 8/2004 | |
| WO | 2009081396 A2 | 7/2009 | |
| WO | 2011089601 A1 | 7/2011 | |
| WO | 2013003228 A1 | 1/2013 | |
| WO | 2014108903 A1 | 7/2014 | |
| WO | 2014141239 A1 | 9/2014 | |
| WO | 2015015497 A1 | 2/2015 | |
| WO | 2015063580 A2 | 5/2015 | |
| WO | 2015193728 A2 | 12/2015 | |
| WO | 2016087934 A1 | 6/2016 | |
| WO | 2016189391 A2 | 12/2016 | |
| WO | 2017059426 A1 | 4/2017 | |
| WO | 2017066257 A1 | 4/2017 | |
| WO | 2018035378 A1 | 2/2018 | |

OTHER PUBLICATIONS

An Office Action dated Sep. 19, 2019, which issued during the prosecution of U.S. Appl. No. 15/165,768.

Invitation to pay additional fees in PCT/IB2016/000840 dated Oct. 13, 2016.

An International Search Report and a Written Opinion both dated Dec. 8, 2016, which issued during the prosecution of Applicant's PCT/IB2016/000840.

An International Search Report and a Written Opinion both dated Sep. 18, 2018, which issued during the prosecution of Applicant's PCT/US18/036609.

An International Search Report and a Written Opinion both dated Oct. 15, 2018, which issued during the prosecution of Applicant's PCT/US18/040147.

Written Opinion of the International Preliminary Examining Authority dated May 14, 2019, which issued during the prosecution of Applicant's PCT/US18/036609.

An Office Action summarized English translation and Search Report dated Apr. 2, 2019 which issued during the prosecution of Chinese Patent Application No. 2016800303355.

An Office Action summarized English translation and Search Report dated May 29, 2019 which issued during the prosecution of Chinese Patent Application No. 201580065246X.

U.S. Appl. No. 62/086,269, filed Dec. 2, 2014.

U.S. Appl. No. 62/167,660, filed May 28, 2015.

U.S. Appl. No. 62/516,894, filed Jun. 8, 2017.

An Office Action dated Sep. 26, 2017, which issued during the prosecution of U.S. Appl. No. 15/104,467.

Notice of Allowance dated Jan. 11, 2018, which issued during the prosecution of U.S. Appl. No. 15/104,467.

An Office Action dated Apr. 2, 2018, which issued during the prosecution of U.S. Appl. No. 15/165,768.

An Office Action dated Apr. 18, 2019, which issued during the prosecution of U.S. Appl. No. 15/619,881.

A communication from the European Patent Office dated Nov. 27, 2018, which issued during the prosecution of European Application No. 17191569.7.

European Search Report dated Dec. 5, 2018, which issued during the prosecution of Applicant's European App No. 16734021.5.

Extended European Search Report dated Jan. 23, 2018, which issued during the prosecution of Applicant's European App No. 17191569.7.

Mar. 2013 Mahajan AK et al., "Isolation of persistent air leaks and placement of intrabronchial valves," Mar. 2013 J Thorac Cardiovasc Surg 145(3):626-30.

An International Search Report and a Written Opinion both dated Apr. 15, 2016, 2014, which issued during the prosecution of Applicant's PCT/IB2015/002354.

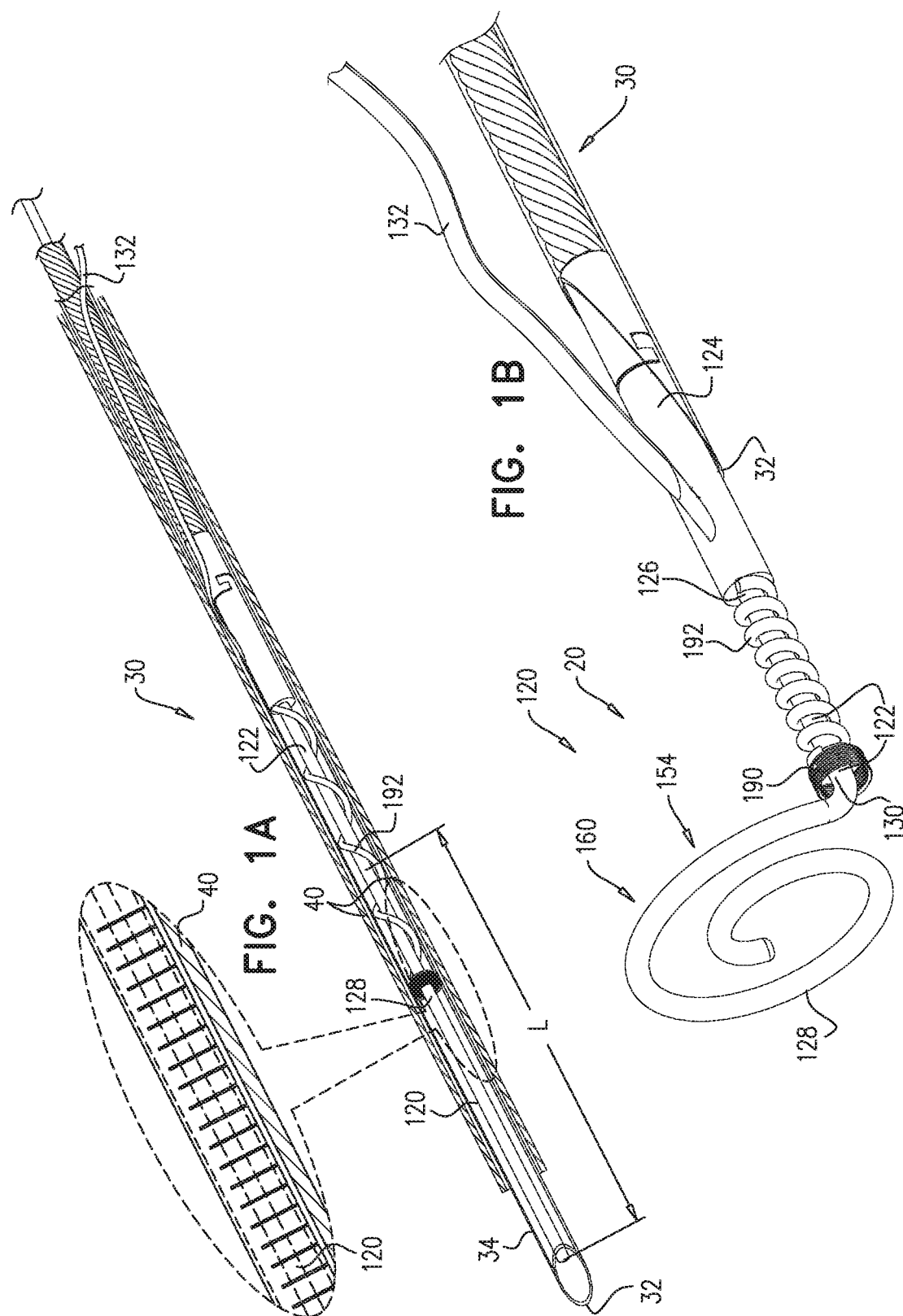

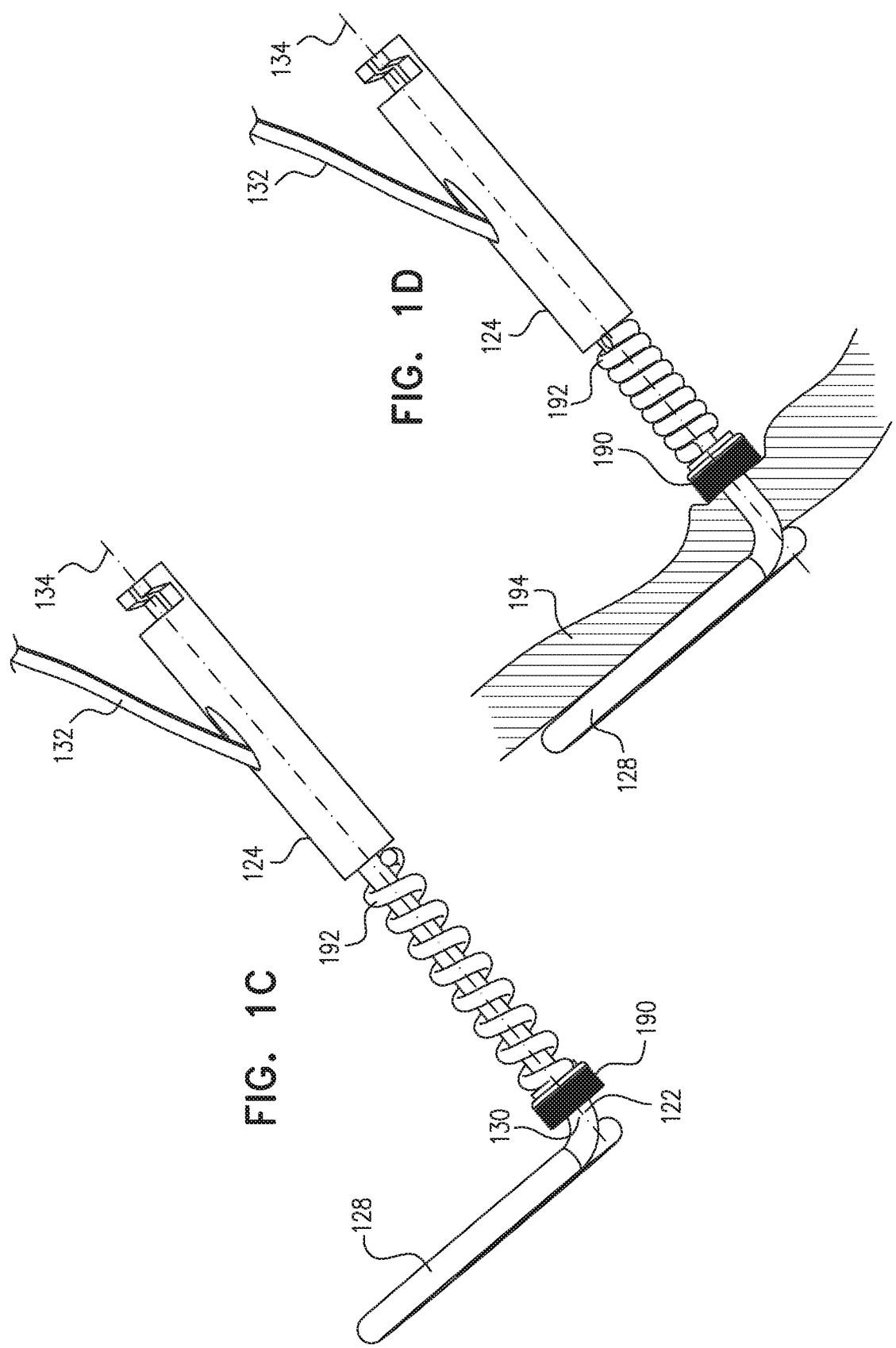

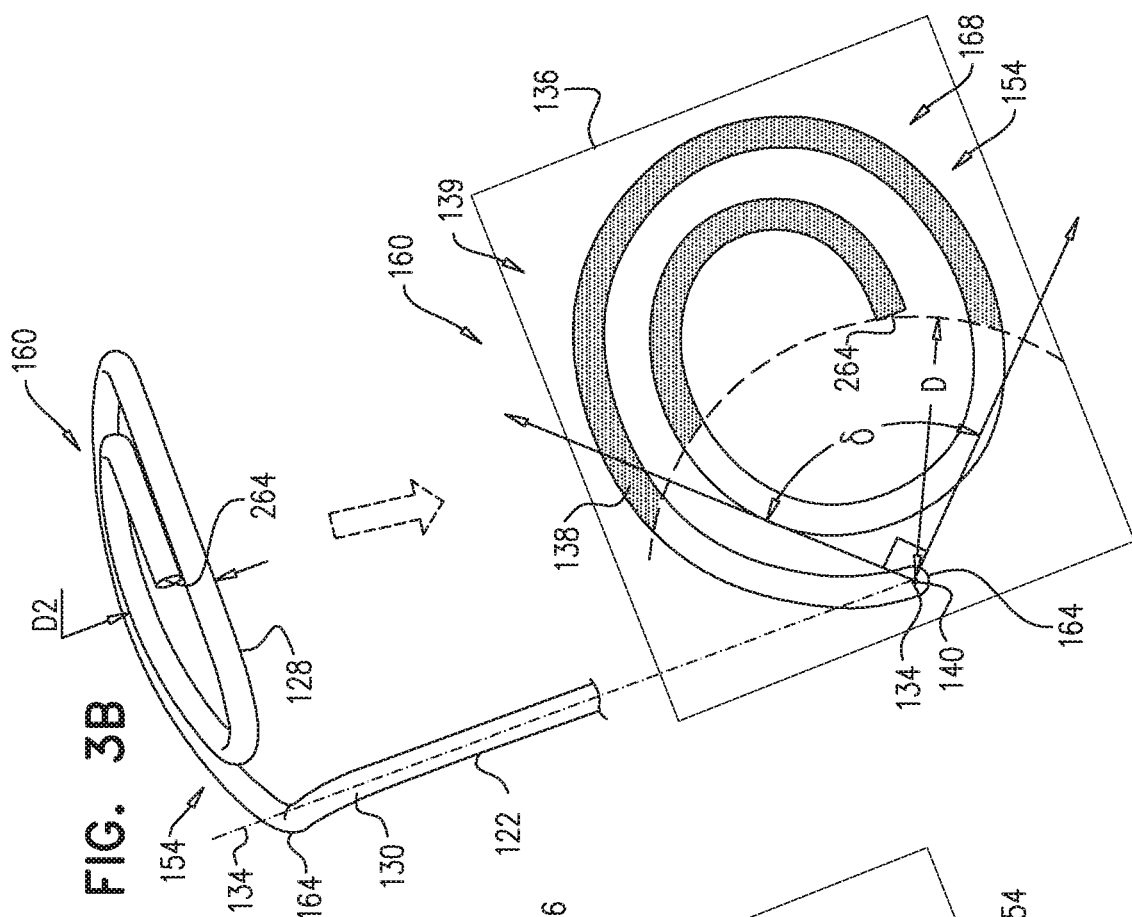
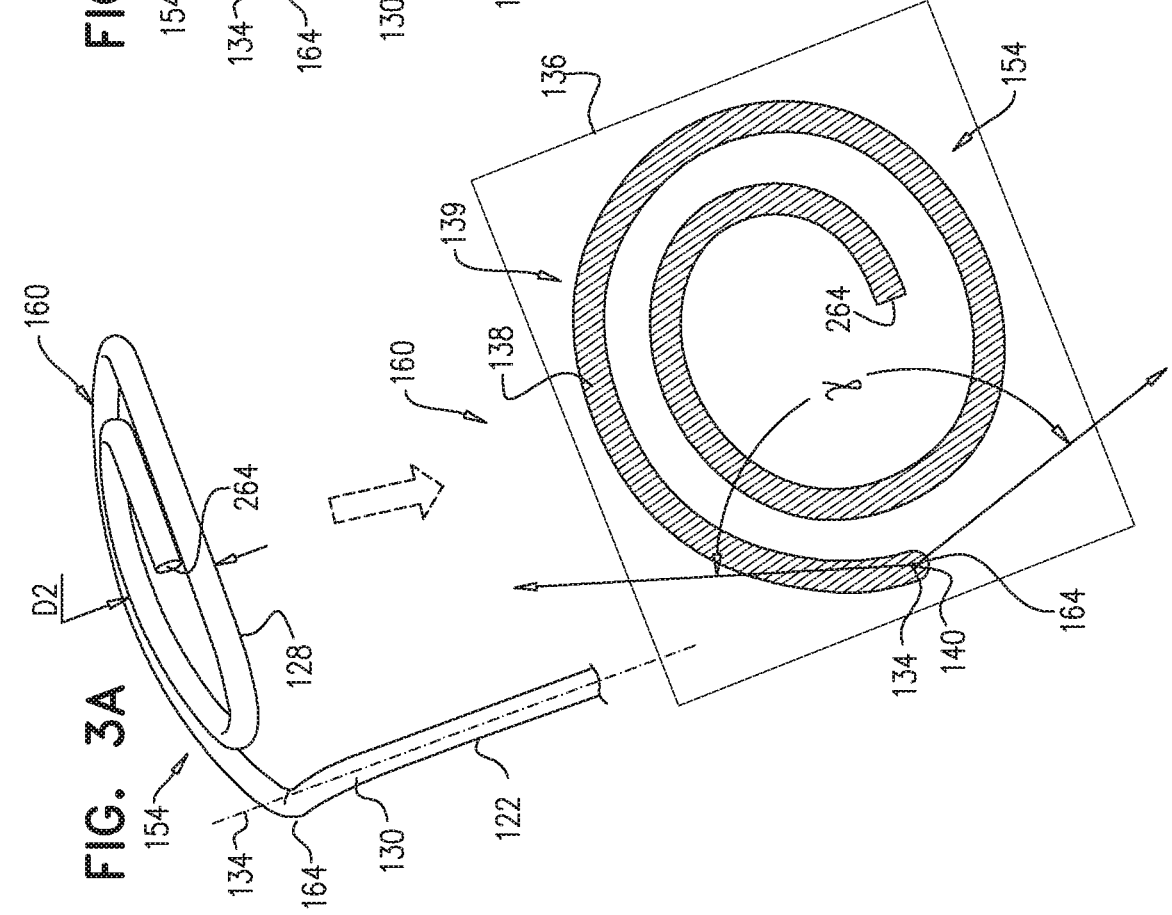
FIG. 3A
FIG. 3B

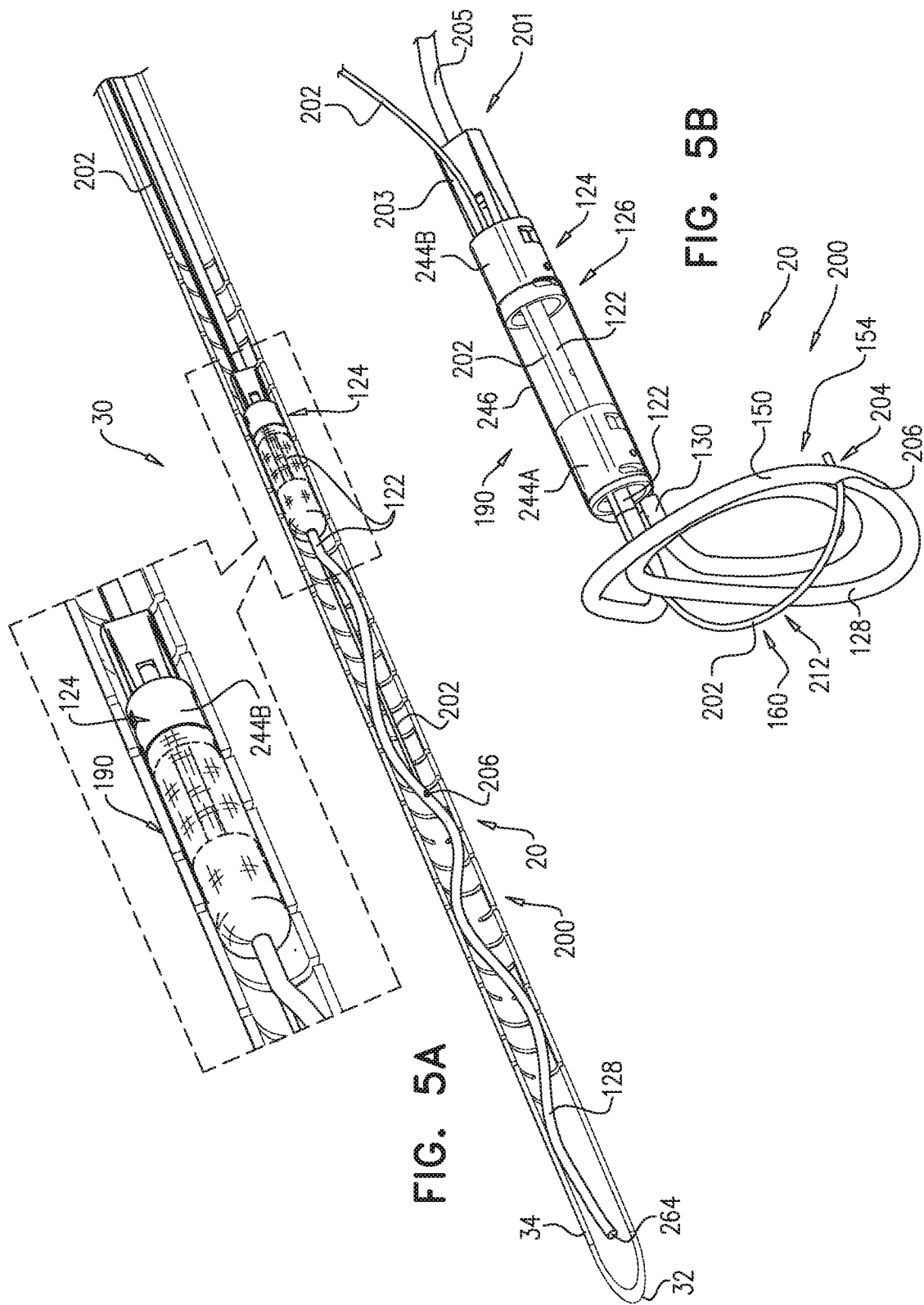

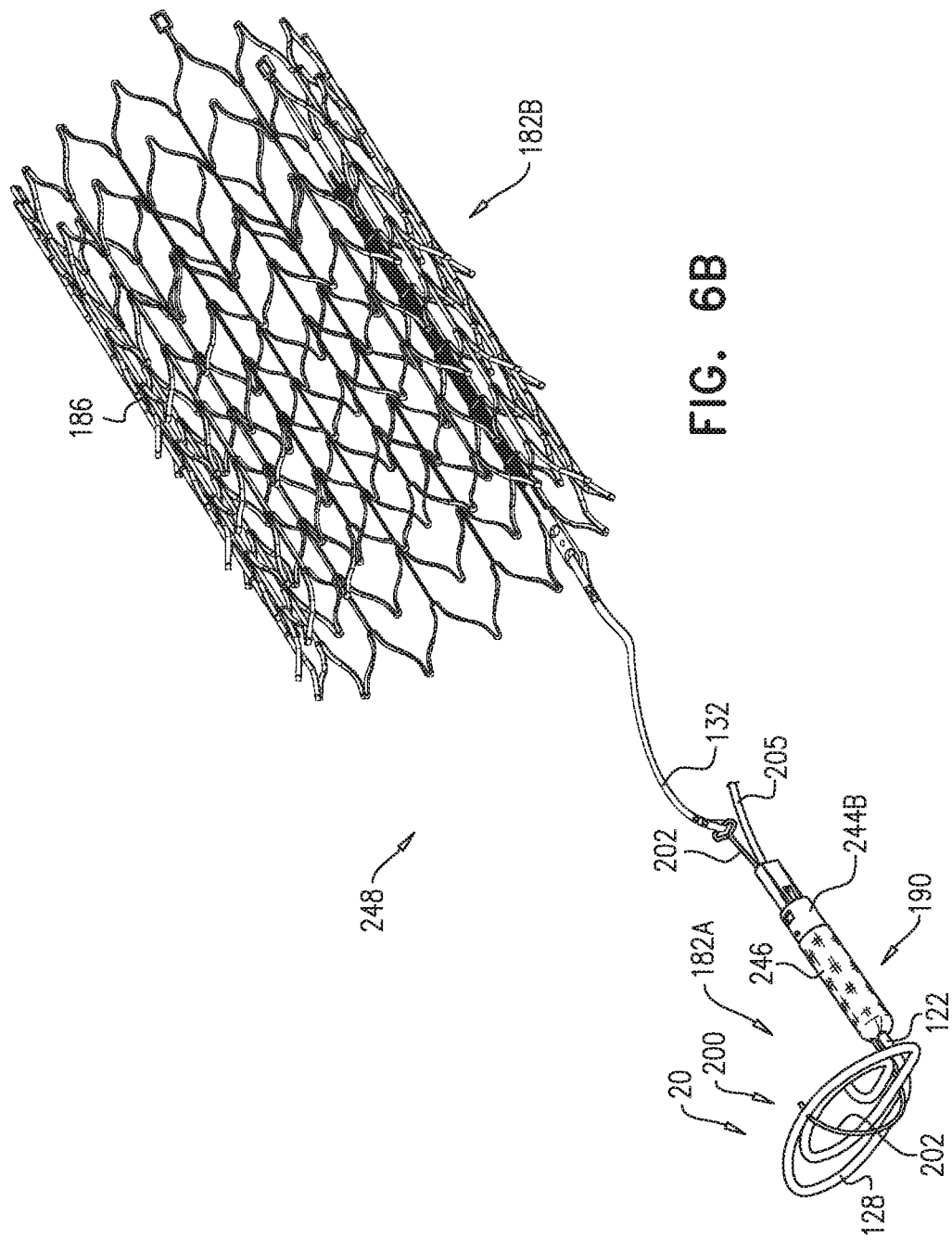

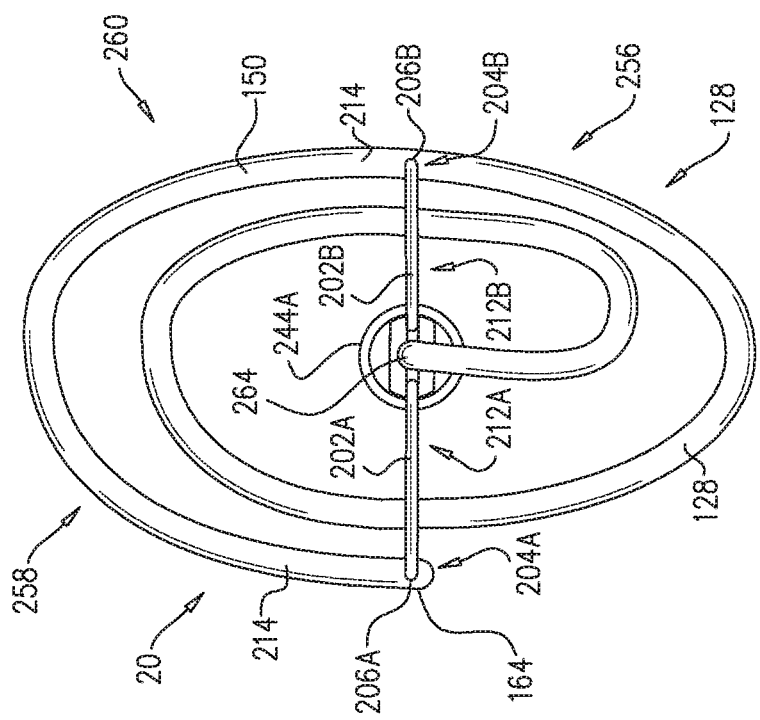
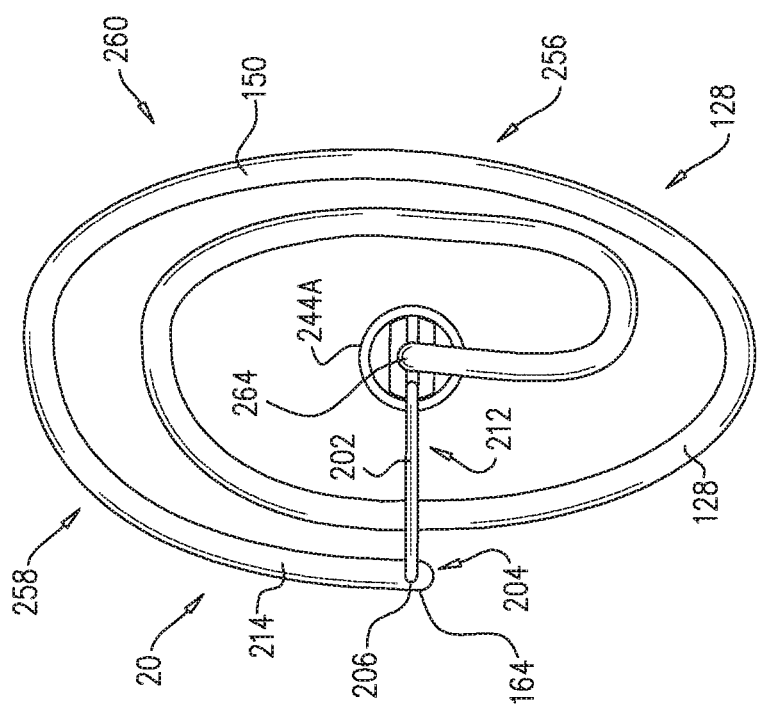

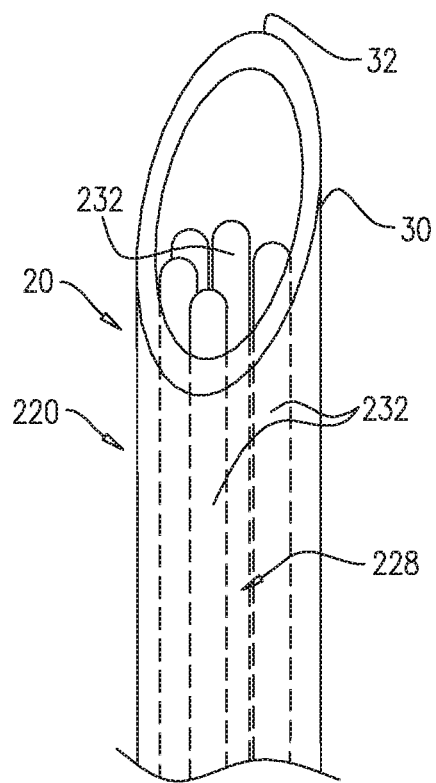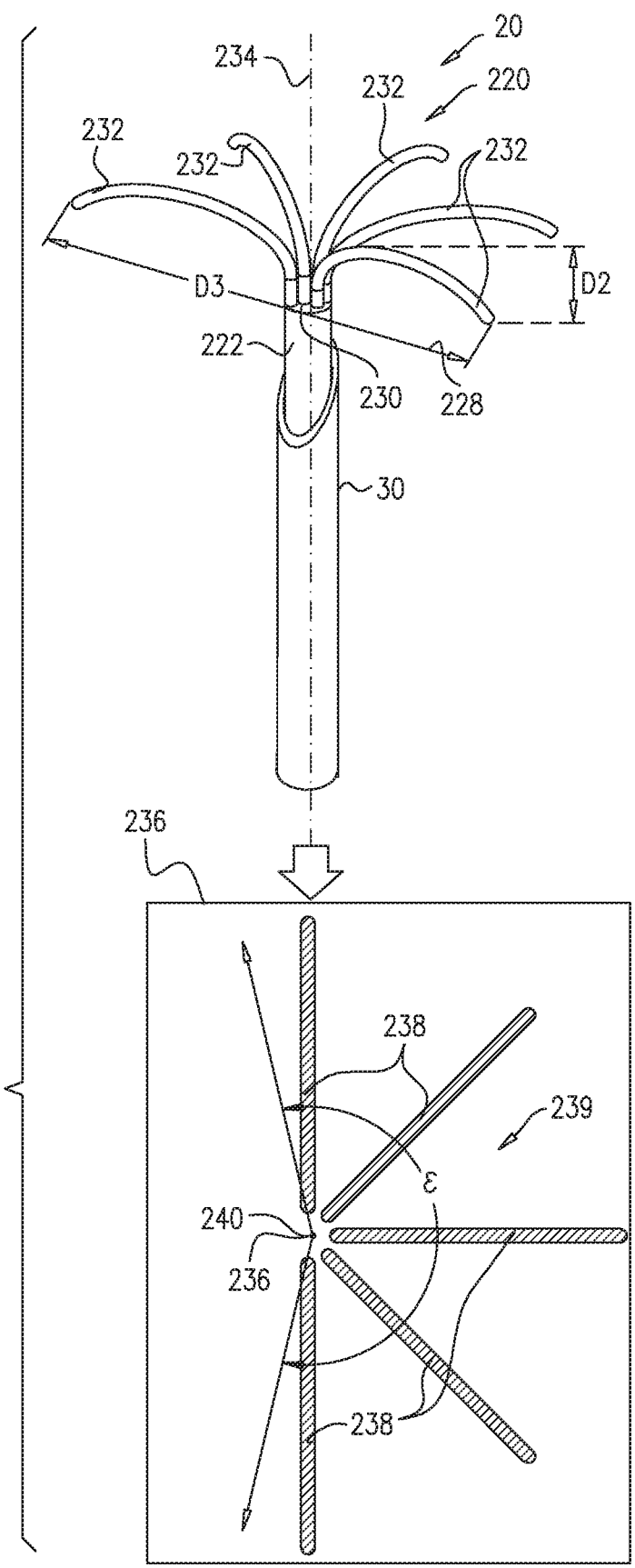

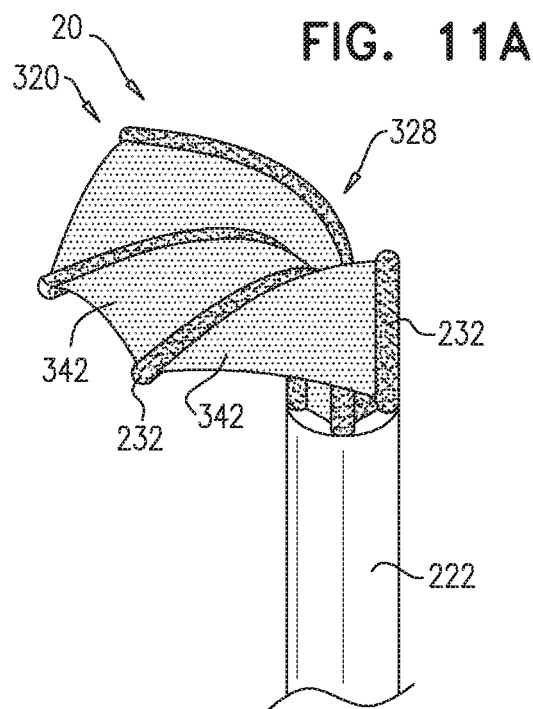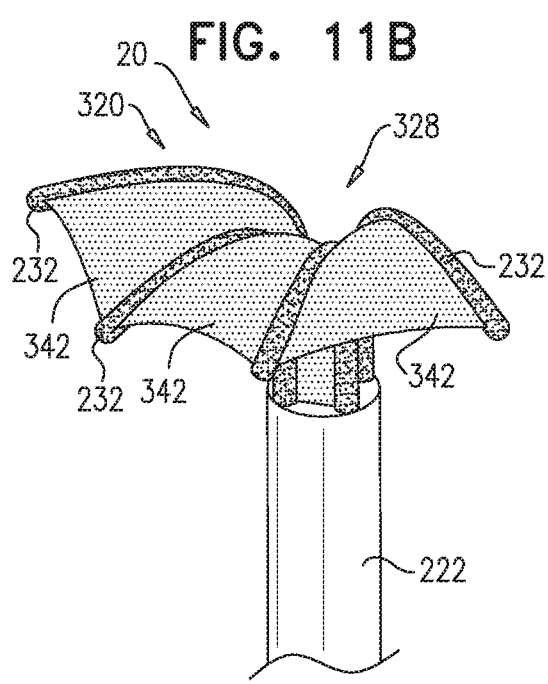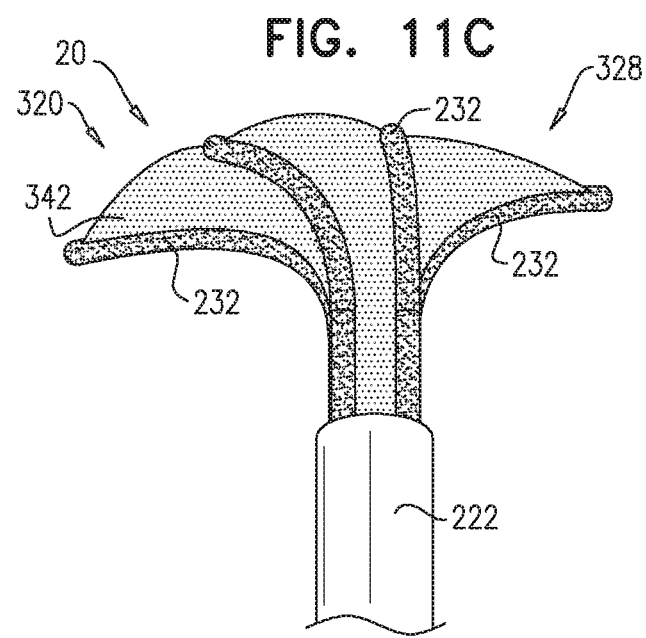

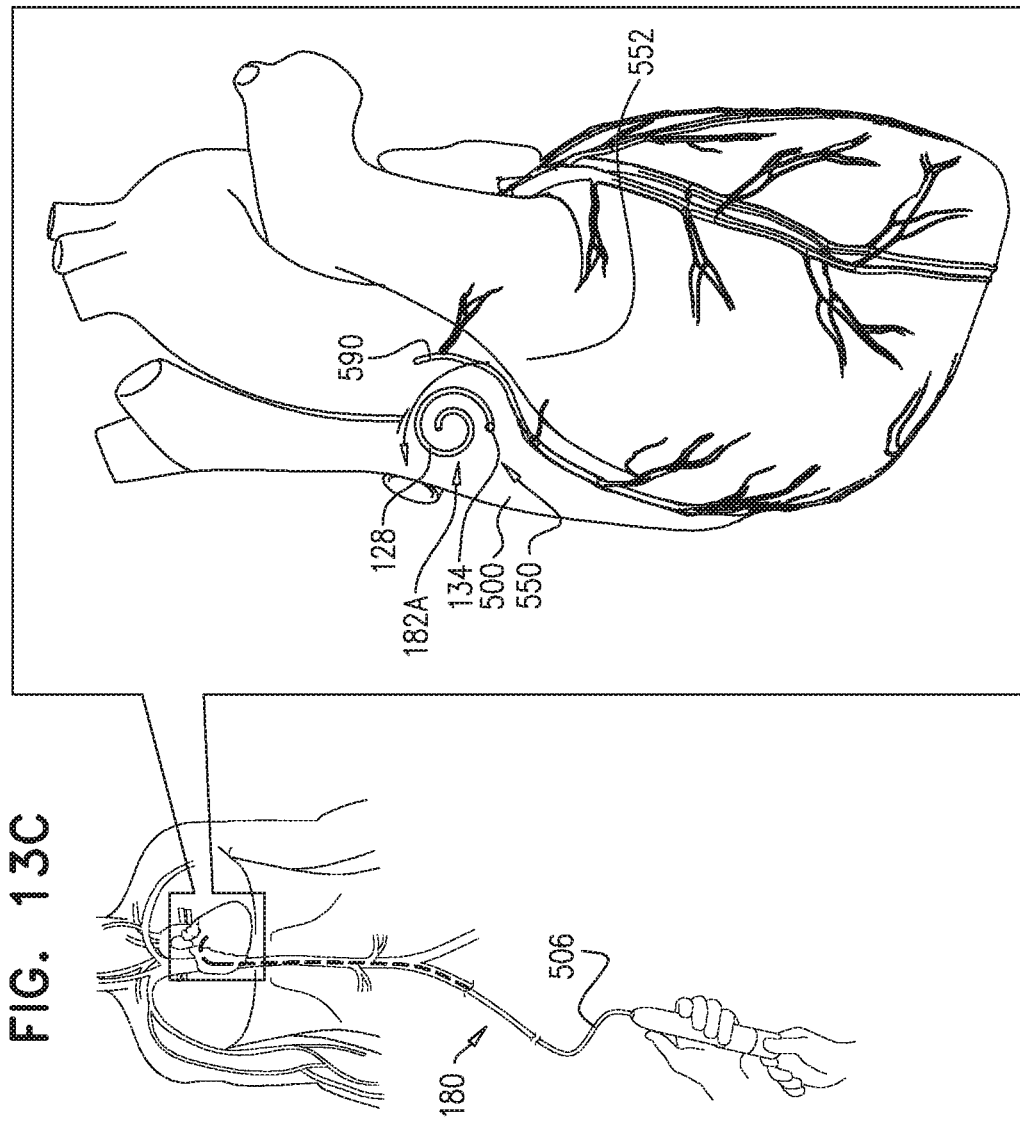

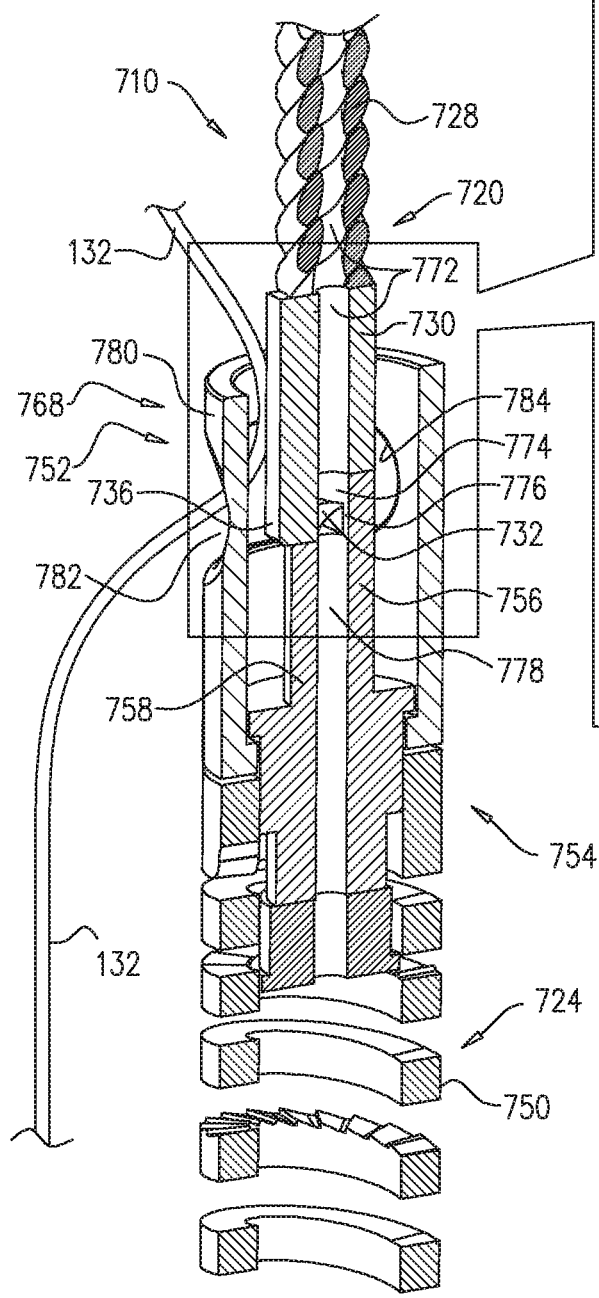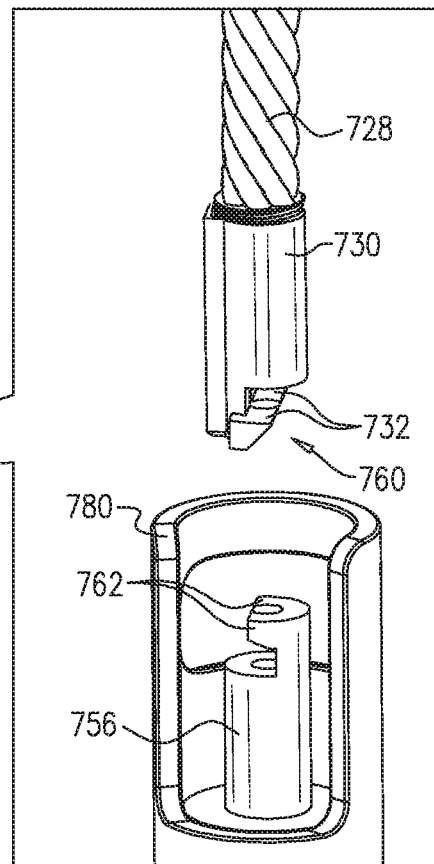
FIG. 17F

OFF-CENTER TISSUE ANCHORS

CROSS-REFERENCE TO RELATED APPLICATIONS

The present application is a continuation of U.S. application Ser. No. 16/573,328, filed Sep. 17, 2019, which is a continuation of U.S. application Ser. No. 15/619,881, filed Jun. 12, 2017, now U.S. Pat. No. 10,463,358, which is a continuation of U.S. application Ser. No. 15/104,467, filed Jun. 14, 2016, now U.S. Pat. No. 9,907,547, which is the U.S. national stage of International Application PCT/IB2015/002354, filed Dec. 2, 2015, which claims priority from (a) U.S. Provisional Application 62/086,269, filed Dec. 2, 2014, and (b) U.S. Provisional Application 62/167,660, filed May 28, 2015, which are assigned to the assignee of the present application and are incorporated herein by reference.

FIELD OF THE APPLICATION

The present invention relates generally to tissue anchors, and specifically to tissue anchors for implantation in soft tissue, such as cardiac tissue.

BACKGROUND OF THE APPLICATION

Tissue anchors are used for anchoring elements, such as electrode leads or sutures, to tissue, such as bone or soft tissue.

SUMMARY OF THE APPLICATION

Some embodiments of the present invention provide a tissue anchor that comprises (a) a shaft, (b) a head connected to a proximal portion of the shaft, and (c) a tissue-coupling element, which extends from a distal end of the shaft. The tissue-coupling element is off-center with respect to a central longitudinal axis of the shaft. This off-centeredness allows the tissue-coupling element to be rotated during implantation so as to avoid contact with a sensitive anatomic structure, such as a blood vessel.

For some applications, a deployment tool is provided for delivering the tissue anchor, while in a constrained state, through a wall of a heart of a subject, typically by advancing a sharp distal piercing tip of the deployment tool through the wall. A surgeon, after delivering the tissue-coupling element through the wall of the heart, ascertains whether the tissue-coupling element overlies a coronary blood vessel, such as the right coronary artery (RCA). If the tissue-coupling element overlies the coronary blood vessel, the surgeon rotates the tissue anchor until the tissue-coupling element no longer overlies the coronary blood vessel. The surgeon then brings the tissue-coupling element into contact with an external surface of the heart, by applying tension to the anchor head in the heart chamber.

The off-centeredness of the tissue-coupling element thus allows the surgeon to select an anchoring site from a plurality of anchoring sites around an exit site of the anchor on the heart wall, without the need to relocate the exit site by removing the tissue-coupling element and again penetrating the deployment tool through the heart wall to redeliver the tissue-coupling element. The off-centeredness of the tissue-coupling element allows for the biasing of the tissue-coupling element away from the exit site, by rotating the tissue-coupling element to find a point of minimal impact on the cardiac circulation.

Without the techniques of the present invention, the tissue-coupling element might inadvertently compress a blood vessel, which might result in cardiac complications including but not limited to angina, myocardial infarction, reduced blood flow, and/or a reduction in circulation efficiency in cardiac tissue. Removal of such an improperly positioned tissue-coupling element might be required, which might result in additional complications and injury to the patient.

For some applications, when the tissue anchor is unconstrained by the deployment tool, (a) the shaft has a central longitudinal axis, (b) the head is coaxial with the central longitudinal axis, and (c) the tissue-coupling element is shaped such that if the tissue-coupling element were to be projected onto a plane that is perpendicular to the central longitudinal axis, (i) at least 80% (e.g., at least 90%, such as at least 95%) of an area of a projection of the tissue-coupling element on the plane would fall within a first angle of 180 degrees in the plane having a vertex at the central longitudinal axis, and (ii) the area would partially overlap, at a distance of at least 3 mm from the vertex, both rays of a second angle of between 45 and 180 degrees in the plane having the vertex at the central longitudinal axis.

For some applications, when the tissue anchor is unconstrained by the deployment tool, a wire thereof (a) is shaped as an open loop (e.g., a three-dimensional open loop), such as a spiral (e.g., a three-dimensional spiral) around a center point, and (b) extends from a distal end of the shaft at a radially-outer end of the open loop, e.g., spiral. Typically, the tissue-coupling element is non-helical when the tissue anchor is unconstrained by the deployment tool.

For some applications, the tissue anchor further comprises a flexible elongate tension member, which is typically distinct from the wire of the tissue-coupling element, and which is fixed to a site on the open loop and crosses at least a portion of the open loop when the tissue anchor is unconstrained by the deployment tool. To this end, the flexible elongate tension member typically includes (a) a distal portion that is fixed to a site on the open loop (such as on an outermost turn of the open loop), (b) a proximal portion, which has a longitudinal segment that runs alongside at least a portion of the shaft, and (c) a crossing portion, which (i) is disposed between the distal and the proximal portions along the flexible elongate tension member, and (ii) crosses at least a portion of the open loop when the tissue anchor is unconstrained by the deployment tool. Tension is applied to the tissue-coupling element of the tissue anchor via the flexible elongate tension member. The applied tension is resisted by the outward force of the open loop. The applied tension compresses and stiffens the open loop. This arrangement of tension distribution may overcome any natural tendency of the open loop to straighten if tension were to be applied along the central longitudinal axis via the shaft, and thus may allow the application of a greater load to the open loop. It is noted that the maximum design stiffness of the open loop is constrained by the need for the open loop to be straightened for delivery in a shaft of the deployment tool.

For some applications, the head is shaped so as to define a passage in which the proximal portion of the flexible elongate tension member is slidably disposed. The flexible elongate tension member comprises a locking stopper, which is axially fixed to the proximal or the crossing portion of the flexible elongate tension member. The locking stopper and the passage are sized and shaped such that the size and shape of the passage prevent proximal movement of the locking stopper past the passage. The locking stopper limits the total load that can be applied to the open loop by the flexible elongate tension member, thereby reducing excessive, unnecessary strain on the open loop. Additional load (tension) that is applied by the flexible elongate tension member pulls on the entire anchor, and does not further increase the load applied across the open loop.

Typically, the tissue anchor is configured to allow relative axial motion between the at least a portion of the shaft and the longitudinal segment of the proximal portion of the flexible elongate tension member when the tissue anchor is unconstrained by the deployment tool. Such axial motion allows tension to be applied to the flexible elongate tension member without also being applied to the shaft, and allows the open loop to be unwound and the flexible elongate tension member to be disposed alongside a portion of the flexible elongate tension member. Typically, the longitudinal segment of the proximal portion of the flexible elongate tension member is coupled in sliding communication with the at least a portion of the shaft when the tissue anchor is unconstrained by the deployment tool. For some applications, the tissue anchor comprises one or more annular elements, which are disposed around the at least a portion of the shaft, and couple the flexible elongate tension member in the sliding communication with the at least a portion of the shaft when the tissue anchor is unconstrained by the deployment tool. For example, the annular elements may comprise one or more collars, loops, or rings.

In experiments on porcine heart cadavers conducted by the inventors, a tissue anchor comprising the spiral and the flexible elongate tension member remained firmly implanted in tissue of the ventricular wall, without damaging the tissue, and without fracturing of the anchor under high loads. The inventors found that loads of up to 25 N could be safety applied. It was noted that the tension applied through the flexible elongate tension member was of a magnitude of three times that of the load that could be applied through the central longitudinal axis of the shaft.

For some applications, a tissue anchor system is provided, which comprises (a) a first off-center tissue anchor, such as described above, (b) a second tissue anchor, and (c) one or more tethers, which are configured to couple (i) the head of first tissue anchor to (ii) the second tissue anchor. For some applications, the second tissue anchor comprises a helical tissue-coupling element. For other applications, the second tissue anchor comprises a stent. For applications in which the tissue anchor comprises the flexible elongate tension member, as described above, the one or more tethers are fixed to the flexible elongate tension member. When tension is applied to the one or more tethers, the tension is transmitted to the flexible elongate tension member, rather than to the shaft via the head.

For some applications, the tissue-coupling element comprises three or more tines, such as four or more tines. In these applications, when the tissue anchor is unconstrained by the deployment tool, (a) the shaft has a central longitudinal axis, (b) the tines extend radially outward from the central longitudinal axis in respective directions that are fixed with respect to one another, and (c) the tissue-coupling element is shaped such that if the tissue-coupling element were to be projected onto a plane that is perpendicular to the central longitudinal axis, at least 80% of an area of a projection of the tissue-coupling element on the plane would fall within an angle of 210 degrees in the plane having a vertex at the central longitudinal axis.

For some applications, the tissue-coupling element further comprises one or more membranes that are fixed to and extend between circumferentially-adjacent ones of the tines. The membranes and tines together might be considered to define a structure similar in some respect to a bat wing, or a partial umbrella. The membranes may help evenly distribute the force on the external surface of the heart applied by the tissue-coupling element.

There is therefore provided, in accordance with an inventive concept 1 of the present invention, apparatus for delivery in a constrained state within a deployment tool, the apparatus comprising a tissue anchor, which comprises:
a shaft;
a tissue-coupling element, which comprises a wire, which is shaped as an open loop having more than one turn when the tissue anchor is unconstrained by the deployment tool; and
a flexible elongate tension member, which includes (a) a distal portion that is fixed to a site on the open loop, (b) a proximal portion, which has a longitudinal segment that runs alongside at least a portion of the shaft, and (c) a crossing portion, which (i) is disposed between the distal and the proximal portions along the flexible elongate tension member, and (ii) crosses at least a portion of the open loop when the tissue anchor is unconstrained by the deployment tool,
wherein the tissue anchor is configured to allow relative axial motion between the at least a portion of the shaft and the longitudinal segment of the proximal portion of the flexible elongate tension member when the tissue anchor is unconstrained by the deployment tool.

Inventive concept 2. The apparatus according to inventive concept 1, wherein the open loop is shaped as a spiral when the tissue anchor is unconstrained by the deployment tool.

Inventive concept 3. The apparatus according to inventive concept 2, wherein the spiral is shaped as a three-dimensional spiral when the tissue anchor is unconstrained by the deployment tool.

Inventive concept 4. The apparatus according to inventive concept 2, wherein the spiral is shaped as an elliptical spiral when the tissue anchor is unconstrained by the deployment tool.

Inventive concept 5. The apparatus according to inventive concept 1, wherein the open loop is shaped as a three-dimensional open loop when the tissue anchor is unconstrained by the deployment tool.

Inventive concept 6. The apparatus according to inventive concept 5, wherein, when the tissue anchor is unconstrained by the deployment tool:
a greatest longitudinal dimension of the three-dimensional open loop, measured in parallel to a central longitudinal axis of the shaft, is between 1 and 5 mm, and
a greatest lateral dimension of the three-dimensional open loop, measured perpendicular to the central longitudinal axis, is between 4 and 20 mm.

Inventive concept 7. The apparatus according to inventive concept 1, wherein the site is on an outermost turn of the open loop when the tissue anchor is unconstrained by the deployment tool.

Inventive concept 8. The apparatus according to inventive concept 1, wherein the site is on a second-to-outermost turn of the open loop when the tissue anchor is unconstrained by the deployment tool.

Inventive concept 9. The apparatus according to inventive concept 1, wherein a radius of the flexible elongate tension member is less than a radius of the wire.

Inventive concept 10. The apparatus according to inventive concept 9, wherein the radius of the flexible elongate tension member is less than 50% of the radius of the wire.

Inventive concept 11. The apparatus according to inventive concept 1, wherein, when the tissue anchor is unconstrained by the deployment tool and the flexible elongate tension member is tensioned straight, if the tissue-coupling element and the flexible elongate tension member were to be projected onto a plane that is perpendicular to a central longitudinal axis of the shaft, an angle between (a) the flexible elongate tension member and (b) a tangent to the open loop at the site would be between 70 and 90 degrees.

Inventive concept 12. The apparatus according to inventive concept 1, wherein, when the tissue anchor is unconstrained by the deployment tool:
the open loop is shaped so as to define an outermost turn and a second-to-outermost at least partial turn, and
the outermost turn at least partially overlaps the second-to-outermost at least partial turn.

Inventive concept 13. The apparatus according to inventive concept 1, wherein, when the tissue anchor is unconstrained by the deployment tool, the open loop is shaped so as to define one or more curved segments and one or more straight segments.

Inventive concept 14. The apparatus according to inventive concept 13, wherein, when the tissue anchor is unconstrained by the deployment tool, the open loop is shaped so as to define the one or more curved segments and two or more straight segments.

Inventive concept 15. The apparatus according to inventive concept 1, wherein, when the tissue anchor is unconstrained by the deployment tool:
the open loop has a greatest lateral dimension, measured perpendicular to a central longitudinal axis of the shaft, and
a distance between (a) a radially-outer end of the open loop and (b) a radially-inner-most point of the open loop, measured perpendicular to the central longitudinal axis, is equal to at least 30% of the greatest lateral dimension.

Inventive concept 16. The apparatus according to inventive concept 15, wherein a ratio of the greatest longitudinal dimension and the greatest lateral dimension is between 1:2 and 1:18 when the tissue anchor is unconstrained by the deployment tool.

Inventive concept 17. The apparatus according to inventive concept 1, wherein the shaft comprises a sealing element.

Inventive concept 18. The apparatus according to inventive concept 1, wherein the shaft has a central longitudinal axis that is straight when the tissue anchor is unconstrained by the deployment tool.

Inventive concept 19. The apparatus according to inventive concept 1, wherein the shaft is flexible.

Inventive concept 20. The apparatus according to inventive concept 1, wherein the shaft and the tissue-coupling element are integral to one another.

Inventive concept 21. The apparatus according to inventive concept 1, wherein a cross-sectional area of the wire is at least 0.09 mm2.

Inventive concept 22. The apparatus according to inventive concept 21, wherein the cross-sectional area of the wire is no more than 2.9 mm2.

Inventive concept 23. The apparatus according to inventive concept 1, wherein the flexible elongate tension member comprises Nitinol.

Inventive concept 24. The apparatus according to any one of inventive concepts 1-23, wherein the tissue anchor comprises a head connected to a proximal portion of the shaft,
wherein the head is shaped so as to define a passage in which the proximal portion of the flexible elongate tension member is slidably disposed,
wherein the flexible elongate tension member comprises a locking stopper, which is axially fixed to the proximal or the crossing portion of the flexible elongate tension member, and
wherein the locking stopper and the passage are sized and shaped such that the size and shape of the passage prevent proximal movement of the locking stopper past the passage.

Inventive concept 25. The apparatus according to inventive concept 24, wherein the locking stopper is axially fixed to the proximal or the crossing portion of the flexible elongate tension member at a distance of between 7 and 22 mm from the site on the open loop.

Inventive concept 26. The apparatus according to inventive concept 24, wherein, if the tissue-coupling element were straightened in an elongated configuration, the locking stopper would be a distance of between 7 and 12 mm from the passage.

Inventive concept 27. The apparatus according to any one of inventive concepts 1-23, wherein the site on the open loop is a first site on the open loop, and wherein, when the tissue anchor is unconstrained by the deployment tool and the flexible elongate tension member is tensioned straight:
the open loop surrounds a center point,
the wire extends from the distal end of the shaft at a second site on the open loop, and
if the tissue-coupling element and the flexible elongate tension member were to be projected onto a plane that is perpendicular to a central longitudinal axis of the shaft, an angle between the first and the second sites, having a vertex at the center point, would be between 130 and 180 degrees.

Inventive concept 28. The apparatus according to inventive concept 27, wherein the angle is between 150 and 180 degrees.

Inventive concept 29. The apparatus according to inventive concept 28, wherein the angle is between 170 and 180 degrees.

Inventive concept 30. The apparatus according to inventive concept 27, the second site is at a radially-outer end of the open loop when the tissue anchor is unconstrained by the deployment tool.

Inventive concept 31. The apparatus according to any one of inventive concepts 1-23, wherein, when the tissue anchor is unconstrained by the deployment tool:
the open loop surrounds a center point, and
(a) a site distance between the site and the distal end of the shaft is greater than (b) a center-point distance between the center point and the distal end of the shaft, when the tissue anchor is unconstrained by the deployment tool.

Inventive concept 32. The apparatus according to inventive concept 31, wherein the site distance equals at least 150% of the center-point distance when the tissue anchor is unconstrained by the deployment tool.

Inventive concept 33. The apparatus according to inventive concept 32, wherein the site distance equals at least 175% of the center-point distance when the tissue anchor is unconstrained by the deployment tool.

Inventive concept 34. The apparatus according to any one of inventive concepts 1-23, wherein the longitudinal segment of the proximal portion of the flexible elongate tension member is coupled in sliding communication with the at least a portion of the shaft when the tissue anchor is unconstrained by the deployment tool.

Inventive concept 35. The apparatus according to inventive concept 34, wherein the tissue anchor comprises one or more annular elements, which are disposed around the at least a portion of the shaft, and couple the flexible elongate tension member in the sliding communication with the at least a portion of the shaft when the tissue anchor is unconstrained by the deployment tool.

Inventive concept 36. The apparatus according to any one of inventive concepts 1-23, wherein the flexible elongate tension member is not fixed to any portion of the open loop beyond 2 mm from the site on the open loop, measured when the tissue anchor is unconstrained by the deployment tool.

Inventive concept 37. The apparatus according to any one of inventive concepts 1-23, wherein, when the tissue anchor is unconstrained by the deployment tool:

the open loop has a greatest lateral dimension, measured perpendicular to a central longitudinal axis of the shaft, and the flexible elongate tension member is not fixed to any portion of the open loop beyond a distance from the site on the open loop, wherein the distance equals 30% of the greatest lateral dimension.

Inventive concept 38. The apparatus according to any one of inventive concepts 1-23, wherein the flexible elongate tension member is fixed to the open loop only at the site on the open loop.

Inventive concept 39. The apparatus according to any one of inventive concepts 1-23, wherein, when the tissue anchor is unconstrained by the deployment tool:

the open loop has a greatest lateral dimension, measured perpendicular to a central longitudinal axis of the shaft, and the at least a portion of the open loop crossed by the crossing portion has a length that equals at least 50% of the greatest lateral dimension.

Inventive concept 40. The apparatus according to inventive concept 39, wherein the length of the at least a portion of the open loop crossed by the crossing portion equals at least 75% of the greatest lateral dimension when the tissue anchor is unconstrained by the deployment tool.

Inventive concept 41. The apparatus according to inventive concept 40, wherein the length of the at least a portion of the open loop crossed by the crossing portion equals at least 90% of the greatest lateral dimension when the tissue anchor is unconstrained by the deployment tool.

Inventive concept 42. The apparatus according to any one of inventive concepts 1-23, wherein the wire extends from a distal end of the shaft at a radially-outer end of the open loop when the tissue anchor is unconstrained by the deployment tool.

Inventive concept 43. The apparatus according to inventive concept 42, wherein, when the tissue anchor is unconstrained by the deployment tool, the open loop surrounds a center point, and the wire intersects the center point.

Inventive concept 44. The apparatus according to inventive concept 42, wherein, when the tissue anchor is unconstrained by the deployment tool, the open loop surrounds a center point, and the wire does not intersect the center point.

Inventive concept 45. The apparatus according to any one of inventive concepts 1-23, wherein the wire extends from a distal end of the shaft at a radially-inner end of the open loop when the tissue anchor is unconstrained by the deployment tool.

Inventive concept 46. The apparatus according to inventive concept 45, wherein the flexible elongate tension member is a first flexible elongate tension member, the distal portion is a first distal portion, the proximal portion is a first proximal portion, the crossing portion is a first crossing portion, the site is a first site, the at least a portion of the open loop is at least a first portion of the open loop, and the longitudinal segment of the flexible elongate tension member is a first longitudinal segment of the first flexible elongate tension member, wherein the tissue anchor comprises a second flexible elongate tension member, which includes (a) a second distal portion that is fixed to a second site on the open loop, different from the first site, (b) a second proximal portion, which has a second longitudinal segment that runs alongside at least a portion of the shaft, and (c) a second crossing portion, which (i) is disposed between the second distal and the second proximal portions along the second flexible elongate tension member, and (ii) crosses at least a second portion of the open loop when the tissue anchor is unconstrained by the deployment tool, and wherein the tissue anchor is configured to allow relative axial motion between the at least a portion of the shaft and the second longitudinal segment of the second proximal portion of the second flexible elongate tension member when the tissue anchor is unconstrained by the deployment tool.

Inventive concept 47. The apparatus according to inventive concept 46, wherein the first proximal portion of the first flexible elongate tension member and the second proximal portion of the second flexible elongate tension member join one another.

Inventive concept 48. The apparatus according to any one of inventive concepts 1-23, wherein a proximally-facing surface defined by the tissue-coupling element is concave when the tissue anchor is unconstrained by the deployment tool.

Inventive concept 49. The apparatus according to any one of inventive concepts 1-23, wherein a proximally-facing surface defined by the tissue-coupling element is convex when the tissue anchor is unconstrained by the deployment tool.

Inventive concept 50. The apparatus according to any one of inventive concepts 1-23, wherein the apparatus further comprises one or more tethers, which are fixed to the flexible elongate tension member.

Inventive concept 51. The apparatus according to any one of inventive concepts 1-23, wherein the tissue anchor is a first tissue anchor, and
wherein the apparatus further comprises:
a second tissue anchor, which is separate and distinct from the first tissue anchor; and
one or more tethers, which are configured to couple (a) the flexible elongate tension member to (b) the second tissue anchor.

Inventive concept 52. The apparatus according to inventive concept 51, wherein the one or more tethers are fixed to (a) the flexible elongate tension member and (b) the second tissue anchor.

Inventive concept 53. The apparatus according to inventive concept 51, wherein the one or more tethers are (a) fixed to the second tissue anchor and (b) not fixed to the shaft of the first tissue anchor.

Inventive concept 54. The apparatus according to inventive concept 51, wherein the second tissue anchor comprises a helical tissue-coupling element.

Inventive concept 55. The apparatus according to inventive concept 51, wherein the second tissue anchor comprises a stent.

Inventive concept 56. The apparatus according to any one of inventive concepts 1-23, wherein the tissue anchor is a first tissue anchor, and
wherein the apparatus further comprises a second tissue anchor, which is separate and distinct from the first tissue anchor, and wherein the flexible elongate tension member is coupled to the second tissue anchor.

Inventive concept 57. The apparatus according to inventive concept 56, wherein the flexible elongate tension member is fixed to the second tissue anchor.

Inventive concept 58. The apparatus according to any one of inventive concepts 1-23, further comprising a deployment tool, which comprises a sharp distal piercing tip, and which is configured to constrain the tissue-coupling element while delivering the tissue-coupling element through tissue, and wherein, when the tissue-coupling element is constrained by the deployment tool, a longitudinal portion of the flexible elongate tension member runs alongside a portion of the wire.

There is further provided, in accordance with an inventive concept 59 of the present invention, apparatus for delivery in a constrained state within a deployment tool, the apparatus comprising:

a tissue anchor, which comprises (a) a shaft, (b) a head connected to a proximal portion of the shaft, and (c) a tissue-coupling element, which extends from a distal end of the shaft; and a deployment tool, which comprises a sharp distal piercing tip, and which is configured to constrain the tissue-coupling element while delivering the tissue-coupling element through tissue, wherein, when the tissue anchor is unconstrained by the deployment tool:

the shaft has a central longitudinal axis, the head is coaxial with the central longitudinal axis, and the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 60. The apparatus according to inventive concept 59, wherein at least 95% of the area of the projection of the tissue-coupling element on the plane would fall within the first angle.

Inventive concept 61. The apparatus according to inventive concept 59, wherein at least 80% of the area of the projection of the tissue-coupling element on the plane would fall within a third angle of 150 degrees in the plane having the vertex at the central longitudinal axis.

Inventive concept 62. The apparatus according to inventive concept 59, wherein an outer portion of the area of the projection of the tissue-coupling element on the plane would fall within all angular positions of a fourth angle of 90 degrees in the plane having the vertex at the central longitudinal axis, which outer portion consists of all points of the area at least 3 mm from the vertex.

Inventive concept 63. The apparatus according to inventive concept 59, wherein a proximally-facing surface defined by the tissue-coupling element is concave when the tissue anchor is unconstrained by the deployment tool.

Inventive concept 64. The apparatus according to inventive concept 59, wherein, when the tissue anchor is unconstrained by the deployment tool:

a greatest longitudinal dimension of the tissue-coupling element, measured parallel to the central longitudinal axis, is between 1 and 5 mm, and a greatest lateral dimension of the tissue-coupling element, measured perpendicular to the central longitudinal axis, is between 4 and 20 mm.

Inventive concept 65. The apparatus according to inventive concept 64, wherein a ratio of the greatest longitudinal dimension and the greatest lateral dimension is between 1:2 and 1:18 when the tissue anchor is unconstrained by the deployment tool.

Inventive concept 66. The apparatus according to inventive concept 59, wherein the tissue-coupling element has a length of 5 to 60 mm when constrained into a straight configuration.

Inventive concept 67. The apparatus according to inventive concept 59, wherein the tissue-coupling element has one or more distal ends, each of which does not define a sharp distal tip.

Inventive concept 68. The apparatus according to inventive concept 67, wherein each of the distal ends is blunt.

Inventive concept 69. The apparatus according to inventive concept 59, wherein the tissue-coupling element is non-helical when the tissue anchor is unconstrained by the deployment tool.

Inventive concept 70. The apparatus according to inventive concept 59, wherein the shaft comprises a sealing element.

Inventive concept 71. The apparatus according to inventive concept 59, wherein the central longitudinal axis is straight when the tissue anchor is unconstrained by the deployment tool.

Inventive concept 72. The apparatus according to inventive concept 59, wherein the shaft is flexible.

Inventive concept 73. The apparatus according to inventive concept 59, wherein the shaft and the tissue-coupling element are integral to one another.

Inventive concept 74. The apparatus according to inventive concept 73, wherein the shaft and the tissue-coupling element comprise a wire.

Inventive concept 75. The apparatus according to inventive concept 59, wherein the deployment tool comprises a hypodermic needle.

Inventive concept 76. The apparatus according to any one of inventive concepts 59-75, wherein the tissue-coupling element comprises at least three tines that extend radially outward from the central longitudinal axis in respective directions that are fixed with respect to one another when the tissue anchor is unconstrained by the deployment tool.

Inventive concept 77. The apparatus according to inventive concept 76, wherein tines comprise at least four tines.

Inventive concept 78. The apparatus according to any one of inventive concepts 59-75, wherein the tissue-coupling element comprises a wire.

Inventive concept 79. The apparatus according to inventive concept 78, wherein the wire is shaped as an open loop having more than one turn, when the tissue anchor is unconstrained by the deployment tool, wherein the tissue anchor further comprises a flexible elongate tension member, which includes (a) a distal portion that is fixed to a site on the open loop, (b) a proximal portion, which has a longitudinal segment that runs alongside at least a portion of the shaft, and (c) a crossing portion, which (i) is disposed between the distal and the proximal portions along the flexible elongate tension member, and (ii) crosses at least a portion of the open loop when the tissue anchor is unconstrained by the deployment tool, and wherein the tissue anchor is configured to allow relative axial motion between the at least a portion of the shaft and the longitudinal segment of the proximal portion of the flexible elongate tension member when the tissue anchor is unconstrained by the deployment tool.

Inventive concept 80. The apparatus according to inventive concept 79, wherein the head is shaped so as to define a passage in which the proximal portion of the flexible elongate tension member is slidably disposed, wherein the flexible elongate tension member comprises a locking stopper, which is axially fixed to the proximal or the crossing portion of the flexible elongate tension member, and wherein the locking stopper and the passage are sized and shaped such that the size and shape of the passage prevent proximal movement of the locking stopper past the passage.

Inventive concept 81. The apparatus according to inventive concept 79, wherein the open loop is shaped as a spiral when the tissue anchor is unconstrained by the deployment tool.

Inventive concept 82. The apparatus according to inventive concept 81, wherein the spiral is shaped as a three-dimensional spiral when the tissue anchor is unconstrained by the deployment tool.

Inventive concept 83. The apparatus according to inventive concept 81, wherein the spiral is shaped as an elliptical spiral when the tissue anchor is unconstrained by the deployment tool.

Inventive concept 84. The apparatus according to inventive concept 79, wherein the open loop is shaped as a three-dimensional open loop when the tissue anchor is unconstrained by the deployment tool.

Inventive concept 85. The apparatus according to inventive concept 79, wherein, when the tissue anchor is unconstrained by the deployment tool:

the open loop surrounds a center point, and (a) a site distance between the site and the distal end of the shaft is greater than (b) a center-point distance between the center point and the distal end of the shaft when the tissue anchor is unconstrained by the deployment tool.

Inventive concept 86. The apparatus according to inventive concept 85, wherein the site distance equals at least 150% of the center-point distance when the tissue anchor is unconstrained by the deployment tool.

Inventive concept 87. The apparatus according to inventive concept 86, wherein the site distance equals at least 175% of the center-point distance when the tissue anchor is unconstrained by the deployment tool.

Inventive concept 88. The apparatus according to inventive concept 79, wherein the site is on an outermost turn of the open loop when the tissue anchor is unconstrained by the deployment tool.

Inventive concept 89. The apparatus according to inventive concept 79, wherein the site is on a second-to-outermost turn of the open loop when the tissue anchor is unconstrained by the deployment tool.

Inventive concept 90. The apparatus according to inventive concept 79, wherein a radius of the flexible elongate tension member is less than a radius of the wire.

Inventive concept 91. The apparatus according to inventive concept 90, wherein the radius of the flexible elongate tension member is less than 50% of the radius of the wire.

Inventive concept 92. The apparatus according to inventive concept 79, wherein the longitudinal segment of the proximal portion of the flexible elongate tension member is coupled in sliding communication with the at least a portion of the shaft when the tissue anchor is unconstrained by the deployment tool.

Inventive concept 93. The apparatus according to inventive concept 92, wherein the tissue anchor comprises one or more annular elements, which are disposed around the at least a portion of the shaft, and couple the flexible elongate tension member in the sliding communication with the at least a portion of the shaft when the tissue anchor is unconstrained by the deployment tool.

Inventive concept 94. The apparatus according to inventive concept 79, wherein the flexible elongate tension member is not fixed to any portion of the open loop beyond 2 mm from the site on the open loop, measured when the tissue anchor is unconstrained by the deployment tool.

Inventive concept 95. The apparatus according to inventive concept 79, wherein, when the tissue anchor is unconstrained by the deployment tool:

the open loop has a greatest lateral dimension, measured perpendicular to the central longitudinal axis, and the flexible elongate tension member is not fixed to any portion of the open loop beyond a distance from the site on the open loop, wherein the distance equals 30% of the greatest lateral dimension.

Inventive concept 96. The apparatus according to inventive concept 79, wherein the flexible elongate tension member is fixed to the open loop only at the site on the open loop.

Inventive concept 97. The apparatus according to inventive concept 79, wherein, when the tissue anchor is unconstrained by the deployment tool:

the open loop has a greatest lateral dimension, measured perpendicular to the central longitudinal axis, and the at least a portion of the open loop crossed by the crossing portion has a length that equals at least 50% of the greatest lateral dimension.

Inventive concept 98. The apparatus according to inventive concept 97, wherein the length of the at least a portion of the open loop crossed by the crossing portion equals at least 75% of the greatest lateral dimension when the tissue anchor is unconstrained by the deployment tool.

Inventive concept 99. The apparatus according to inventive concept 98, wherein the length of the at least a portion of the open loop crossed by the crossing portion equals at least 90% of the greatest lateral dimension when the tissue anchor is unconstrained by the deployment tool.

Inventive concept 100. The apparatus according to inventive concept 79, wherein, when the tissue anchor is unconstrained by the deployment tool and the flexible elongate tension member is tensioned straight, if the tissue-coupling element and the flexible elongate tension member were to be projected onto the plane that is perpendicular to the central longitudinal axis, an angle between (a) the flexible elongate tension member and (b) a tangent to the open loop at the site would be between 70 and 90 degrees.

Inventive concept 101. The apparatus according to inventive concept 79, wherein the site on the open loop is a first site on the open loop, and wherein, when the tissue anchor is unconstrained by the deployment tool and the flexible elongate tension member is tensioned straight:

the open loop surrounds a center point, the wire extends from the distal end of the shaft at a second site on the open loop, and if the tissue-coupling element and the flexible elongate tension member were to be projected onto the plane that is perpendicular to the central longitudinal axis, a third angle between the first and the second sites, having a vertex at the center point, would be between 130 and 180 degrees.

Inventive concept 102. The apparatus according to inventive concept 101, wherein the third angle is between 150 and 180 degrees.

Inventive concept 103. The apparatus according to inventive concept 102, wherein the third angle is between 170 and 180 degrees.

Inventive concept 104. The apparatus according to inventive concept 101, the second site is at a radially-outer end of the open loop when the tissue anchor is unconstrained by the deployment tool.

Inventive concept 105. The apparatus according to inventive concept 79, wherein the flexible elongate tension member comprises Nitinol.

Inventive concept 106. The apparatus according to inventive concept 79, wherein the apparatus further comprises one or more tethers, which are fixed to the flexible elongate tension member.

Inventive concept 107. The apparatus according to inventive concept 79,
  wherein the tissue anchor is a first tissue anchor, and
  wherein the apparatus further comprises:
  a second tissue anchor, which is separate and distinct from the first tissue anchor; and
  one or more tethers, which are configured to couple (a) the flexible elongate tension member to (b) the second tissue anchor.

Inventive concept 108. The apparatus according to inventive concept 107, wherein the one or more tethers are fixed to (a) the flexible elongate tension member to (b) the second tissue anchor.

Inventive concept 109. The apparatus according to inventive concept 107, wherein the second tissue anchor comprises a helical tissue-coupling element.

Inventive concept 110. The apparatus according to inventive concept 107, wherein the second tissue anchor comprises a stent.

Inventive concept 111. The apparatus according to inventive concept 79,
  wherein the tissue anchor is a first tissue anchor, and
  wherein the apparatus further comprises a second tissue anchor, which is separate and distinct from the first tissue anchor, and
  wherein the flexible elongate tension member is coupled to the second tissue anchor.

Inventive concept 112. The apparatus according to inventive concept 111, wherein the flexible elongate tension member is fixed to the second tissue anchor.

Inventive concept 113. The apparatus according to inventive concept 79, wherein, when the tissue-coupling element is constrained by the deployment tool, a longitudinal portion of the flexible elongate tension member runs alongside a portion of the wire.

Inventive concept 114. The apparatus according to inventive concept 78, wherein, when the tissue anchor is unconstrained by the deployment tool:
  the wire of the tissue-coupling element is shaped as an open loop having more than one turn around a center point, and
  the wire extends from the distal end of the shaft at a radially-outer end of the open loop.

Inventive concept 115. The apparatus according to inventive concept 114, wherein the open loop is shaped as a spiral when the tissue anchor is unconstrained by the deployment tool.

Inventive concept 116. The apparatus according to inventive concept 115, wherein the spiral is shaped as a three-dimensional spiral when the tissue anchor is unconstrained by the deployment tool.

Inventive concept 117. The apparatus according to inventive concept 115, wherein the spiral is shaped as an elliptical spiral when the tissue anchor is unconstrained by the deployment tool.

Inventive concept 118. The apparatus according to inventive concept 114, wherein the open loop is shaped as a three-dimensional open loop when the tissue anchor is unconstrained by the deployment tool.

Inventive concept 119. The apparatus according to inventive concept 114, wherein the wire intersects the center point when the tissue anchor is unconstrained by the deployment tool.

Inventive concept 120. The apparatus according to inventive concept 114, wherein the wire does not intersect the center point when the tissue anchor is unconstrained by the deployment tool.

Inventive concept 121. The apparatus according to inventive concept 114, wherein, when the tissue anchor is unconstrained by the deployment tool:
  the open loop has a greatest lateral dimension, measured perpendicular to the central longitudinal axis, and
  a distance between (a) the radially-outer end of the open loop and (b) a radially-inner-most point of the open loop, measured perpendicular to the central longitudinal axis, is equal to at least 30% of the greatest lateral dimension.

Inventive concept 122. The apparatus according to inventive concept 114, wherein a proximally-facing surface defined by the tissue-coupling element is convex when the tissue anchor is unconstrained by the deployment tool.

Inventive concept 123. The apparatus according to inventive concept 78, wherein a cross-sectional area of the wire is at least 0.09 mm2.

Inventive concept 124. The apparatus according to inventive concept 123, wherein the cross-sectional area of the wire is no more than 2.9 mm2.

Inventive concept 125. The apparatus according to any one of inventive concepts 59-75,
  wherein the tissue anchor is a first tissue anchor, and
  wherein the apparatus further comprises:
  a second tissue anchor, which is separate and distinct from the first tissue anchor; and
  one or more tethers, which are configured to couple (a) the head of the first tissue anchor to (b) the second tissue anchor.

Inventive concept 126. The apparatus according to inventive concept 125, wherein the one or more tethers are fixed to (a) the head of the first tissue anchor to (b) the second tissue anchor.

Inventive concept 127. The apparatus according to inventive concept 125, wherein the second tissue anchor comprises a helical tissue-coupling element.

Inventive concept 128. The apparatus according to inventive concept 125, wherein the second tissue anchor comprises a stent.

There is still further provided, in accordance with an inventive concept 129 of the present invention, apparatus for delivery in a constrained state within a deployment tool, the apparatus comprising a tissue anchor, which comprises:
- a shaft; and
- a tissue-coupling element, which comprises a wire;

wherein, when the tissue anchor is unconstrained by the deployment tool:
- the shaft has a central longitudinal axis,
- the wire of the tissue-coupling element is shaped as an open loop having more than one turn around a center point, and
- the wire extends from a distal end of the shaft at a radially-outer end of the open loop.

Inventive concept 130. The apparatus according to inventive concept 129, wherein the open loop is shaped as a spiral when the tissue anchor is unconstrained by the deployment tool.

Inventive concept 131. The apparatus according to inventive concept 130, wherein the spiral is shaped as a three-dimensional spiral when the tissue anchor is unconstrained by the deployment tool.

Inventive concept 132. The apparatus according to inventive concept 130, wherein the spiral is shaped as an elliptical spiral when the tissue anchor is unconstrained by the deployment tool.

Inventive concept 133. The apparatus according to inventive concept 129, wherein the open loop is shaped as a three-dimensional open loop when the tissue anchor is unconstrained by the deployment tool.

Inventive concept 134. The apparatus according to inventive concept 133, wherein, when the tissue anchor is unconstrained by the deployment tool:
- a greatest longitudinal dimension of the three-dimensional open loop, measured in parallel to the central longitudinal axis, is between 1 and 5 mm, and
- a greatest lateral dimension of the three-dimensional open loop, measured perpendicular to the central longitudinal axis, is between 4 and 20 mm.

Inventive concept 135. The apparatus according to inventive concept 129, wherein the wire intersects the center point when the tissue anchor is unconstrained by the deployment tool.

Inventive concept 136. The apparatus according to inventive concept 129, wherein the wire does not intersect the center point when the tissue anchor is unconstrained by the deployment tool.

Inventive concept 137. The apparatus according to inventive concept 129, wherein, when the tissue anchor is unconstrained by the deployment tool:
- the open loop has a greatest lateral dimension, measured perpendicular to the central longitudinal axis, and
- a distance between (a) the radially-outer end of the open loop and (b) a radially-inner-most point of the open loop, measured perpendicular to the central longitudinal axis, is equal to at least 30% of the greatest lateral dimension.

Inventive concept 138. The apparatus according to inventive concept 134, wherein a ratio of the greatest longitudinal dimension and the greatest lateral dimension is between 1:2 and 1:18 when the tissue anchor is unconstrained by the deployment tool.

Inventive concept 139. The apparatus according to inventive concept 129, wherein the shaft comprises a sealing element.

Inventive concept 140. The apparatus according to inventive concept 129, wherein the central longitudinal axis is straight when the tissue anchor is unconstrained by the deployment tool.

Inventive concept 141. The apparatus according to inventive concept 129, wherein the shaft is flexible.

Inventive concept 142. The apparatus according to inventive concept 129, wherein the shaft and the tissue-coupling element are integral to one another.

Inventive concept 143. The apparatus according to any one of inventive concepts 129-142,
wherein the tissue anchor further comprises a flexible elongate tension member, which includes (a) a distal portion that is fixed to a site on the open loop, (b) a proximal portion, which has a longitudinal segment that runs alongside at least a portion of the shaft, and (c) a crossing portion, which (i) is disposed between the distal and the proximal portions along the flexible elongate tension member, and (ii) crosses at least a portion of the open loop when the tissue anchor is unconstrained by the deployment tool, and
wherein the tissue anchor is configured to allow relative axial motion between the at least a portion of the shaft and the longitudinal segment of the proximal portion of the flexible elongate tension member when the tissue anchor is unconstrained by the deployment tool.

Inventive concept 144. The apparatus according to inventive concept 143, wherein the site is on an outermost turn of the open loop when the tissue anchor is unconstrained by the deployment tool.

Inventive concept 145. The apparatus according to inventive concept 143, wherein the site is on a second-to-outermost turn of the open loop when the tissue anchor is unconstrained by the deployment tool.

Inventive concept 146. The apparatus according to inventive concept 143, wherein a radius of the flexible elongate tension member is less than a radius of the wire.

Inventive concept 147. The apparatus according to inventive concept 146, wherein the radius of the flexible elongate tension member is less than 50% of the radius of the wire.

Inventive concept 148. The apparatus according to inventive concept 143, wherein, when the tissue anchor is unconstrained by the deployment tool and the flexible elongate tension member is tensioned straight, if the tissue-coupling element and the flexible elongate tension member were to be projected onto a plane that is perpendicular to the central longitudinal axis, an angle between (a) the flexible elongate tension member and (b) a tangent to the open loop at the site would be between 70 and 90 degrees.

Inventive concept 149. The apparatus according to inventive concept 143, wherein the site on the open loop is a first site on the open loop, and wherein, when the tissue anchor is unconstrained by the deployment tool and the flexible elongate tension member is tensioned straight:
- the wire extends from the distal end of the shaft at a second site on the open loop, and
- if the tissue-coupling element and the flexible elongate tension member were to be projected onto a plane that is perpendicular to the central longitudinal axis, an angle between the first and the second sites, having a vertex at the center point, would be between 130 and 180 degrees.

Inventive concept 150. The apparatus according to inventive concept 149, wherein the angle is between 150 and 180 degrees.

Inventive concept 151. The apparatus according to inventive concept 150, wherein the angle is between 170 and 180 degrees.

Inventive concept 152. The apparatus according to inventive concept 149, the second site is at a radially-outer end of the open loop when the tissue anchor is unconstrained by the deployment tool.

Inventive concept 153. The apparatus according to inventive concept 143, wherein, when the tissue anchor is unconstrained by the deployment tool:
the open loop has a greatest lateral dimension, measured perpendicular to the central longitudinal axis, and
a distance between (a) a radially-outer end of the open loop and (b) a radially-inner-most point of the open loop, measured perpendicular to the central longitudinal axis, is equal to at least 30% of the greatest lateral dimension.

Inventive concept 154. The apparatus according to inventive concept 143, wherein a cross-sectional area of the wire is at least 0.09 mm2.

Inventive concept 155. The apparatus according to inventive concept 154, wherein the cross-sectional area of the wire is no more than 2.9 mm2.

Inventive concept 156. The apparatus according to inventive concept 143, wherein the flexible elongate tension member comprises Nitinol.

Inventive concept 157. The apparatus according to inventive concept 143, wherein (a) a site distance between the site and the distal end of the shaft is greater than (b) a center-point distance between the center point and the distal end of the shaft when the tissue anchor is unconstrained by the deployment tool.

Inventive concept 158. The apparatus according to inventive concept 157, wherein the site distance equals at least 150% of the center-point distance when the tissue anchor is unconstrained by the deployment tool.

Inventive concept 159. The apparatus according to inventive concept 158, wherein the site distance equals at least 175% of the center-point distance when the tissue anchor is unconstrained by the deployment tool.

Inventive concept 160. The apparatus according to inventive concept 143, wherein the longitudinal segment of the proximal portion of the flexible elongate tension member is coupled in sliding communication with the at least a portion of the shaft when the tissue anchor is unconstrained by the deployment tool.

Inventive concept 161. The apparatus according to inventive concept 160, wherein the tissue anchor comprises one or more annular elements, which are disposed around the at least a portion of the shaft, and couple the flexible elongate tension member in the sliding communication with the at least a portion of the shaft when the tissue anchor is unconstrained by the deployment tool.

Inventive concept 162. The apparatus according to inventive concept 143, wherein the flexible elongate tension member is not fixed to any portion of the open loop beyond 2 mm from the site on the open loop, measured when the tissue anchor is unconstrained by the deployment tool.

Inventive concept 163. The apparatus according to inventive concept 143, wherein, when the tissue anchor is unconstrained by the deployment tool:
the open loop has a greatest lateral dimension, measured perpendicular to the central longitudinal axis, and
the flexible elongate tension member is not fixed to any portion of the open loop beyond a distance from the site on the open loop, wherein the distance equals 30% of the greatest lateral dimension.

Inventive concept 164. The apparatus according to inventive concept 143, wherein the flexible elongate tension member is fixed to the open loop only at the site on the open loop.

Inventive concept 165. The apparatus according to inventive concept 143, wherein, when the tissue anchor is unconstrained by the deployment tool:
the open loop has a greatest lateral dimension, measured perpendicular to the central longitudinal axis, and
the at least a portion of the open loop crossed by the crossing portion has a length that equals at least 50% of the greatest lateral dimension.

Inventive concept 166. The apparatus according to inventive concept 165, wherein the length of the at least a portion of the open loop crossed by the crossing portion equals at least 75% of the greatest lateral dimension when the tissue anchor is unconstrained by the deployment tool.

Inventive concept 167. The apparatus according to inventive concept 166, wherein the length of the at least a portion of the open loop crossed by the crossing portion equals at least 90% of the greatest lateral dimension when the tissue anchor is unconstrained by the deployment tool.

Inventive concept 168. The apparatus according to inventive concept 143, wherein the apparatus further comprises one or more tethers, which are fixed to the flexible elongate tension member.

Inventive concept 169. The apparatus according to inventive concept 143,
wherein the tissue anchor is a first tissue anchor, and
wherein the apparatus further comprises:
a second tissue anchor, which is separate and distinct from the first tissue anchor; and
one or more tethers, which are configured to couple (a) the flexible elongate tension member to (b) the second tissue anchor.

Inventive concept 170. The apparatus according to inventive concept 169, wherein the one or more tethers are fixed to (a) the flexible elongate tension member and (b) the second tissue anchor.

Inventive concept 171. The apparatus according to inventive concept 169, wherein the second tissue anchor comprises a helical tissue-coupling element.

Inventive concept 172. The apparatus according to inventive concept 169, wherein the second tissue anchor comprises a stent.

Inventive concept 173. The apparatus according to inventive concept 143,
wherein the tissue anchor is a first tissue anchor, and
wherein the apparatus further comprises a second tissue anchor, which is separate and distinct from the first tissue anchor, and
wherein the flexible elongate tension member is coupled to the second tissue anchor.

Inventive concept 174. The apparatus according to inventive concept 173, wherein the flexible elongate tension member is fixed to the second tissue anchor.

Inventive concept 175. The apparatus according to inventive concept 143,
further comprising a deployment tool, which comprises a sharp distal piercing tip, and which is configured to constrain the tissue-coupling element while delivering the tissue-coupling element through tissue, and
wherein, when the tissue-coupling element is constrained by the deployment tool, a longitudinal portion of the flexible elongate tension member runs alongside a portion of the wire.

Inventive concept 176. The apparatus according to any one of inventive concepts 129-142, wherein a proximally-facing surface defined by the tissue-coupling element is concave when the tissue anchor is unconstrained by the deployment tool.

Inventive concept 177. The apparatus according to any one of inventive concepts 129-142, wherein a proximally-facing surface defined by the tissue-coupling element is convex when the tissue anchor is unconstrained by the deployment tool.

Inventive concept 178. The apparatus according to any one of inventive concepts 129-142,
wherein the tissue anchor is a first tissue anchor, and wherein the apparatus further comprises:
a second tissue anchor, which is separate and distinct from the first tissue anchor; and
one or more tethers, which are configured to couple (a) the first tissue anchor to (b) the second tissue anchor.

Inventive concept 179. The apparatus according to inventive concept 178, wherein the one or more tethers are fixed to (a) the first tissue anchor and (b) the second tissue anchor.

Inventive concept 180. The apparatus according to inventive concept 178, wherein the second tissue anchor comprises a helical tissue-coupling element.

Inventive concept 181. The apparatus according to inventive concept 178, wherein the second tissue anchor comprises a stent.

There is additionally provided, in accordance with an inventive concept 182 of the present invention, apparatus for delivery in a constrained state within a deployment tool, the apparatus comprising:
a first tissue anchor, which comprises (a) a shaft, (b) a head connected to a proximal portion of the shaft, and (c) a tissue-coupling element, which extends from a distal end of the shaft;
a second tissue anchor, which is separate and distinct from the first tissue anchor;
one or more tethers, which are configured to couple (a) the first tissue anchor to (b) the second tissue anchor,
wherein, when the tissue anchor is unconstrained by the deployment tool:
the shaft has a central longitudinal axis,
the head is coaxial with the central longitudinal axis, and
the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 183. The apparatus according to inventive concept 182, wherein the one or more tethers are configured to couple (a) the head of the first tissue anchor to (b) the second tissue anchor.

Inventive concept 184. The apparatus according to inventive concept 183, wherein the one or more tethers are fixed to (a) the head of the first tissue anchor to (b) the second tissue anchor.

Inventive concept 185. The apparatus according to inventive concept 182, wherein at least 95% of the area of the projection of the tissue-coupling element on the plane would fall within the first angle.

Inventive concept 186. The apparatus according to inventive concept 182, wherein at least 80% of the area of the projection of the tissue-coupling element on the plane would fall within a third angle of 150 degrees in the plane having the vertex at the central longitudinal axis.

Inventive concept 187. The apparatus according to inventive concept 182, wherein an outer portion of the area of the projection of the tissue-coupling element on the plane would fall within all angular positions of a fourth angle of 90 degrees in the plane having the vertex at the central longitudinal axis, which outer portion consists of all points of the area at least 3 mm from the vertex.

Inventive concept 188. The apparatus according to inventive concept 182, wherein a proximally-facing surface defined by the tissue-coupling element is concave when the tissue anchor is unconstrained by the deployment tool.

Inventive concept 189. The apparatus according to inventive concept 182, wherein, when the tissue anchor is unconstrained by the deployment tool:
a greatest longitudinal dimension of the tissue-coupling element, measured parallel to the central longitudinal axis, is between 1 and 5 mm, and
a greatest lateral dimension of the tissue-coupling element, measured perpendicular to the central longitudinal axis, is between 4 and 20 mm.

Inventive concept 190. The apparatus according to inventive concept 189, wherein a ratio of the greatest longitudinal dimension and the greatest lateral dimension is between 1:2 and 1:18 when the tissue anchor is unconstrained by the deployment tool.

Inventive concept 191. The apparatus according to inventive concept 182, wherein the tissue-coupling element has a length of 5 to 60 mm when constrained into a straight configuration.

Inventive concept 192. The apparatus according to inventive concept 182, wherein the tissue-coupling element is non-helical when the tissue anchor is unconstrained by the deployment tool.

Inventive concept 193. The apparatus according to inventive concept 182, wherein the shaft comprises a sealing element.

Inventive concept 194. The apparatus according to inventive concept 182, wherein the central longitudinal axis is straight when the first tissue anchor is unconstrained by the deployment tool.

Inventive concept 195. The apparatus according to inventive concept 182, wherein the shaft is flexible.

Inventive concept 196. The apparatus according to inventive concept 182, wherein the shaft and the tissue-coupling element are integral to one another.

Inventive concept 197. The apparatus according to inventive concept 196, wherein the shaft and the tissue-coupling element comprise a wire.

Inventive concept 198. The apparatus according to any one of inventive concepts 182-197, wherein the tissue-coupling element comprises at least three tines that extend radially outward from the central longitudinal axis in respective directions that are fixed with respect to one another when the tissue anchor is unconstrained by the deployment tool.

Inventive concept 199. The apparatus according to inventive concept 198, wherein tines comprise at least four tines.

Inventive concept 200. The apparatus according to any one of inventive concepts 182-197, wherein the tissue-coupling element comprises a wire.

Inventive concept 201. The apparatus according to inventive concept 200,
wherein the wire is shaped as an open loop having more than one turn, when the tissue anchor is unconstrained by the deployment tool,
wherein the tissue anchor further comprises a flexible elongate tension member, which includes (a) a distal portion that is fixed to a site on the open loop, (b) a proximal portion, which has a longitudinal segment that runs alongside at least a portion of the shaft, and (c) a crossing portion, which (i) is disposed between the distal and the proximal portions along the flexible elongate tension member, and (ii) crosses at least a portion of the open loop when the tissue anchor is unconstrained by the deployment tool, and wherein the tissue anchor is configured to allow relative axial motion between the at least a portion of the shaft and the longitudinal segment of the proximal portion of the flexible elongate tension member when the tissue anchor is unconstrained by the deployment tool.

Inventive concept 202. The apparatus according to inventive concept 201, wherein the head is shaped so as to define a passage in which the proximal portion of the flexible elongate tension member is slidably disposed, wherein the flexible elongate tension member comprises a locking stopper, which is axially fixed to the proximal or the crossing portion of the flexible elongate tension member, and wherein the locking stopper and the passage are sized and shaped such that the size and shape of the passage prevent proximal movement of the locking stopper past the passage.

Inventive concept 203. The apparatus according to inventive concept 201, wherein the open loop is shaped as a spiral when the tissue anchor is unconstrained by the deployment tool.

Inventive concept 204. The apparatus according to inventive concept 203, wherein the spiral is shaped as a three-dimensional spiral when the tissue anchor is unconstrained by the deployment tool.

Inventive concept 205. The apparatus according to inventive concept 203, wherein the spiral is shaped as an elliptical spiral when the tissue anchor is unconstrained by the deployment tool.

Inventive concept 206. The apparatus according to inventive concept 201, wherein the open loop is shaped as a three-dimensional open loop when the tissue anchor is unconstrained by the deployment tool.

Inventive concept 207. The apparatus according to inventive concept 201, wherein, when the tissue anchor is unconstrained by the deployment tool:

the open loop surrounds a center point, and (a) a site distance between the site and the distal end of the shaft is greater than (b) a center-point distance between the center point and the distal end of the shaft when the tissue anchor is unconstrained by the deployment tool.

Inventive concept 208. The apparatus according to inventive concept 207, wherein the site distance equals at least 150% of the center-point distance when the tissue anchor is unconstrained by the deployment tool.

Inventive concept 209. The apparatus according to inventive concept 208, wherein the site distance equals at least 175% of the center-point distance when the tissue anchor is unconstrained by the deployment tool.

Inventive concept 210. The apparatus according to inventive concept 201, wherein the site is on an outermost turn of the open loop when the tissue anchor is unconstrained by the deployment tool.

Inventive concept 211. The apparatus according to inventive concept 201, wherein the site is on a second-to-outermost turn of the open loop when the tissue anchor is unconstrained by the deployment tool.

Inventive concept 212. The apparatus according to inventive concept 201, wherein a radius of the flexible elongate tension member is less than a radius of the wire.

Inventive concept 213. The apparatus according to inventive concept 212, wherein the radius of the flexible elongate tension member is less than 50% of the radius of the wire.

Inventive concept 214. The apparatus according to inventive concept 201, wherein the longitudinal segment of the proximal portion of the flexible elongate tension member is coupled in sliding communication with the at least a portion of the shaft when the tissue anchor is unconstrained by the deployment tool.

Inventive concept 215. The apparatus according to inventive concept 214, wherein the tissue anchor comprises one or more annular elements, which are disposed around the at least a portion of the shaft, and couple the flexible elongate tension member in the sliding communication with the at least a portion of the shaft when the tissue anchor is unconstrained by the deployment tool.

Inventive concept 216. The apparatus according to inventive concept 201, wherein the flexible elongate tension member is not fixed to any portion of the open loop beyond 2 mm from the site on the open loop, measured when the tissue anchor is unconstrained by the deployment tool.

Inventive concept 217. The apparatus according to inventive concept 201, wherein, when the tissue anchor is unconstrained by the deployment tool:

the open loop has a greatest lateral dimension, measured perpendicular to the central longitudinal axis, and the flexible elongate tension member is not fixed to any portion of the open loop beyond a distance from the site on the open loop, wherein the distance equals 30% of the greatest lateral dimension.

Inventive concept 218. The apparatus according to inventive concept 201, wherein the flexible elongate tension member is fixed to the open loop only at the site on the open loop.

Inventive concept 219. The apparatus according to inventive concept 201, wherein, when the tissue anchor is unconstrained by the deployment tool:

the open loop has a greatest lateral dimension, measured perpendicular to the central longitudinal axis, and the at least a portion of the open loop crossed by the crossing portion has a length that equals at least 50% of the greatest lateral dimension.

Inventive concept 220. The apparatus according to inventive concept 219, wherein the length of the at least a portion of the open loop crossed by the crossing portion equals at least 75% of the greatest lateral dimension when the tissue anchor is unconstrained by the deployment tool.

Inventive concept 221. The apparatus according to inventive concept 220, wherein the length of the at least a portion of the open loop crossed by the crossing portion equals at least 90% of the greatest lateral dimension when the tissue anchor is unconstrained by the deployment tool.

Inventive concept 222. The apparatus according to inventive concept 201, wherein, when the tissue anchor is unconstrained by the deployment tool and the flexible elongate tension member is tensioned straight, if the tissue-coupling element and the flexible elongate tension member were to be projected onto the plane that is perpendicular to the central longitudinal axis, an angle between (a) the flexible elongate tension member and (b) a tangent to the open loop at the site would be between 70 and 90 degrees.

Inventive concept 223. The apparatus according to inventive concept 201, wherein the site on the open loop is a first site on the open loop, and wherein, when the tissue anchor is unconstrained by the deployment tool and the flexible elongate tension member is tensioned straight:

the open loop surrounds a center point, the wire extends from the distal end of the shaft at a second site on the open loop, and if the tissue-coupling element and the flexible elongate tension member were to be projected onto the plane that is perpendicular to the central longitudinal axis, a third angle between the first and the second sites, having a vertex at the center point, would be between 130 and 180 degrees.

Inventive concept 224. The apparatus according to inventive concept 223, wherein the third angle is between 150 and 180 degrees.

Inventive concept 225. The apparatus according to inventive concept 224, wherein the third angle is between 170 and 180 degrees.

Inventive concept 226. The apparatus according to inventive concept 223, the second site is at a radially-outer end of the open loop when the tissue anchor is unconstrained by the deployment tool.

Inventive concept 227. The apparatus according to inventive concept 201, wherein the flexible elongate tension member comprises Nitinol.

Inventive concept 228. The apparatus according to inventive concept 201, wherein the one or more tethers are configured to couple (a) the first tissue anchor to (b) the second tissue anchor by coupling (a) the flexible elongate tension member to (b) the second tissue anchor.

Inventive concept 229. The apparatus according to inventive concept 228, wherein the one or more tethers are fixed to (a) the flexible elongate tension member to (b) the second tissue anchor.

Inventive concept 230. The apparatus according to inventive concept 201,
further comprising a deployment tool, which comprises a sharp distal piercing tip, and which is configured to constrain the tissue-coupling element while delivering the tissue-coupling element through tissue, and
wherein, when the tissue-coupling element is constrained by the deployment tool, a longitudinal portion of the flexible elongate tension member runs alongside a portion of the wire.

Inventive concept 231. The apparatus according to inventive concept 200, wherein, when the tissue anchor is unconstrained by the deployment tool:
the wire of the tissue-coupling element is shaped as an open loop around a center point having more than one turn, and
the wire extends from the distal end of the shaft at a radially-outer end of the open loop.

Inventive concept 232. The apparatus according to inventive concept 231, wherein the open loop is shaped as a spiral when the tissue anchor is unconstrained by the deployment tool.

Inventive concept 233. The apparatus according to inventive concept 232, wherein the spiral is shaped as a three-dimensional spiral when the tissue anchor is unconstrained by the deployment tool.

Inventive concept 234. The apparatus according to inventive concept 232, wherein the spiral is shaped as an elliptical spiral when the tissue anchor is unconstrained by the deployment tool.

Inventive concept 235. The apparatus according to inventive concept 231, wherein the open loop is shaped as a three-dimensional open loop when the tissue anchor is unconstrained by the deployment tool.

Inventive concept 236. The apparatus according to inventive concept 231, wherein the wire intersects the center point when the tissue anchor is unconstrained by the deployment tool.

Inventive concept 237. The apparatus according to inventive concept 231, wherein the wire does not intersect the center point when the tissue anchor is unconstrained by the deployment tool.

Inventive concept 238. The apparatus according to inventive concept 231, wherein, when the tissue anchor is unconstrained by the deployment tool:
the open loop has a greatest lateral dimension, measured perpendicular to the central longitudinal axis, and
a distance between (a) the radially-outer end of the open loop and (b) a radially-inner-most point of the open loop, measured perpendicular to the central longitudinal axis, is equal to at least 30% of the greatest lateral dimension.

Inventive concept 239. The apparatus according to inventive concept 231, wherein a proximally-facing surface defined by the tissue-coupling element is convex when the tissue anchor is unconstrained by the deployment tool.

Inventive concept 240. The apparatus according to inventive concept 200, wherein a cross-sectional area of the wire is at least 0.09 mm2.

Inventive concept 241. The apparatus according to inventive concept 240, wherein the cross-sectional area of the wire is no more than 2.9 mm2.

There is yet additionally provided, in accordance with an inventive concept 242 of the present invention, apparatus for delivery in a constrained state within a deployment tool, the apparatus comprising a tissue anchor, which comprises:
a shaft; and
a tissue-coupling element, which extends from a distal end of the shaft, and which comprises three or more tines,
wherein, when the tissue anchor is unconstrained by the deployment tool:
the shaft has a central longitudinal axis,
the tines extend radially outward from the central longitudinal axis in respective directions that are fixed with respect to one another, and
the tissue-coupling element is shaped such that if the tissue-coupling element were to be projected onto a plane that is perpendicular to the central longitudinal axis, at least 80% of an area of projected the tissue-coupling element on the plane would fall within an angle of 210 degrees in the plane having a vertex at the central longitudinal axis.

Inventive concept 243. The apparatus according to inventive concept 242, wherein the three or more tines comprise four or more tines.

Inventive concept 244. The apparatus according to inventive concept 242, wherein at least 80% of the area of the projection of the tissue-coupling element on the plane would fall within a second angle of 180 degrees in the plane having the vertex at the central longitudinal axis.

Inventive concept 245. The apparatus according to inventive concept 242, wherein, when the tissue anchor is unconstrained by the deployment tool:
a greatest longitudinal dimension of the tissue-coupling element, measured parallel to the central longitudinal axis, is between 1 and 5 mm, and
a greatest lateral dimension of the tissue-coupling element, measured perpendicular to the central longitudinal axis, is between 4 and 20 mm.

Inventive concept 246. The apparatus according to inventive concept 242, wherein the shaft comprises a sealing element.

Inventive concept 247. The apparatus according to inventive concept 242, wherein the central longitudinal axis is straight when the tissue anchor is unconstrained by the deployment tool.

Inventive concept 248. The apparatus according to inventive concept 242, wherein the shaft is flexible.

Inventive concept 249. The apparatus according to any one of inventive concepts 242-248, wherein the tines have respective distal ends, each of which does not define a sharp distal tip.

Inventive concept 250. The apparatus according to inventive concept 249, wherein each of the distal ends is blunt.

Inventive concept 251. The apparatus according to any one of inventive concepts 242-248, wherein the tissue-coupling element further comprises one or more membranes that are fixed to and extend between circumferentially-adjacent ones of the tines.

Inventive concept 252. The apparatus according to inventive concept 251, wherein a proximally-facing surface defined by the tissue-coupling element is concave when the tissue anchor is unconstrained by the deployment tool.

Inventive concept 253. The apparatus according to inventive concept 251, wherein the tines are first tines, and wherein the one or more membranes are one or more first membranes that are fixed to and extend between circumferentially-adjacent ones of the first tines, wherein the tissue-coupling element further comprises:

three or more second tines;

one or more second membranes that are fixed to and extend between circumferentially-adjacent ones of the second tines, and are not fixed to any of the first tines, and wherein the first membranes are not fixed to any of the second tines.

Inventive concept 254. The apparatus according to inventive concept 253, wherein the tissue anchor is configured such that the second tines are rotatable with respect to the first tines.

Inventive concept 255. The apparatus according to inventive concept 254, wherein, when the tissue anchor is unconstrained by the deployment tool, the tissue-coupling element is shaped such that:

the first membranes extend circumferentially around the central longitudinal axis between 90 and 180 degrees, and the second membranes extend circumferentially around the central longitudinal axis between 90 and 180 degrees.

Inventive concept 256. The apparatus according to inventive concept 254, wherein, when the tissue anchor is unconstrained by the deployment tool, the tissue-coupling element is shaped such that:

the first membranes extend circumferentially around the central longitudinal axis a first number of degrees, the second membranes extend circumferentially around the central longitudinal axis a second number of degrees, and a sum of the first and second numbers of degrees is between 100 and 350 degrees.

Inventive concept 257. The apparatus according to inventive concept 256, wherein the sum is between 150 and 270 degrees.

Inventive concept 258. The apparatus according to any one of inventive concepts 242-248, wherein the tines are first tines, which are rationally fixed with respect to one another, wherein the tissue-coupling element further comprises three or more second tines, which are rationally fixed with respect to one another, and wherein the tissue anchor is configured such that the second tines are rotatable with respect to the first tines.

Inventive concept 259. The apparatus according to any one of inventive concepts 242-248, wherein the tissue anchor is a first tissue anchor, and wherein the apparatus further comprises:

a second tissue anchor, which is separate and distinct from the first tissue anchor; and one or more tethers, which are configured to couple (a) the first tissue anchor to (b) the second tissue anchor.

Inventive concept 260. The apparatus according to inventive concept 259, wherein the one or more tethers are fixed to (a) the first tissue anchor and (b) the second tissue anchor.

Inventive concept 261. The apparatus according to inventive concept 259, wherein the second tissue anchor comprises a helical tissue-coupling element.

Inventive concept 262. The apparatus according to inventive concept 259, wherein the second tissue anchor comprises a stent.

Inventive concept 263. The apparatus according to any one of inventive concepts 242-248, wherein a proximally-facing surface defined by the tissue-coupling element is concave when the tissue anchor is unconstrained by the deployment tool.

There is also provided, in accordance with an inventive concept 264 of the present invention, a method comprising:

providing a tissue anchor that comprises (a) a shaft, (b) a tissue-coupling element, which comprises a wire, and (c) a flexible elongate tension member;

introducing, during a transcatheter procedure, the tissue anchor into a cardiac chamber of a heart of a subject, while the tissue-coupling element is constrained by a deployment tool;

delivering the tissue-coupling element through a wall of the heart; and at least partially releasing the tissue anchor from the deployment tool such that (a) the tissue-coupling element is unconstrained by the deployment tool, (b) the wire of the tissue-coupling element is shaped as an open loop having more than one turn, (c) a distal portion of the flexible elongate tension member is fixed to a site on the open loop, (d) a longitudinal segment of a proximal portion of the flexible elongate tension member runs alongside at least a portion of the shaft, (e) a crossing portion of the flexible elongate tension member, disposed between the distal and the proximal portions along the flexible elongate tension member, crosses at least a portion of the open loop, and (f) the tissue anchor allows relative axial motion between the at least a portion of the shaft and the longitudinal segment of the proximal portion of the flexible elongate tension member.

Inventive concept 265. The method according to inventive concept 264, further comprising, after delivering the tissue-coupling element through the wall of the heart, at least partially compressing the open loop by applying tension to the flexible elongate tension member.

Inventive concept 266. The method according to inventive concept 264, further comprising, after delivering the tissue-coupling element through the wall of the heart, at least partially compressing the open loop and pulling the tissue-coupling element against an external surface of the heart, by applying tension to the flexible elongate tension member.

Inventive concept 267. The method according to inventive concept 264, wherein the tissue anchor comprises a head connected to a proximal portion of the shaft, wherein the head is shaped so as to define a passage in which the proximal portion of the flexible elongate tension member is slidably disposed, wherein the flexible elongate tension member comprises a locking stopper, which is axially fixed to the proximal or the crossing portion of the flexible elongate tension member, wherein the locking stopper and the passage are sized and shaped such that the size and shape of the passage prevent proximal movement of the locking stopper past the passage, and wherein the method further comprises, after delivering the tissue-coupling element through the wall of the heart:
  at least partially compressing the open loop by applying tension to the flexible elongate tension member; and
  after the passage prevents proximal movement of the locking stopper past the passage, applying, to the flexible elongate tension member, additional tension that does not further compress the open loop.

Inventive concept 268. The method according to inventive concept 267, wherein the locking stopper is axially fixed to the proximal or the crossing portion of the flexible elongate tension member at a distance of between 7 and 22 mm from the site on the open loop.

Inventive concept 269. The method according to inventive concept 267, wherein, if the tissue-coupling element were straightened in an elongated configuration, the locking stopper would be a distance of between 7 and 12 mm from the passage.

Inventive concept 270. The method according to inventive concept 264, wherein the open loop is shaped as a spiral when the tissue anchor is unconstrained by the deployment tool.

Inventive concept 271. The method according to inventive concept 270, wherein the spiral is shaped as a three-dimensional spiral when the tissue anchor is unconstrained by the deployment tool.

Inventive concept 272. The method according to inventive concept 270, wherein the spiral is shaped as an elliptical spiral when the tissue anchor is unconstrained by the deployment tool.

Inventive concept 273. The method according to inventive concept 264, wherein the open loop is shaped as a three-dimensional open loop when the tissue anchor is unconstrained by the deployment tool.

Inventive concept 274. The method according to inventive concept 273, wherein, when the tissue anchor is unconstrained by the deployment tool:
  a greatest longitudinal dimension of the three-dimensional open loop, measured in parallel to a central longitudinal axis of the shaft, is between 1 and 5 mm, and
  a greatest lateral dimension of the three-dimensional open loop, measured perpendicular to the central longitudinal axis, is between 4 and 20 mm.

Inventive concept 275. The method according to inventive concept 264, further comprising, after delivering the tissue-coupling element through the wall of the heart:
  ascertaining whether the tissue-coupling element overlies a coronary blood vessel; and
  if the tissue-coupling element overlies the coronary blood vessel, rotating the tissue anchor until the tissue-coupling element no longer overlies the coronary blood vessel.

Inventive concept 276. The method according to inventive concept 264, further comprising, after delivering the tissue-coupling element through the wall of the heart:
  rotating the tissue anchor by rotating the shaft; and
  bringing the tissue-coupling element into contact with an external surface of the heart by applying tension to the flexible elongate tension member.

Inventive concept 277. The method according to inventive concept 276, wherein bringing the tissue-coupling element into contact with the external surface of the heart comprises bringing the tissue-coupling element into contact with the external surface of the heart without applying any tension to the shaft.

Inventive concept 278. The method according to inventive concept 264, wherein the site is on an outermost turn of the open loop when the tissue anchor is unconstrained by the deployment tool.

Inventive concept 279. The method according to inventive concept 264, wherein the site is on a second-to-outermost turn of the open loop when the tissue anchor is unconstrained by the deployment tool.

Inventive concept 280. The method according to inventive concept 264, wherein a radius of the flexible elongate tension member is less than a radius of the wire.

Inventive concept 281. The method according to inventive concept 280, wherein the radius of the flexible elongate tension member is less than 50% of the radius of the wire.

Inventive concept 282. The method according to inventive concept 264, wherein, when the tissue anchor is unconstrained by the deployment tool and the flexible elongate tension member is tensioned straight, if the tissue-coupling element and the flexible elongate tension member were to be projected onto a plane that is perpendicular to a central longitudinal axis of the shaft, an angle between (a) the flexible elongate tension member and (b) a tangent to the open loop at the site would be between 70 and 90 degrees.

Inventive concept 283. The method according to inventive concept 264, wherein, when the tissue anchor is unconstrained by the deployment tool:
  the open loop is shaped so as to define an outermost turn and a second-to-outermost at least partial turn, and
  the outermost turn at least partially overlaps the second-to-outermost at least partial turn.

Inventive concept 284. The method according to inventive concept 264, wherein, when the tissue anchor is unconstrained by the deployment tool, the open loop is shaped so as to define one or more curved segments and one or more straight segments.

Inventive concept 285. The method according to inventive concept 284, wherein, when the tissue anchor is unconstrained by the deployment tool, the open loop is shaped so as to define the one or more curved segments and two or more straight segments.

Inventive concept 286. The method according to inventive concept 264, wherein the site on the open loop is a first site on the open loop, and wherein, when the tissue anchor is unconstrained by the deployment tool and the flexible elongate tension member is tensioned straight:
  the open loop surrounds a center point,
  the wire extends from the distal end of the shaft at a second site on the open loop, and
  if the tissue-coupling element and the flexible elongate tension member were to be projected onto a plane that is perpendicular to a central longitudinal axis of the shaft, an angle between the first and the second sites, having a vertex at the center point, would be between 130 and 180 degrees.

Inventive concept 287. The method according to inventive concept 286, wherein the angle is between 150 and 180 degrees.

Inventive concept 288. The method according to inventive concept 287, wherein the angle is between 170 and 180 degrees.

Inventive concept 289. The method according to inventive concept 286, the second site is at a radially-outer end of the open loop when the tissue anchor is unconstrained by the deployment tool.

Inventive concept 290. The method according to inventive concept 264, wherein, when the tissue anchor is unconstrained by the deployment tool:
the open loop has a greatest lateral dimension, measured perpendicular to a central longitudinal axis of the shaft, and
a distance between (a) a radially-outer end of the open loop and (b) a radially-inner-most point of the open loop, measured perpendicular to the central longitudinal axis, is equal to at least 30% of the greatest lateral dimension.

Inventive concept 291. The method according to inventive concept 290, wherein a ratio of the greatest longitudinal dimension and the greatest lateral dimension is between 1:2 and 1:18 when the tissue anchor is unconstrained by the deployment tool.

Inventive concept 292. The method according to inventive concept 264, wherein the shaft comprises a sealing element.

Inventive concept 293. The method according to inventive concept 264, wherein the shaft has a central longitudinal axis that is straight when the tissue anchor is unconstrained by the deployment tool.

Inventive concept 294. The method according to inventive concept 264, wherein the shaft is flexible.

Inventive concept 295. The method according to inventive concept 264, wherein the shaft and the tissue-coupling element are integral to one another.

Inventive concept 296. The method according to inventive concept 264, wherein a cross-sectional area of the wire is at least 0.09 mm2.

Inventive concept 297. The method according to inventive concept 296, wherein the cross-sectional area of the wire is no more than 2.9 mm2.

Inventive concept 298. The method according to inventive concept 264, wherein the flexible elongate tension member comprises Nitinol.

Inventive concept 299. The method according to inventive concept 264, wherein, when the tissue anchor is unconstrained by the deployment tool:
the open loop surrounds a center point, and
(a) a site distance between the site and the distal end of the shaft is greater than (b) a center-point distance between the center point and the distal end of the shaft when the tissue anchor is unconstrained by the deployment tool.

Inventive concept 300. The method according to inventive concept 299, wherein the site distance equals at least 150% of the center-point distance when the tissue anchor is unconstrained by the deployment tool.

Inventive concept 301. The method according to inventive concept 300, wherein the site distance equals at least 175% of the center-point distance when the tissue anchor is unconstrained by the deployment tool.

Inventive concept 302. The method according to inventive concept 264, wherein the longitudinal segment of the proximal portion of the flexible elongate tension member is coupled in sliding communication with the at least a portion of the shaft when the tissue anchor is unconstrained by the deployment tool.

Inventive concept 303. The method according to inventive concept 302, wherein the tissue anchor comprises one or more annular elements, which are disposed around the at least a portion of the shaft, and couple the flexible elongate tension member in the sliding communication with the at least a portion of the shaft when the tissue anchor is unconstrained by the deployment tool.

Inventive concept 304. The method according to inventive concept 264, wherein the flexible elongate tension member is not fixed to any portion of the open loop beyond 2 mm from the site on the open loop, measured when the tissue anchor is unconstrained by the deployment tool.

Inventive concept 305. The method according to inventive concept 264, wherein, when the tissue anchor is unconstrained by the deployment tool:
the open loop has a greatest lateral dimension, measured perpendicular to a central longitudinal axis of the shaft, and
the flexible elongate tension member is not fixed to any portion of the open loop beyond a distance from the site on the open loop, wherein the distance equals 30% of the greatest lateral dimension.

Inventive concept 306. The method according to inventive concept 264, wherein the flexible elongate tension member is fixed to the open loop only at the site on the open loop.

Inventive concept 307. The method according to inventive concept 264, wherein, when the tissue anchor is unconstrained by the deployment tool:
the open loop has a greatest lateral dimension, measured perpendicular to a central longitudinal axis of the shaft, and
the at least a portion of the open loop crossed by the crossing portion has a length that equals at least 50% of the greatest lateral dimension.

Inventive concept 308. The method according to inventive concept 307, wherein the length of the at least a portion of the open loop crossed by the crossing portion equals at least 75% of the greatest lateral dimension when the tissue anchor is unconstrained by the deployment tool.

Inventive concept 309. The method according to inventive concept 308, wherein the length of the at least a portion of the open loop crossed by the crossing portion equals at least 90% of the greatest lateral dimension when the tissue anchor is unconstrained by the deployment tool.

Inventive concept 310. The method according to inventive concept 264, wherein the wire extends from a distal end of the shaft at a radially-outer end of the open loop when the tissue anchor is unconstrained by the deployment tool.

Inventive concept 311. The method according to inventive concept 310, wherein, when the tissue anchor is unconstrained by the deployment tool, the open loop surrounds a center point, and the wire intersects the center point.

Inventive concept 312. The method according to inventive concept 310, wherein, when the tissue anchor is unconstrained by the deployment tool, the open loop surrounds a center point, and the wire does not intersect the center point.

Inventive concept 313. The method according to inventive concept 264, wherein the wire extends from a distal end of the shaft at a radially-inner end of the open loop when the tissue anchor is unconstrained by the deployment tool.

Inventive concept 314. The method according to inventive concept 313,
wherein the flexible elongate tension member is a first flexible elongate tension member, the distal portion is a first distal portion, the proximal portion is a first proximal portion, the crossing portion is a first crossing portion, the site is a first site, the at least a portion of the open loop is at least a first portion of the open loop, and the longitudinal segment of the flexible elongate tension member is a first longitudinal segment of the first flexible elongate tension member,
wherein the tissue anchor comprises a second flexible elongate tension member, and
wherein at least partially releasing the tissue anchor comprises at least partially releasing the tissue anchor such that (a) a second distal portion of the second flexible elongate tension member is fixed to a second site on the open loop, different from the first site, (b) a second longitudinal segment of a second proximal portion of the second flexible elongate tension member runs alongside at least a portion of the shaft, and (c) a second crossing portion of the second flexible elongate tension member, disposed between the second distal and the second proximal portions along the second flexible elongate tension member, crosses at least a second portion of the open loop when the tissue anchor is unconstrained by the deployment tool, and (d) the tissue anchor allows relative axial motion between the at least a portion of the shaft and the second longitudinal segment of the second proximal portion of the second flexible elongate tension member.

Inventive concept 315. The method according to inventive concept 314, wherein the first proximal portion of the first flexible elongate tension member and the second proximal portion of the second flexible elongate tension member join one another.

Inventive concept 316. The method according to inventive concept 264, wherein a proximally-facing surface defined by the tissue-coupling element is concave when the tissue anchor is unconstrained by the deployment tool.

Inventive concept 317. The method according to inventive concept 264, wherein a proximally-facing surface defined by the tissue-coupling element is convex when the tissue anchor is unconstrained by the deployment tool.

Inventive concept 318. The method according to inventive concept 264, wherein one or more tethers are fixed to the flexible elongate tension member.

Inventive concept 319. The method according to inventive concept 264,
wherein the tissue anchor is a first tissue anchor, and
wherein the method further comprises:
implanting a second tissue anchor in the subject, which second tissue anchor is separate and distinct from the first tissue anchor; and
facilitating repair of an atrioventricular valve of the subject by applying tension to one or more tethers that couple the flexible elongate tension member to the second tissue anchor.

Inventive concept 320. The method according to inventive concept 319, further comprising, before applying the tension, coupling the flexible elongate tension member to the second tissue anchor using the one or more tethers.

Inventive concept 321. The method according to inventive concept 319, wherein the one or more tethers are fixed to (a) the flexible elongate tension member and (b) the second tissue anchor.

Inventive concept 322. The method according to inventive concept 319, wherein the one or more tethers are (a) fixed to the second tissue anchor and (b) not fixed to the shaft of the first tissue anchor.

Inventive concept 323. The method according to inventive concept 319, wherein the second tissue anchor comprises a helical tissue-coupling element.

Inventive concept 324. The method according to inventive concept 319, wherein the second tissue anchor comprises a stent.

Inventive concept 325. The method according to inventive concept 264,
wherein the tissue anchor is a first tissue anchor, and
wherein the method further comprises:
implanting a second tissue anchor in the subject, which second tissue anchor is (a) separate and distinct from the first tissue anchor, and (b) coupled to the flexible elongate tension member; and
facilitating repair of an atrioventricular valve of the subject by applying tension to flexible elongate tension member.

Inventive concept 326. The method according to inventive concept 325, wherein the flexible elongate tension member is fixed to the second tissue anchor.

Inventive concept 327. The method according to inventive concept 264, wherein introducing comprises introducing the tissue anchor while the tissue-coupling element is constrained by the deployment tool, and a longitudinal portion of the flexible elongate tension member runs alongside a portion of the wire.

There is further provided, in accordance with an inventive concept 328 of the present invention, a method comprising:
providing a tissue anchor that comprises (a) a shaft and (b) a tissue-coupling element, which comprises a wire;
introducing, during a transcatheter procedure, the tissue anchor into a cardiac chamber of a heart of a subject, while the tissue-coupling element is constrained by a deployment tool;
delivering the tissue-coupling element through a wall of the heart; and
at least partially releasing the tissue anchor from the deployment tool such that (a) the tissue-coupling element is unconstrained by the deployment tool by the deployment tool, (b) the wire of the tissue-coupling element is shaped as an open loop having more than one turn around a center point, and (c) the wire extends from a distal end of the shaft at a radially-outer end of the open loop.

Inventive concept 329. The method according to inventive concept 328, wherein the open loop is shaped as a spiral when the tissue anchor is unconstrained by the deployment tool.

Inventive concept 330. The method according to inventive concept 329, wherein the spiral is shaped as a three-dimensional spiral when the tissue anchor is unconstrained by the deployment tool.

Inventive concept 331. The method according to inventive concept 329, wherein the spiral is shaped as an elliptical spiral when the tissue anchor is unconstrained by the deployment tool.

Inventive concept 332. The method according to inventive concept 328, wherein the open loop is shaped as a three-dimensional open loop when the tissue anchor is unconstrained by the deployment tool.

Inventive concept 333. The method according to inventive concept 332, wherein, when the tissue anchor is unconstrained by the deployment tool:
a greatest longitudinal dimension of the three-dimensional open loop, measured in parallel to a central longitudinal axis of the shaft, is between 1 and 5 mm, and
a greatest lateral dimension of the three-dimensional open loop, measured perpendicular to the central longitudinal axis, is between 4 and 20 mm.

Inventive concept 334. The method according to inventive concept 328, further comprising, after delivering the tissue-coupling element through the wall of the heart:
ascertaining whether the tissue-coupling element overlies a coronary blood vessel; and
if the tissue-coupling element overlies the coronary blood vessel, rotating the tissue anchor until the tissue-coupling element no longer overlies the coronary blood vessel.

Inventive concept 335. The method according to inventive concept 328, further comprising, after delivering the tissue-coupling element through the wall of the heart, rotating the tissue anchor and bringing the tissue-coupling element into contact with an external surface of the heart.

Inventive concept 336. The method according to inventive concept 328, wherein the wire intersects the center point when the tissue anchor is unconstrained by the deployment tool.

Inventive concept 337. The method according to inventive concept 328, wherein the wire does not intersect the center point when the tissue anchor is unconstrained by the deployment tool.

Inventive concept 338. The method according to inventive concept 328, wherein, when the tissue anchor is unconstrained by the deployment tool:

the open loop has a greatest lateral dimension, measured perpendicular to a central longitudinal axis of the shaft, and a distance between (a) the radially-outer end of the open loop and (b) a radially-inner-most point of the open loop, measured perpendicular to the central longitudinal axis, is equal to at least 30% of the greatest lateral dimension.

Inventive concept 339. The method according to inventive concept 333, wherein a ratio of the greatest longitudinal dimension and the greatest lateral dimension is between 1:2 and 1:18 when the tissue anchor is unconstrained by the deployment tool.

Inventive concept 340. The method according to inventive concept 328, wherein the tissue anchor further comprises a flexible elongate tension member, which comprises (a) a distal portion that is fixed to a site on the open loop, (b) a proximal portion, which has a longitudinal segment that runs alongside at least a portion of the shaft, and (c) a crossing portion, which (i) is disposed between the distal and the proximal portions along the flexible elongate tension member, and (ii) crosses at least a portion of the open loop when the tissue anchor is unconstrained by the deployment tool, and wherein the tissue anchor is configured to allow relative axial motion between the at least a portion of the shaft and the longitudinal segment of the proximal portion of the flexible elongate tension member when the tissue anchor is unconstrained by the deployment tool.

Inventive concept 341. The method according to inventive concept 340, further comprising, after delivering the tissue-coupling element through the wall of the heart:

rotating the tissue anchor by rotating the shaft; and bringing the tissue-coupling element into contact with an external surface of the heart by applying tension to the flexible elongate tension member.

Inventive concept 342. The method according to inventive concept 341, wherein bringing the tissue-coupling element into contact with the external surface of the heart comprises bringing the tissue-coupling element into contact with the external surface of the heart without applying any tension to the shaft.

Inventive concept 343. The method according to inventive concept 340, wherein the longitudinal segment of the proximal portion of the flexible elongate tension member is coupled in sliding communication with the at least a portion of the shaft when the tissue anchor is unconstrained by the deployment tool.

Inventive concept 344. The method according to inventive concept 343, wherein the tissue anchor comprises one or more annular elements, which are disposed around the at least a portion of the shaft, and couple the flexible elongate tension member in the sliding communication with the at least a portion of the shaft when the tissue anchor is unconstrained by the deployment tool.

Inventive concept 345. The method according to inventive concept 340, wherein the site is on an outermost turn of the open loop when the tissue anchor is unconstrained by the deployment tool.

Inventive concept 346. The method according to inventive concept 340, wherein the site is on a second-to-outermost turn of the open loop when the tissue anchor is unconstrained by the deployment tool.

Inventive concept 347. The method according to inventive concept 340, wherein a radius of the flexible elongate tension member is less than a radius of the wire.

Inventive concept 348. The method according to inventive concept 347, wherein the radius of the flexible elongate tension member is less than 50% of the radius of the wire.

Inventive concept 349. The method according to inventive concept 340, wherein, when the tissue anchor is unconstrained by the deployment tool and the flexible elongate tension member is tensioned straight, if the tissue-coupling element and the flexible elongate tension member were to be projected onto a plane that is perpendicular to a central longitudinal axis of the shaft, an angle between (a) the flexible elongate tension member and (b) a tangent to the open loop at the site would be between 70 and 90 degrees.

Inventive concept 350. The method according to inventive concept 340, wherein the site on the open loop is a first site on the open loop, and wherein, when the tissue anchor is unconstrained by the deployment tool and the flexible elongate tension member is tensioned straight:

the wire extends from the distal end of the shaft at a second site on the open loop, and if the tissue-coupling element and the flexible elongate tension member were to be projected onto a plane that is perpendicular to a central longitudinal axis of the shaft, an angle between the first and the second sites, having a vertex at the center point, would be between 130 and 180 degrees.

Inventive concept 351. The method according to inventive concept 350, wherein the angle is between 150 and 180 degrees.

Inventive concept 352. The method according to inventive concept 351, wherein the angle is between 170 and 180 degrees.

Inventive concept 353. The method according to inventive concept 350, the second site is at a radially-outer end of the open loop when the tissue anchor is unconstrained by the deployment tool.

Inventive concept 354. The method according to inventive concept 340, wherein, when the tissue anchor is unconstrained by the deployment tool:

the open loop has a greatest lateral dimension, measured perpendicular to a central longitudinal axis of the shaft, and a distance between (a) a radially-outer end of the open loop and (b) a radially-inner-most point of the open loop, measured perpendicular to the central longitudinal axis, is equal to at least 30% of the greatest lateral dimension.

Inventive concept 355. The method according to inventive concept 340, wherein a cross-sectional area of the wire is at least 0.09 mm2.

Inventive concept 356. The method according to inventive concept 355, wherein the cross-sectional area of the wire is no more than 2.9 mm2.

Inventive concept 357. The method according to inventive concept 340, wherein the flexible elongate tension member comprises Nitinol.

Inventive concept 358. The method according to inventive concept 340, wherein (a) a site distance between the site and the distal end of the shaft is greater than (b) a center-point distance between the center point and the distal end of the shaft when the tissue anchor is unconstrained by the deployment tool.

Inventive concept 359. The method according to inventive concept 358, wherein the site distance equals at least 150% of the center-point distance when the tissue anchor is unconstrained by the deployment tool.

Inventive concept 360. The method according to inventive concept 359, wherein the site distance equals at least 175% of the center-point distance when the tissue anchor is unconstrained by the deployment tool.

Inventive concept 361. The method according to inventive concept 340, wherein the flexible elongate tension member is not fixed to any portion of the open loop beyond 2 mm from the site on the open loop, measured when the tissue anchor is unconstrained by the deployment tool.

Inventive concept 362. The method according to inventive concept 340, wherein, when the tissue anchor is unconstrained by the deployment tool:
the open loop has a greatest lateral dimension, measured perpendicular to a central longitudinal axis of the shaft, and
the flexible elongate tension member is not fixed to any portion of the open loop beyond a distance from the site on the open loop, wherein the distance equals 30% of the greatest lateral dimension.

Inventive concept 363. The method according to inventive concept 340, wherein the flexible elongate tension member is fixed to the open loop only at the site on the open loop.

Inventive concept 364. The method according to inventive concept 340, wherein, when the tissue anchor is unconstrained by the deployment tool:
the open loop has a greatest lateral dimension, measured perpendicular to a central longitudinal axis of the shaft, and
the at least a portion of the open loop crossed by the crossing portion has a length that equals at least 50% of the greatest lateral dimension.

Inventive concept 365. The method according to inventive concept 364, wherein the length of the at least a portion of the open loop crossed by the crossing portion equals at least 75% of the greatest lateral dimension when the tissue anchor is unconstrained by the deployment tool.

Inventive concept 366. The method according to inventive concept 365, wherein the length of the at least a portion of the open loop crossed by the crossing portion equals at least 90% of the greatest lateral dimension when the tissue anchor is unconstrained by the deployment tool.

Inventive concept 367. The method according to inventive concept 340, wherein one or more tethers are fixed to the flexible elongate tension member.

Inventive concept 368. The method according to inventive concept 340,
wherein the tissue anchor is a first tissue anchor, and
wherein the method further comprises:
implanting a second tissue anchor in the subject, which second tissue anchor is separate and distinct from the first tissue anchor; and
facilitating repair of an atrioventricular valve of the subject by applying tension to one or more tethers that couple the flexible elongate tension member to the second tissue anchor.

Inventive concept 369. The method according to inventive concept 368, further comprising, before applying the tension, coupling the flexible elongate tension member to the second tissue anchor using the one or more tethers.

Inventive concept 370. The method according to inventive concept 368, wherein the one or more tethers are fixed to (a) the flexible elongate tension member and (b) the second tissue anchor.

Inventive concept 371. The method according to inventive concept 368, wherein the second tissue anchor comprises a helical tissue-coupling element.

Inventive concept 372. The method according to inventive concept 368, wherein the second tissue anchor comprises a stent.

Inventive concept 373. The method according to inventive concept 340,
wherein the tissue anchor is a first tissue anchor, and
wherein the method further comprises:
implanting a second tissue anchor in the subject, which second tissue anchor is (a) separate and distinct from the first tissue anchor, and (b) coupled to the flexible elongate tension member; and
facilitating repair of an atrioventricular valve of the subject by applying tension to flexible elongate tension member.

Inventive concept 374. The method according to inventive concept 373, wherein the flexible elongate tension member is fixed to the second tissue anchor.

Inventive concept 375. The method according to inventive concept 340, wherein introducing comprises introducing the tissue anchor while the tissue-coupling element is constrained by the deployment tool, and a longitudinal portion of the flexible elongate tension member runs alongside a portion of the wire.

Inventive concept 376. The method according to inventive concept 328, wherein a proximally-facing surface defined by the tissue-coupling element is concave when the tissue anchor is unconstrained by the deployment tool.

Inventive concept 377. The method according to inventive concept 328,
wherein a proximally-facing surface defined by the tissue-coupling element is convex when the tissue anchor is unconstrained by the deployment tool, and
wherein the method further comprises bringing the proximally-facing surface defined by the tissue-coupling element into contact with an external surface of the heart.

Inventive concept 378. The method according to inventive concept 328,
wherein the tissue anchor is a first tissue anchor, and
wherein the method further comprises:
implanting a second tissue anchor in the subject, which second tissue anchor is separate and distinct from the first tissue anchor; and
facilitating repair of an atrioventricular valve of the subject by applying tension to one or more tethers that couple the first tissue anchor to the second tissue anchor.

Inventive concept 379. The method according to inventive concept 378, further comprising, before applying the tension, coupling the first tissue anchor to the second tissue anchor using the one or more tethers.

Inventive concept 380. The method according to inventive concept 378, wherein one of the one or more tethers is fixed to one of (a) the first tissue anchor and (b) the second tissue anchor.

Inventive concept 381. The method according to inventive concept 378, wherein the second tissue anchor comprises a helical tissue-coupling element.

Inventive concept 382. The method according to inventive concept 378, wherein the second tissue anchor comprises a stent.

Inventive concept 383. The method according to inventive concept 328, wherein the shaft comprises a sealing element.

Inventive concept 384. The method according to inventive concept 328, wherein a central longitudinal of the shaft axis is straight when the tissue anchor is unconstrained by the deployment tool.

Inventive concept 385. The method according to inventive concept 328, wherein the shaft is flexible.

Inventive concept 386. The method according to inventive concept 328, wherein the shaft and the tissue-coupling element are integral to one another.

Inventive concept 387. The method according to inventive concept 328, wherein delivering the tissue-coupling element through the wall of the heart comprises advancing a sharp distal piercing tip of the deployment tool through the wall.

There is still further provided, in accordance with an inventive concept 388 of the present invention, a method comprising:

providing a tissue anchor that comprises (a) a shaft, (b) a head connected to a proximal portion of the shaft, and (c) a tissue-coupling element, which extends from a distal end of the shaft;

introducing, during a transcatheter procedure, the tissue anchor into a cardiac chamber of a heart of a subject, while the tissue-coupling element is constrained by a deployment tool;

delivering the tissue-coupling element through a wall of the heart by advancing a sharp distal piercing tip of the deployment tool through the wall; and at least partially releasing the tissue anchor from the deployment tool such that (a) the tissue-coupling element is unconstrained by the deployment tool, (b) the head is coaxial with a central longitudinal axis of the shaft, and (c) the tissue-coupling element is shaped such that if the tissue-coupling element were to be projected onto a plane that is perpendicular to the central longitudinal axis, (i) at least 80% of an area of a projection of the tissue-coupling element on the plane would fall within a first angle of 180 degrees in the plane having a vertex at the central longitudinal axis, and (ii) the area would partially overlap, at least 3 mm from the vertex, both rays of a second angle of between 45 and 180 degrees in the plane having the vertex at the central longitudinal axis.

Inventive concept 389. The method according to inventive concept 388, further comprising, after delivering the tissue-coupling element through the wall of the heart:

ascertaining whether the tissue-coupling element overlies a coronary blood vessel; and if the tissue-coupling element overlies the coronary blood vessel, rotating the tissue anchor until the tissue-coupling element no longer overlies the coronary blood vessel.

Inventive concept 390. The method according to inventive concept 388, further comprising, after delivering the tissue-coupling element through the wall of the heart, rotating the tissue anchor and bringing the tissue-coupling element into contact with an external surface of the heart.

Inventive concept 391. The method according to inventive concept 390, wherein introducing the tissue anchor into the cardiac chamber comprises introducing the tissue anchor into an atrium of the heart, and wherein bringing the tissue-coupling element into contact with the external surface of the heart comprises bringing the tissue-coupling element into contact with an external surface of a ventricle of the heart.

Inventive concept 392. The method according to inventive concept 391, wherein introducing the tissue anchor into the atrium comprises introducing the tissue anchor into a right atrium, and wherein bringing the tissue-coupling element into contact with the external surface of the ventricle comprises bringing the tissue-coupling element into contact with an external surface of a right ventricle.

Inventive concept 393. The method according to inventive concept 388, wherein at least 95% of the area of the projection of the tissue-coupling element on the plane would fall within the first angle.

Inventive concept 394. The method according to inventive concept 388, wherein at least 80% of the area of the projection of the tissue-coupling element on the plane would fall within a second angle of 150 degrees in the plane having the vertex at the central longitudinal axis.

Inventive concept 395. The method according to inventive concept 388, wherein an outer portion of the area of the projection of the tissue-coupling element on the plane would fall within all angular positions of a second angle of 90 degrees in the plane having the vertex at the central longitudinal axis, which outer portion consists of all points of the area at least 3 mm from the vertex.

Inventive concept 396. The method according to inventive concept 388, wherein a proximally-facing surface defined by the tissue-coupling element is concave when the tissue anchor is unconstrained by the deployment tool.

Inventive concept 397. The method according to inventive concept 388, wherein, when the tissue anchor is unconstrained by the deployment tool:

a greatest longitudinal dimension of the tissue-coupling element, measured parallel to the central longitudinal axis, is between 1 and 5 mm, and a greatest lateral dimension of the tissue-coupling element, measured perpendicular to the central longitudinal axis, is between 4 and 20 mm.

Inventive concept 398. The method according to inventive concept 397, wherein a ratio of the greatest longitudinal dimension and the greatest lateral dimension is between 1:2 and 1:18 when the tissue anchor is unconstrained by the deployment tool.

Inventive concept 399. The method according to inventive concept 388, wherein the tissue-coupling element has a length of 5 to 60 mm when constrained into a straight configuration.

Inventive concept 400. The method according to inventive concept 388, wherein the tissue-coupling element is non-helical when the tissue anchor is unconstrained by the deployment tool.

Inventive concept 401. The method according to inventive concept 388, wherein the tissue-coupling element comprises at least three tines that extend radially outward from the central longitudinal axis in respective directions that are fixed with respect to one another when the tissue anchor is unconstrained by the deployment tool.

Inventive concept 402. The method according to inventive concept 401, wherein tines comprise at least four tines.

Inventive concept 403. The method according to inventive concept 388, wherein the shaft comprises a sealing element.

Inventive concept 404. The method according to inventive concept 388, wherein the tissue-coupling element comprises a wire.

Inventive concept 405. The method according to inventive concept 404, wherein the wire is shaped as an open loop having more than one turn when the tissue anchor is unconstrained by the deployment tool, wherein the tissue anchor further comprises a flexible elongate tension member, which includes (a) a distal portion that is fixed to a site on the open loop, (b) a proximal portion, which has a longitudinal segment that runs alongside at least a portion of the shaft, and (c) a crossing portion, which (i) is disposed between the distal and the proximal portions along the flexible elongate tension member, and (ii) crosses at least a portion of the open loop when the tissue anchor is unconstrained by the deployment tool, and wherein the tissue anchor is configured to allow relative axial motion between the at least a portion of the shaft and the longitudinal segment of the proximal portion of the flexible elongate tension member when the tissue anchor is unconstrained by the deployment tool.

Inventive concept 406. The method according to inventive concept 405, wherein the head is shaped so as to define a passage in which the proximal portion of the flexible elongate tension member is slidably disposed, wherein the flexible elongate tension member comprises a locking stopper, which is axially fixed to the proximal or the crossing portion of the flexible elongate tension member, and wherein the locking stopper and the passage are sized and shaped such that the size and shape of the passage prevent proximal movement of the locking stopper past the passage.

Inventive concept 407. The method according to inventive concept 405, wherein the open loop is shaped as a spiral when the tissue anchor is unconstrained by the deployment tool.

Inventive concept 408. The method according to inventive concept 407, wherein the spiral is shaped as a three-dimensional spiral when the tissue anchor is unconstrained by the deployment tool.

Inventive concept 409. The method according to inventive concept 407, wherein the spiral is shaped as an elliptical spiral when the tissue anchor is unconstrained by the deployment tool.

Inventive concept 410. The method according to inventive concept 405, wherein the open loop is shaped as a three-dimensional open loop when the tissue anchor is unconstrained by the deployment tool.

Inventive concept 411. The method according to inventive concept 405, further comprising, after delivering the tissue-coupling element through the wall of the heart:

rotating the tissue anchor by rotating the shaft; and bringing the tissue-coupling element into contact with an external surface of the heart by applying tension to the flexible elongate tension member.

Inventive concept 412. The method according to inventive concept 411, wherein bringing the tissue-coupling element into contact with the external surface of the heart comprises bringing the tissue-coupling element into contact with the external surface of the heart without applying any tension to the shaft.

Inventive concept 413. The method according to inventive concept 411, wherein the longitudinal segment of the proximal portion of the flexible elongate tension member is coupled in sliding communication with the at least a portion of the shaft when the tissue anchor is unconstrained by the deployment tool.

Inventive concept 414. The method according to inventive concept 413, wherein the tissue anchor comprises one or more annular elements, which are disposed around the at least a portion of the shaft, and couple the flexible elongate tension member in the sliding communication with the at least a portion of the shaft when the tissue anchor is unconstrained by the deployment tool.

Inventive concept 415. The method according to inventive concept 405, wherein, when the tissue anchor is unconstrained by the deployment tool:

the open loop surrounds a center point, and (a) a site distance between the site and the distal end of the shaft is greater than (b) a center-point distance between the center point and the distal end of the shaft when the tissue anchor is unconstrained by the deployment tool.

Inventive concept 416. The method according to inventive concept 415, wherein the site distance equals at least 150% of the center-point distance when the tissue anchor is unconstrained by the deployment tool.

Inventive concept 417. The method according to inventive concept 416, wherein the site distance equals at least 175% of the center-point distance when the tissue anchor is unconstrained by the deployment tool.

Inventive concept 418. The method according to inventive concept 405, wherein the site is on an outermost turn of the open loop when the tissue anchor is unconstrained by the deployment tool.

Inventive concept 419. The method according to inventive concept 405, wherein the site is on a second-to-outermost turn of the open loop when the tissue anchor is unconstrained by the deployment tool.

Inventive concept 420. The method according to inventive concept 405, wherein a radius of the flexible elongate tension member is less than a radius of the wire.

Inventive concept 421. The method according to inventive concept 420, wherein the radius of the flexible elongate tension member is less than 50% of the radius of the wire.

Inventive concept 422. The method according to inventive concept 405, wherein the flexible elongate tension member is not fixed to any portion of the open loop beyond 2 mm from the site on the open loop, measured when the tissue anchor is unconstrained by the deployment tool.

Inventive concept 423. The method according to inventive concept 405, wherein, when the tissue anchor is unconstrained by the deployment tool:

the open loop has a greatest lateral dimension, measured perpendicular to the central longitudinal axis, and the flexible elongate tension member is not fixed to any portion of the open loop beyond a distance from the site on the open loop, wherein the distance equals 30% of the greatest lateral dimension.

Inventive concept 424. The method according to inventive concept 405, wherein the flexible elongate tension member is fixed to the open loop only at the site on the open loop.

Inventive concept 425. The method according to inventive concept 405, wherein, when the tissue anchor is unconstrained by the deployment tool:

the open loop has a greatest lateral dimension, measured perpendicular to the central longitudinal axis, and the at least a portion of the open loop crossed by the crossing portion has a length that equals at least 50% of the greatest lateral dimension.

Inventive concept 426. The method according to inventive concept 425, wherein the length of the at least a portion of the open loop crossed by the crossing portion equals at least 75% of the greatest lateral dimension when the tissue anchor is unconstrained by the deployment tool.

Inventive concept 427. The method according to inventive concept 426, wherein the length of the at least a portion of the open loop crossed by the crossing portion equals at least 90% of the greatest lateral dimension when the tissue anchor is unconstrained by the deployment tool.

Inventive concept 428. The method according to inventive concept 405, wherein, when the tissue anchor is unconstrained by the deployment tool and the flexible elongate tension member is tensioned straight, if the tissue-coupling element and the flexible elongate tension member were to be projected onto the plane that is perpendicular to the central longitudinal axis, an angle between (a) the flexible elongate tension member and (b) a tangent to the open loop at the site would be between 70 and 90 degrees.

Inventive concept 429. The method according to inventive concept 405, wherein the site on the open loop is a first site on the open loop, and wherein, when the tissue anchor is unconstrained by the deployment tool and the flexible elongate tension member is tensioned straight:
 the open loop surrounds a center point,
 the wire extends from the distal end of the shaft at a second site on the open loop, and
 if the tissue-coupling element and the flexible elongate tension member were to be projected onto the plane that is perpendicular to the central longitudinal axis, a third angle between the first and the second sites, having a vertex at the center point, would be between 130 and 180 degrees.

Inventive concept 430. The method according to inventive concept 429, wherein the third angle is between 150 and 180 degrees.

Inventive concept 431. The method according to inventive concept 430, wherein the third angle is between 170 and 180 degrees.

Inventive concept 432. The method according to inventive concept 429, the second site is at a radially-outer end of the open loop when the tissue anchor is unconstrained by the deployment tool.

Inventive concept 433. The method according to inventive concept 405, wherein the flexible elongate tension member comprises Nitinol.

Inventive concept 434. The method according to inventive concept 405, wherein one or more tethers are fixed to the flexible elongate tension member.

Inventive concept 435. The method according to inventive concept 405,
 wherein the tissue anchor is a first tissue anchor, and
 wherein the method further comprises:
  implanting a second tissue anchor in the subject, which second tissue anchor is separate and distinct from the first tissue anchor; and
  facilitating repair of an atrioventricular valve of the subject by applying tension to one or more tethers that couple the flexible elongate tension member to the second tissue anchor.

Inventive concept 436. The method according to inventive concept 435, further comprising, before applying the tension, coupling the flexible elongate tension member to the second tissue anchor using the one or more tethers.

Inventive concept 437. The method according to inventive concept 435, wherein the one or more tethers are fixed to (a) the flexible elongate tension member to (b) the second tissue anchor.

Inventive concept 438. The method according to inventive concept 435, wherein the second tissue anchor comprises a helical tissue-coupling element.

Inventive concept 439. The method according to inventive concept 435, wherein the second tissue anchor comprises a stent.

Inventive concept 440. The method according to inventive concept 405,
 wherein the tissue anchor is a first tissue anchor, and
 wherein the method further comprises:
  implanting a second tissue anchor in the subject, which second tissue anchor is (a) separate and distinct from the first tissue anchor, and (b) coupled to the flexible elongate tension member; and
  facilitating repair of an atrioventricular valve of the subject by applying tension to flexible elongate tension member.

Inventive concept 441. The method according to inventive concept 440, wherein the flexible elongate tension member is fixed to the second tissue anchor.

Inventive concept 442. The method according to inventive concept 405, wherein introducing comprises introducing the tissue anchor while the tissue-coupling element is constrained by the deployment tool, and a longitudinal portion of the flexible elongate tension member runs alongside a portion of the wire.

Inventive concept 443. The method according to inventive concept 404, wherein, when the tissue anchor is unconstrained by the deployment tool:
 the wire of the tissue-coupling element is shaped as an open loop having more than one turn around a center point, and
 the wire extends from the distal end of the shaft at a radially-outer end of the open loop.

Inventive concept 444. The method according to inventive concept 443, wherein the open loop is shaped as a spiral when the tissue anchor is unconstrained by the deployment tool.

Inventive concept 445. The method according to inventive concept 444, wherein the spiral is shaped as a three-dimensional spiral when the tissue anchor is unconstrained by the deployment tool.

Inventive concept 446. The method according to inventive concept 444, wherein the spiral is shaped as an elliptical spiral when the tissue anchor is unconstrained by the deployment tool.

Inventive concept 447. The method according to inventive concept 443, wherein the open loop is shaped as a three-dimensional open loop when the tissue anchor is unconstrained by the deployment tool.

Inventive concept 448. The method according to inventive concept 443, wherein the wire intersects the center point when the tissue anchor is unconstrained by the deployment tool.

Inventive concept 449. The method according to inventive concept 443, wherein the wire does not intersect the center point when the tissue anchor is unconstrained by the deployment tool.

Inventive concept 450. The method according to inventive concept 443, wherein, when the tissue anchor is unconstrained by the deployment tool:
 the open loop has a greatest lateral dimension, measured perpendicular to the central longitudinal axis, and
 a distance between (a) the radially-outer end of the open loop and (b) a radially-inner-most point of the open loop, measured perpendicular to the central longitudinal axis, is equal to at least 30% of the greatest lateral dimension.

Inventive concept 451. The method according to inventive concept 443, wherein a proximally-facing surface defined by the tissue-coupling element is convex when the tissue anchor is unconstrained by the deployment tool, and wherein the method further comprises bringing the proximally-facing surface defined by the tissue-coupling element into contact with an external surface of the heart.

Inventive concept 452. The method according to inventive concept 404, wherein a cross-sectional area of the wire is at least 0.09 mm2.

Inventive concept 453. The method according to inventive concept 452, wherein the cross-sectional area of the wire is no more than 2.9 mm2.

Inventive concept 454. The method according to inventive concept 388, wherein the central longitudinal axis is straight when the tissue anchor is unconstrained by the deployment tool.

Inventive concept 455. The method according to inventive concept 388, wherein the shaft is flexible.

Inventive concept 456. The method according to inventive concept 388, wherein the shaft and the tissue-coupling element are integral to one another.

Inventive concept 457. The method according to inventive concept 456, wherein the shaft and the tissue-coupling element comprise a wire.

Inventive concept 458. The method according to inventive concept 388, wherein the deployment tool comprises a hypodermic needle.

Inventive concept 459. The method according to inventive concept 388, wherein the tissue anchor is a first tissue anchor, and
wherein the method further comprises:
implanting a second tissue anchor in the subject, which second tissue anchor is separate and distinct from the first tissue anchor; and
facilitating repair of an atrioventricular valve of the subject by applying tension to one or more tethers that couple the first tissue anchor to the second tissue anchor.

Inventive concept 460. The method according to inventive concept 459, wherein facilitating repair comprises facilitating repair of the atrioventricular valve by applying the tension to the one or more tethers that couple the head of the first tissue anchor to the second tissue anchor.

Inventive concept 461. The method according to inventive concept 459, further comprising, before applying the tension, coupling the first tissue anchor to the second tissue anchor using the one or more tethers.

Inventive concept 462. The method according to inventive concept 459, wherein one of the one or more tethers is fixed to one of (a) the first tissue anchor to (b) the second tissue anchor.

Inventive concept 463. The method according to inventive concept 459, wherein the second tissue anchor comprises a helical tissue-coupling element.

Inventive concept 464. The method according to inventive concept 459, wherein the second tissue anchor comprises a stent.

There is additionally provided, in accordance with an inventive concept 465 of the present invention, a method comprising:

providing a tissue anchor that comprises (a) a shaft and (b) a tissue-coupling element, which extends from a distal end of the shaft, and which comprises three or more tines;

introducing, during a transcatheter procedure, the tissue anchor into a cardiac chamber of a heart of a subject, while the tissue-coupling element is constrained by a deployment tool;

delivering the tissue-coupling element through a wall of the heart; and at least partially releasing the tissue anchor from the deployment tool such that (a) the tissue-coupling element is unconstrained by the deployment tool, (b) the tines extend radially outward from a central longitudinal axis of the shaft in respective directions that are fixed with respect to one another, and (c) the tissue-coupling element is shaped such that if the tissue-coupling element were to be projected onto a plane that is perpendicular to the central longitudinal axis, at least 80% of an area of the projection of the tissue-coupling element on the plane would fall within an angle of 210 degrees in the plane having a vertex at the central longitudinal axis.

Inventive concept 466. The method according to inventive concept 465, further comprising:

ascertaining whether the tissue-coupling element overlies a coronary blood vessel; and if the tissue-coupling element overlies the coronary blood vessel, rotating the tissue anchor until the tissue-coupling element no longer overlies the coronary blood vessel.

Inventive concept 467. The method according to inventive concept 465, further comprising, after delivering the tissue-coupling element through the wall of the heart, rotating the tissue anchor and bringing the tissue-coupling element into contact with an external surface of the heart.

Inventive concept 468. The method according to inventive concept 465, wherein the three or more tines comprise four or more tines.

Inventive concept 469. The method according to inventive concept 465, wherein at least 80% of the area of the projection of the tissue-coupling element on the plane would fall within a second angle of 180 degrees in the plane having the vertex at the central longitudinal axis.

Inventive concept 470. The method according to inventive concept 465, wherein the tissue-coupling element further comprises one or more membranes that are fixed to and extend between circumferentially-adjacent ones of the tines.

Inventive concept 471. The method according to inventive concept 470, wherein the tines are first tines, and wherein the one or more membranes are one or more first membranes that are fixed to and extend between circumferentially-adjacent ones of the first tines,
wherein the tissue-coupling element further comprises:
three or more second tines;
one or more second membranes that are fixed to and extend between circumferentially-adjacent ones of the second tines, and are not fixed to any of the first tines, and
wherein the first membranes are not fixed to any of the second tines.

Inventive concept 472. The method according to inventive concept 471, wherein the tissue anchor is configured such that the second tines are rotatable with respect to the first tines, and wherein the method further comprises rotating the second tines with respect to the first tines.

Inventive concept 473. The method according to inventive concept 472, wherein rotating the second tines with respect to the first tines comprises setting a level of circumferential overlap of the second membranes with the first membranes.

Inventive concept 474. The method according to inventive concept 473, wherein delivering the tissue-coupling element through the wall comprises delivering the tissue-coupling element through the wall in a vicinity of a coronary blood vessel, and wherein setting the level of circumferential overlap comprises avoiding contacting the coronary blood vessel with the tissue-coupling element by setting the level of circumferential overlap.

Inventive concept 475. The method according to inventive concept 473, wherein setting the level of circumferential overlap comprises setting the level of circumferential overlap such that the first and the second membranes together extend circumferentially around the central longitudinal axis by between 100 and 350 degrees.

Inventive concept 476. The method according to inventive concept 475, wherein setting the level of circumferential overlap comprises setting the level of circumferential overlap such that the first and the second membranes together extend circumferentially around the central longitudinal axis by between 150 and 270 degrees.

Inventive concept 477. The method according to inventive concept 473, wherein, when the tissue anchor is unconstrained by the deployment tool, the tissue-coupling element is shaped such that (a) the first membranes extend circumferentially around the central longitudinal axis between 90 and 180 degrees, and (b) the second membranes extend circumferentially around the central longitudinal axis between 90 and 180 degrees.

Inventive concept 478. The method according to inventive concept 465,
wherein the tines are first tines, which are rationally fixed with respect to one another,
wherein the tissue-coupling element further comprises three or more second tines, which are rationally fixed with respect to one another,
wherein the tissue anchor is configured such that the second tines are rotatable with respect to the first tines, and
wherein the method further comprises rotating the second tines with respect to the first tines.

Inventive concept 479. The method according to inventive concept 465,
wherein the tissue anchor is a first tissue anchor, and
wherein the method further comprises:
implanting a second tissue anchor in the subject, which second tissue anchor is separate and distinct from the first tissue anchor; and
facilitating repair of an atrioventricular valve of the subject by applying tension to one or more tethers that couple the first tissue anchor to the second tissue anchor.

Inventive concept 480. The method according to inventive concept 479, further comprising, before applying the tension, coupling the first tissue anchor to the second tissue anchor using the one or more tethers.

Inventive concept 481. The method according to inventive concept 479, wherein one of the one or more tethers is fixed to one of (a) the first tissue anchor and (b) the second tissue anchor.

Inventive concept 482. The method according to inventive concept 479, wherein the second tissue anchor comprises a helical tissue-coupling element.

Inventive concept 483. The method according to inventive concept 479, wherein the second tissue anchor comprises a stent.

Inventive concept 484. The method according to inventive concept 465, wherein a proximally-facing surface defined by the tissue-coupling element is concave when the tissue anchor is unconstrained by the deployment tool.

Inventive concept 485. The method according to inventive concept 465, wherein, when the tissue anchor is unconstrained by the deployment tool:
a greatest longitudinal dimension of the tissue-coupling element, measured parallel to the central longitudinal axis, is between 1 and 5 mm, and
a greatest lateral dimension of the tissue-coupling element, measured perpendicular to the central longitudinal axis, is between 4 and 20 mm.

Inventive concept 486. The method according to inventive concept 465, wherein the shaft comprises a sealing element.

Inventive concept 487. The method according to inventive concept 465, wherein the central longitudinal axis is straight when the tissue anchor is unconstrained by the deployment tool.

Inventive concept 488. The method according to inventive concept 465, wherein the shaft is flexible.

There is yet additionally provided, in accordance with an inventive concept 489 of the present invention, apparatus for delivery in a constrained state within a deployment tool, the apparatus comprising a tissue anchor, which comprises:
a shaft having a central longitudinal axis;
a tissue-coupling element, which comprises a wire, wherein when the tissue anchor is unconstrained by the deployment tool: (a) the wire is shaped as an open shape, and (b) if the tissue-coupling element were to be projected onto a plane that is perpendicular to the central longitudinal axis, the open shape would surround between 170 and 355 degrees of a point in the plane; and
a flexible elongate tension member, which includes (a) a distal portion that is fixed to a site on the wire, (b) a proximal portion, which has a longitudinal segment that runs alongside at least a portion of the shaft, and (c) a crossing portion, which (i) is disposed between the distal and the proximal portions along the flexible elongate tension member, and (ii) crosses at least a portion of the open shape when the tissue anchor is unconstrained by the deployment tool,
wherein the tissue anchor is configured to allow relative axial motion between the at least a portion of the shaft and the longitudinal segment of the proximal portion of the flexible elongate tension member when the tissue anchor is unconstrained by the deployment tool.

Inventive concept 490. The apparatus according to inventive concept 489,
wherein the tissue anchor comprises a head connected to a proximal portion of the shaft,
wherein the head is shaped so as to define a passage in which the proximal portion of the flexible elongate tension member is slidably disposed,
wherein the flexible elongate tension member comprises a locking stopper, which is axially fixed to the proximal or the crossing portion of the flexible elongate tension member, and
wherein the locking stopper and the passage are sized and shaped such that the size and shape of the passage prevent proximal movement of the locking stopper past the passage.

Inventive concept 491. The apparatus according to inventive concept 489, wherein the open shape is shaped as a portion of a circle or a portion of an ellipse when the tissue anchor is unconstrained by the deployment tool.

Inventive concept 492. The apparatus according to inventive concept 489, wherein the site on the wire is at a distal end of the wire.

Inventive concept 493. The apparatus according to inventive concept 492, wherein the wire is shaped so as to define a channel, through which a portion of the flexible elongate tension member passes and exits the wire at the distal end of the wire.

The present invention will be more fully understood from the following detailed description of embodiments thereof, taken together with the drawings, in which:

BRIEF DESCRIPTION OF THE DRAWINGS

FIGS. 1A-D are schematic illustrations of a tissue anchor in several stages of deployment from a deployment tool, in accordance with an application of the present invention;

FIGS. 3A-B are schematic illustrations of the tissue-coupling element and the shaft of the tissue anchor of FIGS. 1A-D, in accordance with respective applications of the present invention;

FIGS. 5A-D are schematic illustrations of another tissue anchor in several stages of deployment from a deployment tool, in accordance with an application of the present invention;

FIGS. 6A-B are schematic illustrations of two configurations of another tissue anchor system, in accordance with respective applications of the present invention;

FIGS. 8A and 8B are schematic illustrations of two configurations of yet another tissue anchor, in accordance with respective applications of the present invention;

FIGS. 10A-B are schematic illustrations of another tissue anchor in several stages of deployment from a deployment tool, in accordance with an application of the present invention;

FIGS. 11A-C are schematic illustrations of several views of yet another tissue anchor, in accordance with an application of the present invention;

FIGS. 13A-D are schematic illustrations of a method for deploying the tissue anchor system of FIGS. 4A-B for repairing a tricuspid valve, in accordance with an application of the present invention;

FIGS. 17A-F are schematic illustrations of a tissue-anchor system in an unlocked state, in accordance with an application of the present invention.

DETAILED DESCRIPTION OF APPLICATIONS

Figure 2A:
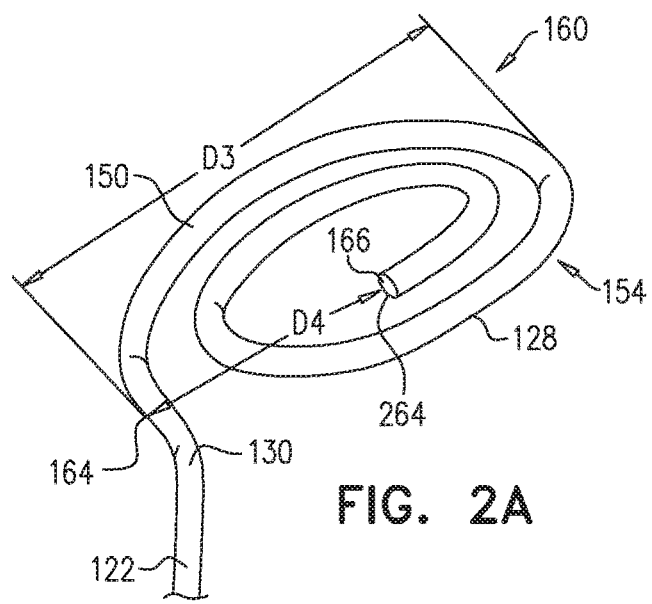
FIGS. 2A-B and 2C are schematic illustrations of a tissue-coupling element and a shaft of the tissue anchor of FIGS. 1A-D, in accordance with respective applications of the present invention.

Some embodiments of the present invention provide a tissue anchor 20 and a deployment tool 30, which is typically configured to deliver the tissue anchor through a wall of a heart of a subject, typically by advancing a sharp distal piercing tip 32 of the deployment tool through the wall.

FIGS. 1A-D are schematic illustrations of a tissue anchor 120 in several stages of deployment from deployment tool 30, in accordance with an application of the present invention. Tissue anchor 120 is one implementation of tissue anchor 20, described above. Tissue anchor 120 comprises (a) a shaft 122, (b) a head 124 connected to a proximal portion 126 of shaft 122, and (c) a tissue-coupling element 128, which extends from a distal end 130 of shaft 122. For some applications, shaft 122 and tissue-coupling element 128 are integral to one another; for example, shaft 122 and tissue-coupling element 128 may comprise a wire. For some applications, one or more tethers 132 are provided, which are configured to be coupled to tissue anchor 120, such as to head 124 of tissue anchor 120; for example, one of the one or more tethers 132 may be fixed to head 124.

Deployment tool 30 is configured to constrain tissue-coupling element 128 while delivering tissue-coupling element 128 through tissue. Typically, during delivery, such as shown in FIG. 1A, deployment tool 30 is configured to hold tissue-coupling element 128 in an elongated configuration, which may be straight (such as shown) or curvy (such as shown in FIG. 5A). For some applications, deployment tool 30 comprises a shaft 34 shaped so as to define a lumen, such as a hypodermic needle. The lumen is sized to hold tissue-coupling element 128 constrained therein, and, optionally, to hold other portions of tissue anchor 20 therein, such as shaft 122 and/or head 124. For some applications, deployment tool 30 has a length of between 100 and 180 cm, and/or an inner diameter of between 2 and 6 mm. For some applications, deployment tool 30 comprises a distal-most rigid portion, which typically has a length of 5 to 25 mm, and the remaining proximal portion of the deployment tool is flexible (but not extendable or compressible). For some applications, the proximal portion is shaped so as to define one or more lateral slots, which provide flexibility to the proximal portion, while maintaining a backbone that prevents longitudinal compression and extension of the proximal portion. Typically, deployment tool 30 is advanced within a steerable catheter tube 40, as is known in the art, which may, for example, comprise a braided material. Typically, tissue anchor 20 is provided in sterile packaging, optionally pre-positioned in deployment tool 30.

FIG. 1A shows tissue anchor 120 (including tissue-coupling element 128, shaft 122, and head 124) fully constrained by deployment tool 30. When tissue anchor 120 is fully constrained by deployment tool 30, tissue-coupling element 128 typically has an outer diameter of at least 0.3 mm, no more than 4 mm, and/or between 0.3 and 4 mm, such as at least 1 mm, no more than 3 mm, and/or between 1 and 3 mm.

FIG. 1B shows tissue-coupling element 128 released from deployment tool 30, while a portion of tissue anchor 120 is still constrained by deployment tool 30.

FIG. 1C shows tissue anchor 120 entirely released from deployment tool 30.

FIG. 1D shows tissue anchor 120 deployed against a wall 194 of a heart chamber, upon release from deployment tool 30. Tissue-coupling element 128 is disposed on a far side of wall 194, and head 124 is disposed on a near side of wall 194.

Figure 2B:
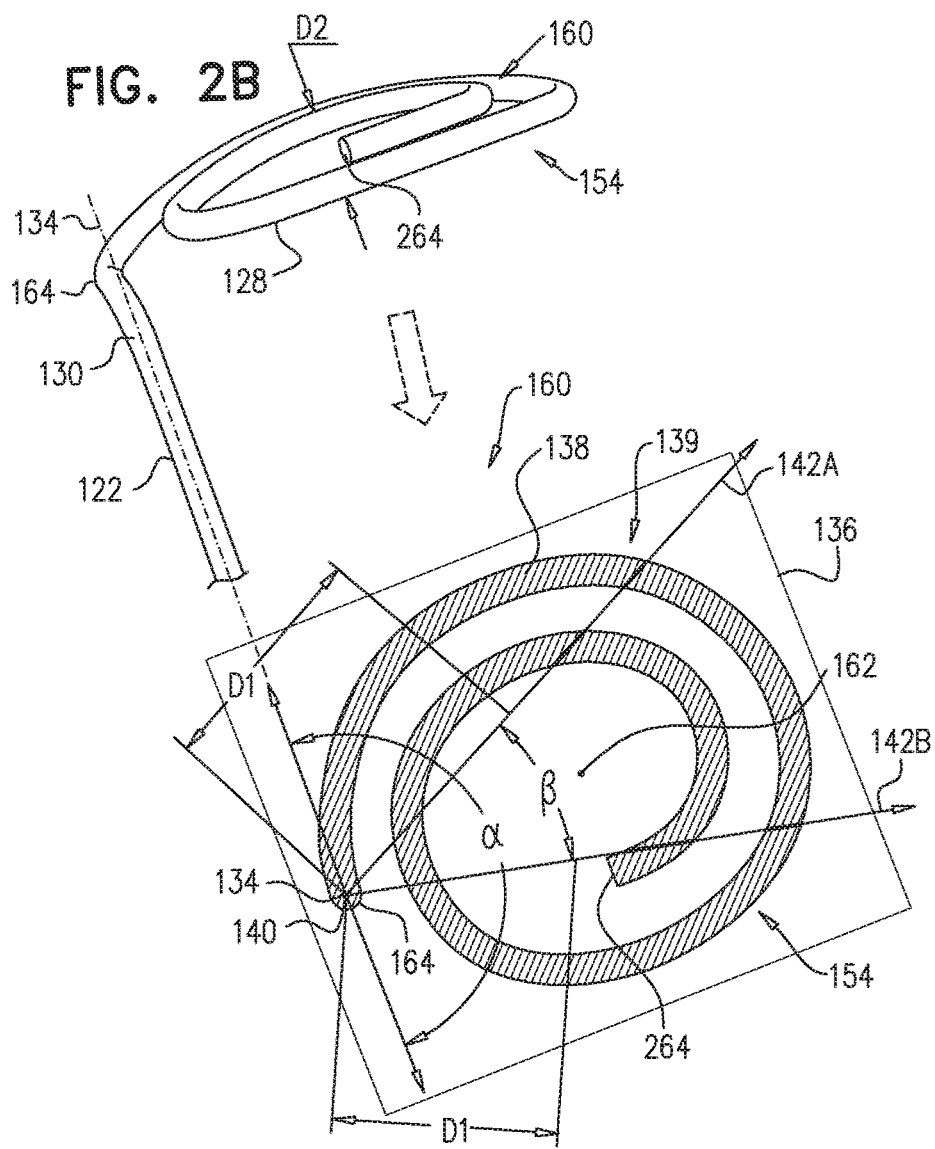
Figure 2C:
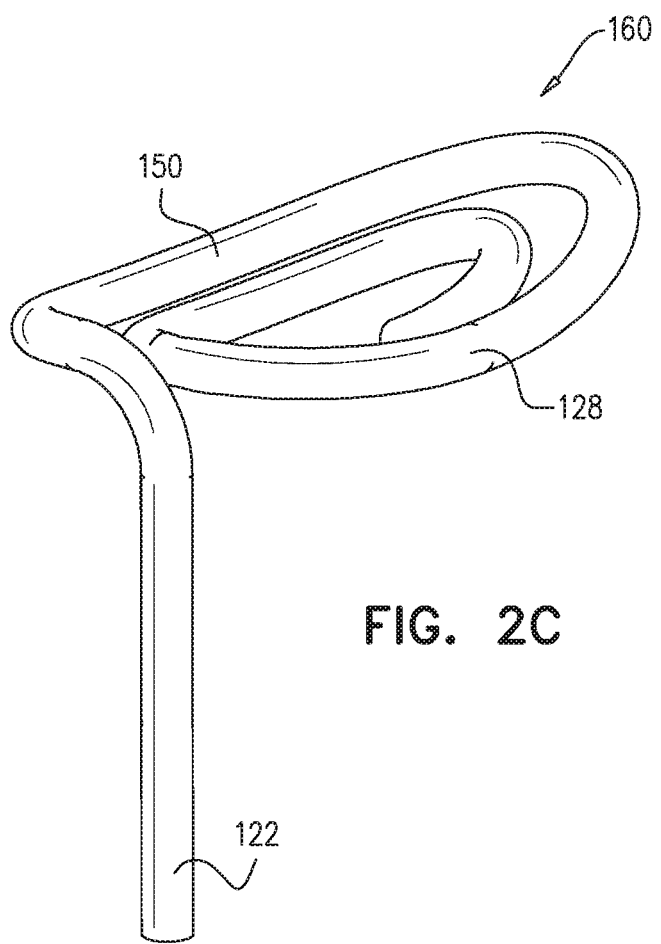

Reference is now made to FIGS. 2A-B and 2C, which are schematic illustrations of tissue-coupling element 128 and shaft 122, in accordance with respective applications of the present invention. FIGS. 2A-B provide two views of a first configuration tissue-coupling element 128 and shaft 122, when tissue anchor 120 is unconstrained by deployment tool 30, and FIG. 2C provides a view of a second configuration of tissue-coupling element 128 and shaft 122, when tissue anchor 120 is unconstrained by deployment tool 30.

Reference is made to FIGS. 1B-C and 2A-C. When tissue anchor 120 is unconstrained by deployment tool 30, such as shown in FIGS. 1B-C and 2A-C:
- shaft 122 has a central longitudinal axis 134,
- head 124 is coaxial with central longitudinal axis 134, and
- tissue-coupling element 128 is shaped such that if tissue-coupling element 128 were to be projected onto a plane 136 that is perpendicular to central longitudinal axis 134:
  - at least 80% (e.g., at least 90%, such as at least 95%) of an area 138 of a projection 139 of tissue-coupling element 128 on plane 136 would fall within a first angle α (alpha) of 180 degrees in plane 136 having a vertex 140 at central longitudinal axis 134, as labeled in FIG. 2B, and
  - area 138 would partially overlap, at a distance D1 of at least 3 mm from vertex 140, both rays 142A and 142B of a second angle β (beta) of between 45 and 180 degrees in plane 136 having vertex 140 at central longitudinal axis 134 (the partial overlap is illustrated by the heavier portions of the rays).

As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

Tissue-coupling element 128 is configured to have a predetermined shape when unconstrained by deployment tool 30. For example, the tissue-coupling element may comprise a shape-memory material, such as a shape-memory alloy, e.g., Nitinol. Thus, tissue-coupling element 128 automatically transitions to the predetermined shape when released from being constrained by deployment tool 30 to being unconstrained by deployment tool 30.

For some applications, central longitudinal axis 134 is straight when tissue anchor 120 is unconstrained by deployment tool 30, such as shown in FIGS. 1B-C and 2A-C. For some applications, shaft 122 is flexible.

For some applications, such as shown in FIGS. 1B-C and 2A-B, a proximally-facing surface defined by tissue-coupling element 128 (i.e., the surface defined by tissue-coupling element 128 that is configured to touch the external surface of the heart) is concave when tissue anchor 120 is unconstrained by deployment tool 30 (in other words, tissue-coupling element 128 is concave when viewed from proximal portion 126 of shaft 122). Such a concave shape may approximate the natural convex shape of an external surface of the wall of the heart.

For other applications, such as shown in FIG. 2C, the proximally-facing surface defined by tissue-coupling element 128 is convex, when tissue anchor 120 is unconstrained by deployment tool 30 before being pulled against the external surface of the heart (in other words, tissue-coupling element 128 is convex when viewed from proximal portion 126 of shaft 122). Such a convex shape may be employed such that the radially internal section of the coil closest to a center point 162 of tissue-coupling element 128 contacts the tissue first, and gradually, as tension is applied, the full tissue-coupling element comes into contact with the external surface of the heart. Optionally, upon coming into full contact with the external surface of the heart, the proximally-facing surface defined by the tissue-coupling element may assume a concave shape conforming to the convex shape of the external surface of the heart. This arrangement may lead to a more even distribution of load on the heart tissue and result in a more durable loading configuration on the tissue.

For still other applications, the proximally-facing surface defined by tissue-coupling element 128 is generally flat, when tissue anchor 120 is unconstrained by deployment tool 30 (configuration not shown). Optionally, upon coming into full contact with the external surface of the heart, the proximally-facing surface defined by the tissue-coupling element may assume a concave shape conforming to the convex shape of the external surface of the heart.

For some applications, when tissue anchor 120 is unconstrained by deployment tool 30:
- a greatest longitudinal dimension D2 of tissue-coupling element 128, measured parallel to central longitudinal axis 134, is between 1 and 6 mm (such as between 2 and 5 mm) (labeled in FIG. 2B), and
- a greatest lateral dimension D3 of tissue-coupling element 128, measured perpendicular to central longitudinal axis 134, is between 4 and 25 mm (such as between 5 and 20 mm) (labeled in FIG. 2A).

Typically, a ratio of the greatest longitudinal dimension D2 and greatest lateral dimension D3 is between 1:2 and 1:18, such as between 1:5 and 1:10, e.g., 1:7 when tissue anchor 120 is unconstrained by deployment tool 30.

For some applications, tissue-coupling element 128 has a length L of at least 5 mm (e.g., at least 10 mm), no more than 100 mm (e.g., no more than 60 mm), and/or between 5 and 100 mm (e.g., between 10 and 60 mm) when constrained into a straight configuration, such as shown in FIG. 1A.

For some applications, tissue-coupling element 128 comprises a wire 150. For some applications, a cross-sectional area of wire 150 is at least 0.09 mm2 (such as at least 0.18 mm2), no more than 3 mm2 (e.g., no more than 2.9 mm2), and/or between 0.09 mm2 (such as 0.18 mm2) and 3 mm2 (e.g., 2.9 mm2). For some applications, wire 150 has a circular cross-section, and a diameter of wire 150 is at least 0.18 mm, no more than 2 mm, and/or between 0.18 and 2 mm. For some applications, a distal end 152 of wire 150 does not define a sharp distal tip; for example, the distal end may be blunt. For some applications, wire 150 comprises metal, such as Nitinol. For some applications, wire 150 comprises one or more radiopaque markers.

For some applications, when tissue anchor 120 is unconstrained by deployment tool 30, such as shown in FIGS. 1B-C and 2A-C, wire 150 (*a*) is shaped as an open loop 154 having more than one turn, such that a first complete turn of open loop 154 at least partially overlaps (i.e., runs alongside, above, and/or below) a second at-least-partial turn of open loop 154. For some applications, the first complete turn and the second at-least-partial turn radially coincide, i.e., are at a same distance as each other from a center point (configuration not shown). For other applications, as shown in the figures, an outermost turn of open loop 154 at least partially overlaps (i.e., runs alongside, above, and/or below) a second-to-outermost turn of open loop 154 (for example, an outermost turn 214 and a second-to-outermost turn 216 of open loop 154 are labeled in FIG. 5D). (As used in the present application, including in the claims, one turn equals 360 degrees. As used in the present application, including in the claims, "more than one turn" should not be understood as requiring at least two turns; instead, "more than one turn" also includes one turn plus a fraction of a turn, as described below. For example, for applications in which open loop 154 includes an outermost turn and a second-to-outermost turn, the second-to-outermost turn of open loop 154 may be a partial turn, such as shown in FIGS. 9A-B, 9E, 9F, and 9I.)

For applications in which open loop 154 includes an outermost turn and a second-to-outermost turn, open loop 154 has a radially-outer end 164 and a radially-inner end 264, which typically do not touch each other at least when tissue anchor 120 is unconstrained by deployment tool 30. For applications in which the first complete turn and the second at-least-partial turn radially coincide, the two opposite ends of the open loop typically do not touch each other at least when tissue anchor 120 is unconstrained by deployment tool 30. Open loop 154 is defined by an elongate path of wire 150 that winds more than one turn around center point 162 without forming a closed loop. The elongate path may include one or more curved segments and/or one or more straight segments, such as described hereinbelow with reference to FIG. 9I. The path may fall in two dimensions, or may fall in three dimensions, in which case the open loop is a three-dimensional open loop, the elongate path of which winds around a center axis while moving parallel to the axis, without forming a closed loop.

For some applications, open loop 154 extends from distal end 130 of shaft 122 at radially-outer end 164 of open loop 154. For some applications, wire 150 intersects center point 162 when tissue anchor 120 is unconstrained by deployment tool 30 (configuration not shown), while for other applications, wire 150 does not intersect center point 162 when tissue anchor 120 is unconstrained by deployment tool 30 (as shown).

For some applications, such as shown in FIGS. 1B, 2A-C, 3A-B, 4B, 9A-B, and 9E-G, when tissue anchor 120 is unconstrained by deployment tool 30, open loop 154 has more than one turn and less than two turns. For example, as shown in FIGS. 1B, 2A-C, 3A-B, and 4B, open loop 154 may have at least 1.5 turns and no more than two turns, or, as shown in FIGS. 9A-B, and 9E-G, open loop 154 may have more than one turn and less than 1.5 turns, such as more than one turn, e.g., more than 1.01 turns (363.6 degrees), such as more than 1.02 turns (367.2 degrees), and/or less than 1.25 turns (450 degrees). For other applications, such as shown in FIGS. 5B-D, 6A-B, 7A-B, and 8A-B, open loop 154 may have at least two turns, such as at least two turns and less than 2.5 turns (as shown in FIGS. 5B-D and 6A-B), or more than 2.5 turns, e.g., more than three turns (configurations not shown).

For some applications, when tissue anchor 120 is unconstrained by deployment tool 30, such as shown in FIGS. 1B-C and 2A-C, wire 150 of open loop 154 is shaped as a spiral 160 (e.g., a three-dimensional spiral) around center point 162. For some of these applications, wire 150 of spiral 160 extends from distal end 130 of shaft 122 at radially-outer end 164 of spiral 160. For some applications, wire 150 of spiral 160 intersects center point 162 when tissue anchor 120 is unconstrained by deployment tool 30 (configuration not shown), while for other applications, wire 150 of spiral 160 does not intersect center point 162 when tissue anchor 120 is unconstrained by deployment tool 30 (as shown). For some applications, spiral 160 is generally circular when tissue anchor 120 is unconstrained by deployment tool 30, such as shown in FIGS. 1B, 2A-C, and 3A-B, while for other applications, spiral 160 is an elliptical spiral when the tissue anchor is unconstrained by deployment tool 30, such as shown in FIGS. 5B-D, 6A-B, 7A, 8A, 9A-B, and 9E-G.

As used in the present application, including in the claims, center point 162 is the centroid of projection 139 of tissue-coupling element 128 on plane 136. Typically, such as when tissue-coupling element 128 is shaped as a spiral, tissue-coupling element 128 is non-helical when tissue anchor 120 is unconstrained by deployment tool 30.

For some applications, such as shown in FIGS. 1B, 2A-C, 3A-B, 4B, 9A-B, and 9E-G, when the tissue anchor is unconstrained by deployment tool 30, spiral 160 has more than one turn and less than two turns. For example, as shown in FIGS. 1B, 2A-C, 3A-B, and 4B, spiral 160 may have at least 1.5 turns and no more than two turns, or, as shown in FIGS. 9A-B and 9E-G, spiral 160 may have more than one turn and less than 1.5 turns, such as more than one turn and less than 1.25 turns. For other applications, such as shown in FIGS. 5B-D, 6A-B, 7A-B, and 8A-B, spiral 160 may have at least two turns, such as at least two turns and less than 2.5 turns (as shown in FIGS. 5B-D and 6A-B), or more than 2.5 turns, e.g., more than three turns (configurations not shown).

For some applications, as labeled in FIG. 2A, when tissue anchor 120 is unconstrained by deployment tool 30, the open loop (e.g., the spiral) has greatest lateral dimension D3, measured perpendicular to central longitudinal axis 134, and a distance D4 between (a) radially-outer end 164 of open loop 154 (e.g., spiral 160) and (b) a radially-inner-most point 166 of open loop 154 (e.g., spiral 160), measured perpendicular to central longitudinal axis 134, is equal to at least 30% of the greatest lateral dimension D3. Alternatively or additionally, for some applications, a distance between radially-inner-most point 166 and a closest point thereto on an outermost turn of open loop 154, measured perpendicular to central longitudinal axis 134, is equal to at least 30% of the greatest lateral dimension D3. For other applications, such as those described hereinbelow with reference to FIGS. 9A-B and 9E-G, a distance between radially-inner-most point 166 and a closest point thereto on an outermost turn of open loop 154, measured perpendicular to central longitudinal axis 134, equals less than 10% of the greatest lateral dimension D3.

Reference is made to FIGS. 3A-B, which are schematic illustrations of tissue-coupling element 128 and shaft 122, in accordance with respective applications of the present invention. For some applications, as shown in FIG. 3A, at least 80%, such as at least 90%, e.g., at least 95%, of area 138 of projection 139 of tissue-coupling element 128 on plane 136 would fall within a third angle γ (gamma) of 150 degrees in plane 136 having vertex 140 at central longitudinal axis 134, if tissue-coupling element 128 were to be projected onto plane 136.

For some applications, as shown in FIG. 3B, an outer portion 168 of area 138 of projection 139 of tissue-coupling element 128 on plane 136 consists of all points of area 138 at least a distance D from vertex 140; for example, the distance D may be 2 mm, such as 3 mm, e.g., 4 mm. Outer portion 168 would fall within all angular positions of a fourth angle δ (delta) of 90 degrees in plane 136 having vertex 140 at central longitudinal axis 134, which outer portion 168, if tissue-coupling element 128 were to be projected onto plane 136. In other words, at all angular positions of fourth angle δ (delta), there is at least one point of outer portion 168. (Outer portion 168 may additionally fall within angular positions outside of fourth angle δ (delta), such as shown in FIG. 3B.)

Figure 4A:
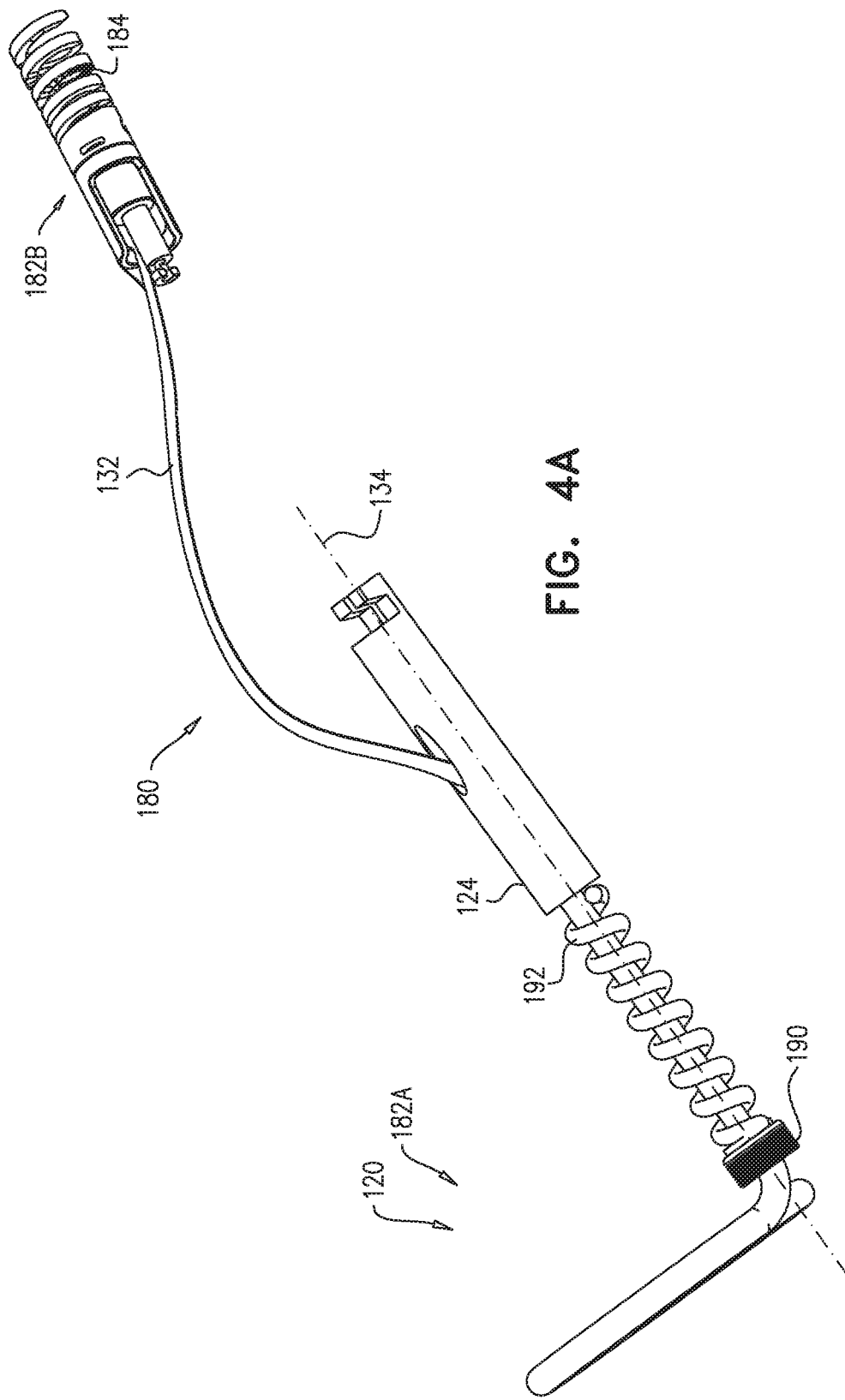
FIGS. 4A-B are schematic illustrations of two configurations of a tissue anchor system, in accordance with respective applications of the present invention.
Figure 4B:
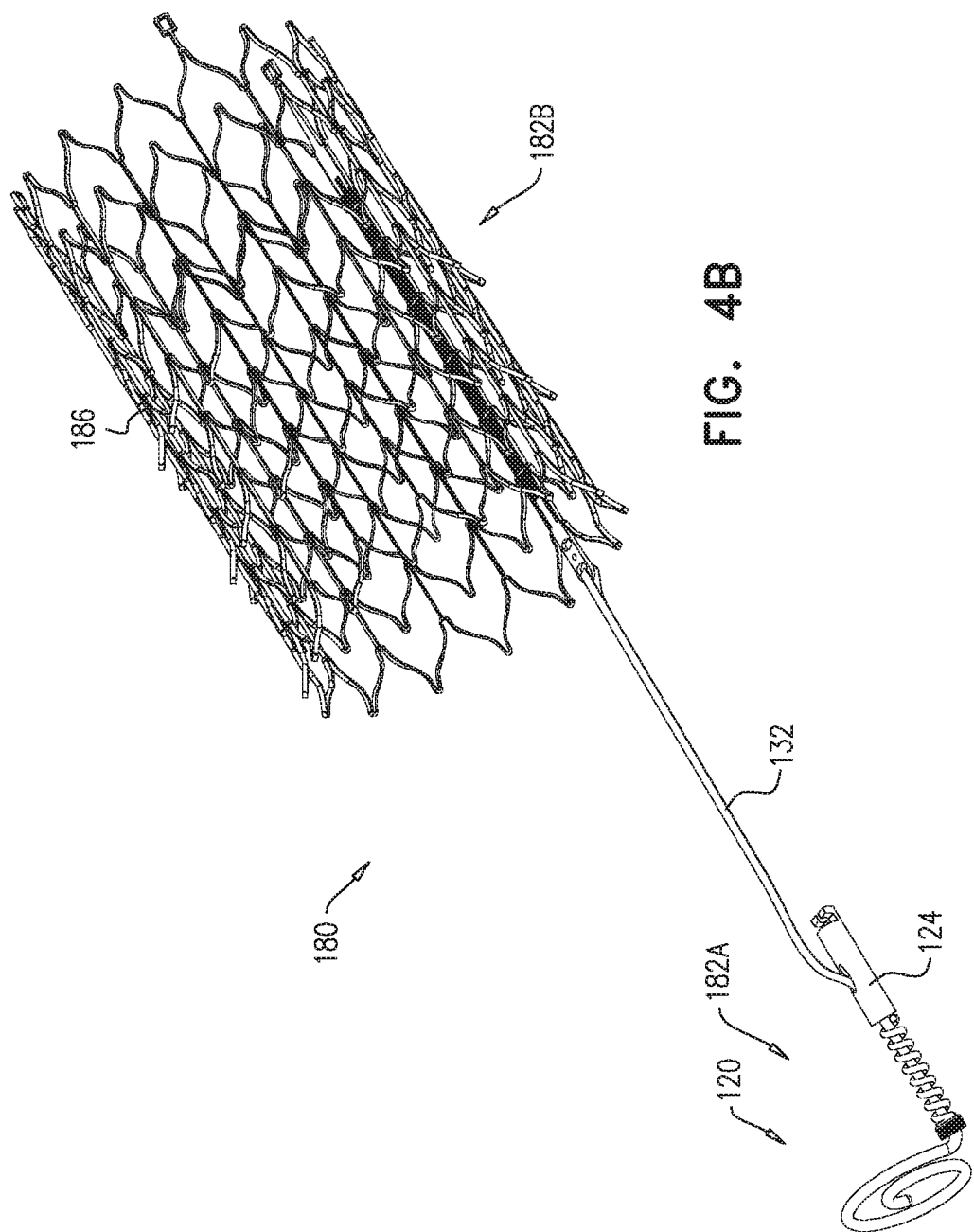

Reference is now made to FIGS. 4A-B, which are schematic illustrations of two configurations of a tissue anchor system 180, in accordance with respective applications of the present invention. In these applications, tissue anchor 120 is a first tissue anchor 182A of tissue anchor system 180, which further comprises (a) a second tissue anchor 182B, which is separate and distinct first tissue anchor 182A, and (b) the one or more tethers 132, which are configured to couple (i) head 124 of first tissue anchor 182A to (ii) second tissue anchor 182B. For some applications, one of the one or more tethers 132 is fixed to (a) head 124 of first tissue anchor 182A and (b) second tissue anchor 182B.

For some applications, such as shown in FIG. 4A, second tissue anchor 182B comprises a helical tissue-coupling element 184. For example, second tissue anchor 182B may implement techniques described in PCT Publication WO 2014/108903, which is incorporated herein by reference. For other applications, such as shown in FIG. 4B, second tissue anchor 182B comprises a stent 186. For example, second tissue anchor 182B may implement techniques described in one or more of the following applications, which are incorporated herein by reference: US Patent Application Publication 2011/0184510, US Patent Application Publication 2012/0035712, US Patent Application Publication 2013/0018459, US Patent Application Publication 2013/0046380, and/or PCT Publication WO 2014/141239.

Reference is made to FIGS. 1A-D and 4A-B. For some applications, shaft 122 comprises a sealing element 190, which is configured to form a blood-tight seal between a portion of shaft 122 inside the heart chamber and wall 194 of the heart. For some applications, sealing element 190 is annular, and snugly surrounds shaft 122. For some applications, shaft 122 further comprises a spring 192, which is disposed proximal to sealing element 190, and is configured to apply a distal force to sealing element 190, in order to push sealing element against wall 194 of the heart chamber, in order to form a tight seal, such as shown in FIG. 1D.

Reference is made to FIGS. 1A-4B. For some applications, tissue anchor 120 is implanted using techniques described hereinbelow with reference to FIGS. 13A-D, 15A-C, and/or 16, optionally in combination with techniques described in one or more of the patents and patent application publications incorporated hereinbelow by reference, mutatis mutandis.

Reference is now made to FIGS. 5A-D, which are schematic illustrations of a tissue anchor 200 in several stages of deployment from deployment tool 30, in accordance with an application of the present invention. Tissue anchor 200 is one implementation of tissue anchor 20, described above.

Other than as described below, tissue anchor 200 is generally similar to tissue anchor 120, described hereinabove with reference to FIGS. 1A-4B, and may implement any of the features thereof, mutatis mutandis.

In this configuration, tissue-coupling element 128 typically comprises wire 150. For some applications, shaft 122 and tissue-coupling element 128 are integral to one another; for example, shaft 122 and tissue-coupling element 128 may both comprise wire 150, as shown.

Deployment tool 30 is configured to constrain tissue-coupling element 128 while delivering tissue-coupling element 128 through tissue. Typically, during delivery, such as shown in FIG. 5A, deployment tool 30 is configured to hold tissue-coupling element 128 in an elongated, unwound configuration, which may be curvy (such as shown in FIG. 5A) or straight (such as shown in FIG. 1A). Typically, when tissue-coupling element 128 is constrained by the deployment tool, a longitudinal portion of flexible elongate tension member 202, described hereinbelow, runs alongside a portion of wire 150. For some applications, deployment tool 30 comprises a removable driver 201, which comprises a driver head 203 and at least one shaft 205 that is coupled to the driver head. Driver head 203 is removably coupled to anchor head 124 during penetration of tissue-coupling element 128 through tissue, as described hereinbelow. The at least one shaft 205 is configured to controllably detach the driver head from the anchor head. For example, a deployment needle may run through a channel of the at least one shaft; pulling on the needle detaches the driver head from the anchor head.

Figure 5C:
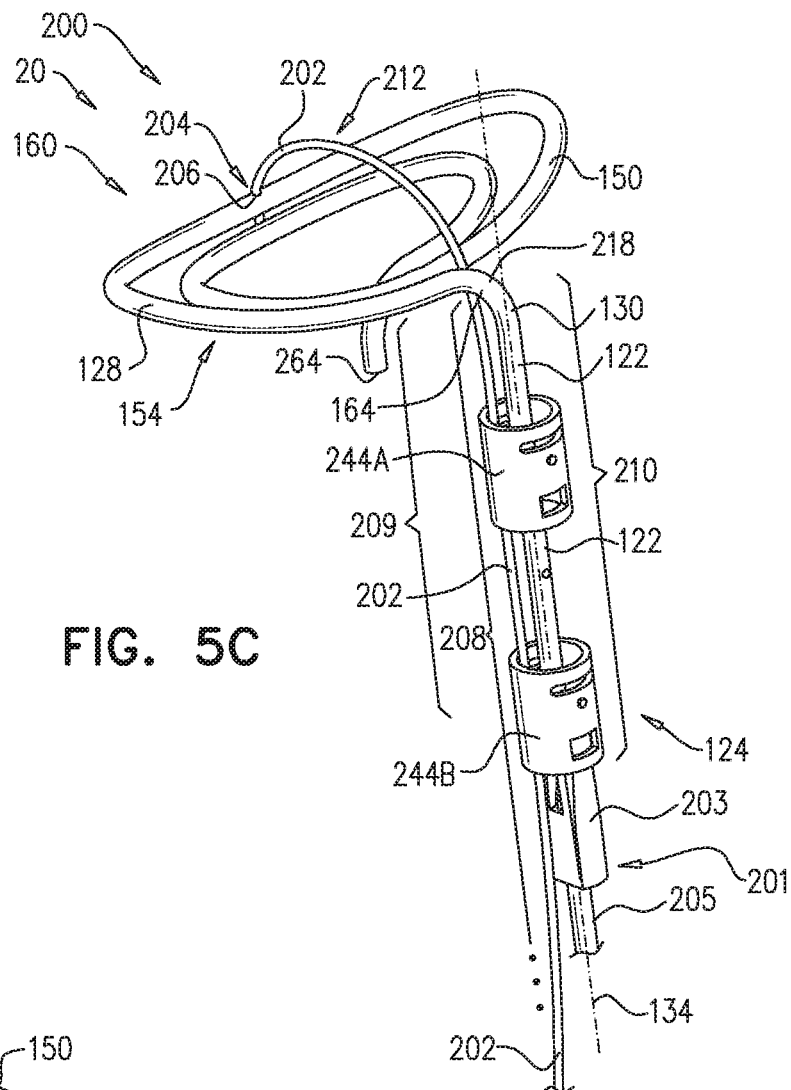
Figure 5D:
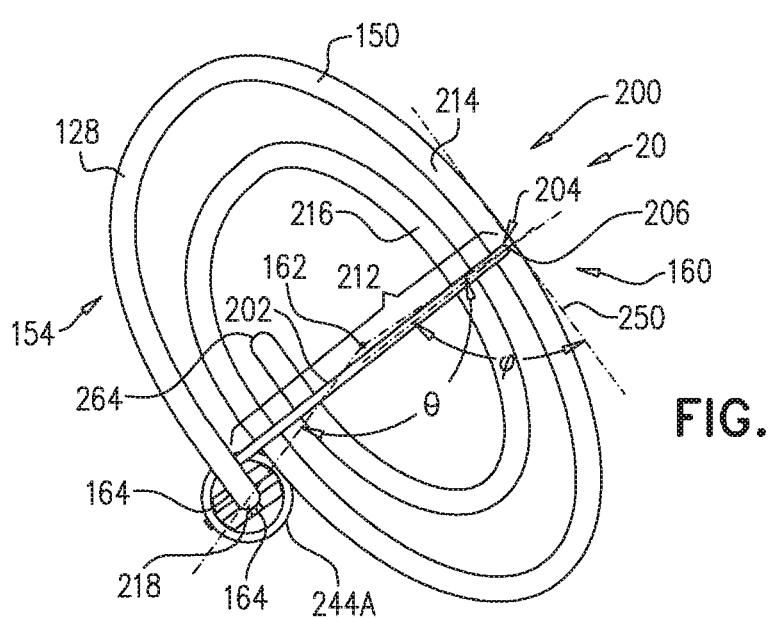

When tissue anchor 200 is unconstrained by deployment tool 30, such as shown in FIGS. 5B-D, wire 150 is shaped as open loop 154 (e.g., a three-dimensional open loop), such as spiral 160 (e.g., a three-dimensional spiral) around center point 162 (labeled in FIGS. 2B and 5D). For some applications, such as shown in FIGS. 5B-D, wire 150 extends from distal end 130 of shaft 122 at radially-outer end 164 of open loop 154 (e.g., spiral 160) (labeled in FIGS. 5C and 5D), when tissue anchor 200 is unconstrained by deployment tool 30. For some applications, wire 150 intersects center point 162 when tissue anchor 200 is unconstrained by deployment tool 30 (configuration not shown), while for other applications, wire 150 does not intersect center point 162 when tissue anchor 200 is unconstrained by deployment tool 30 (as shown). For other applications, such as shown in FIGS. 8A-B, described hereinbelow, wire 150 extends from distal end 130 of shaft 122 at radially-inner end 264 of open loop 154 (e.g., spiral 160).

For some applications, open loop 154 (e.g., spiral 160) has the dimensions described hereinabove with reference to FIGS. 2A-B and/or 3A-B. For some applications, tissue-coupling element 128 has one or more of the characteristics described hereinabove with reference to FIGS. 3A-B.

Tissue anchor 200 further comprises a flexible elongate tension member 202, which includes:
- a distal portion 204 that is fixed to a site 206 on open loop 154 (e.g., spiral 160) (such as by welding, soldering, crimping, and/or knotting),
- a proximal portion 208, which has a longitudinal segment 209 that runs alongside at least a portion 210 of shaft 122 (labeled in FIG. 5C, in which the at least a portion 210 of shaft 122 is the entire length of shaft 122), and
- a crossing portion 212, which (a) is disposed between distal and proximal portions 204 and 208 along flexible elongate tension member 202, and (ii) crosses at least a portion of open loop 154 (e.g., spiral 160) when tissue anchor 200 is unconstrained by deployment tool 30.

Although flexible elongate tension member 202 is fixed to wire 150 of tissue-coupling element 128, flexible elongate tension member 202 is typically distinct from wire 150. In other words, flexible elongate tension member 202 and wire 150 are not two longitudinal portions of a single continuous wire, i.e., are not longitudinally contiguous with each other.

Tension is applied to tissue-coupling element 128 of tissue anchor 200 via flexible elongate tension member 202. The applied tension is resisted by the outward force of open loop 154 (e.g., spiral 160). The applied tension at least partially compresses and stiffens open loop 154 (e.g., spiral 160). This arrangement of tension distribution may overcome any natural tendency of open loop 154 (e.g., spiral 160) to straighten (i.e., unwind) if tension were to be applied along central longitudinal axis 134 via shaft 122, and thus may allow the application of a greater load to open loop 154 (e.g., spiral 160). In addition, this stiffening technique allows open loop 154 (e.g., spiral 160) to be manufactured less stiff than it otherwise would need to be, which facilitates straightening and delivering the tissue anchor, and subsequent stiffening in situ.

Typically, before tension is applied to flexible elongate tension member 202, when tissue anchor 200 is unconstrained by deployment tool 30, flexible elongate tension member 202 is not taut across the at least a portion of open loop 154 (e.g., spiral 160). For example, flexible elongate tension member 202 may arc distally, such as can best be seen in FIG. 5C.

Typically, tissue anchor 200 is configured to allow relative axial motion between the at least a portion 210 of shaft 122 and longitudinal segment 209 of proximal portion 208 of flexible elongate tension member 202 when tissue anchor 200 is unconstrained by deployment tool 30 (as flexible elongate tension member 202 is tensioned and pulls on tissue-coupling element 128, tissue anchor 200 becomes progressively more constrained by flexible elongate tension member 202; the relative axial motion nevertheless remains possible). In other words, longitudinal segment 209 of proximal portion 208 of flexible elongate tension member 202 is axially moveable with respect to the at least a portion 210 of shaft 122 when tissue anchor 200 is unconstrained by deployment tool 30. Such axial motion allows tension to be applied to flexible elongate tension member 202 without also being applied to shaft 122, and allows open loop 154 (e.g., spiral 160) to be unwound and flexible elongate tension member 202 to be disposed alongside a portion of flexible elongate tension member 202, as shown in FIG. 5A (in which deployment tool 30 constrains both constrain tissue-coupling element 128 and flexible elongate tension member 202). Typically, longitudinal segment 209 of proximal portion 208 of flexible elongate tension member 202 is coupled in sliding communication with the at least a portion 210 of shaft 122, when tissue anchor 200 is unconstrained by deployment tool 30. For some applications, tissue anchor 200 comprises one or more annular elements, which are disposed around the at least a portion of shaft 122, and couple flexible elongate tension member 202 in the sliding communication with the at least a portion 210 of shaft 122, when tissue anchor 200 is unconstrained by deployment tool 30. For example, the annular elements may comprise one or more collars 244, described hereinbelow, loops, or rings.

For some applications, flexible elongate tension member 202 is not fixed to any portion of open loop 154 (e.g., spiral 160) beyond 2 mm from site 206 on open loop 154 (e.g., spiral 160), measured when tissue anchor 200 is unconstrained by deployment tool 30. Alternatively or additionally, when tissue anchor 200 is unconstrained by deployment tool 30, flexible elongate tension member 202 is not fixed to any portion of open loop 154 (e.g., spiral 160) beyond a distance from site 206 on open loop 154 (e.g., spiral 160), which distance equals 30% of greatest lateral dimension D3 of open loop 154 (e.g., spiral 160) of tissue-coupling element 128, measured perpendicular to central longitudinal axis 134 (labeled in FIG. 2A). For some applications, flexible elongate tension member 202 is fixed to open loop 154 (e.g., spiral 160) only at site 206 on open loop 154 (e.g., spiral 160). Alternatively, a distal portion of flexible elongate tension member 202 beyond site 206 is fixed to open loop 154 (e.g., spiral 160), such as described hereinbelow with reference to FIGS. 9E and 9F.

Typically, when tissue anchor 200 is unconstrained by deployment tool 30, the at least a portion of open loop 154 (e.g., spiral 160) crossed by crossing portion 212 has a length that equals at least 33% of greatest lateral dimension D3 of open loop 154 (e.g., spiral 160) of tissue-coupling element 128, measured perpendicular to central longitudinal axis 134 (labeled in FIG. 2A), e.g., at least 50% of greatest lateral dimension D3, such as at least 75% of greatest lateral dimension D3, e.g., at least 90% of greatest lateral dimension D3.

For some applications, as shown, site 206 is on an outermost turn 214 of open loop 154 (e.g., spiral 160) (labeled in FIG. 5D), when tissue anchor 200 is unconstrained by deployment tool 30. For some other applications, site 206 is on a second-to-outermost turn 216 of open loop 154 (e.g., spiral 160) (labeled in FIG. 5D), when tissue anchor 200 is unconstrained by deployment tool 30 (configuration not shown).

Typically, a radius of flexible elongate tension member 202 is less than a radius of wire 150, such as less than 50% of the radius of wire 150. As mentioned above with reference to FIGS. 1B-C and 2A-C, for some applications a cross-sectional area of wire 150 is at least 0.09 mm2 (such as at least 0.18 mm2), no more than 3 mm2 (e.g., no more than 2.9 mm2), and/or between 0.09 mm2 (such as 0.18 mm2) and 3 mm2 (e.g., 2.9 mm2). For some applications, flexible elongate tension member 202 comprises metal, such as a metal alloy, e.g., Nitinol. For some applications, flexible elongate tension member 202 comprises radiopaque sections or is radiopaque, to enable observation of the relative movement when tensioning.

For some applications, site 206 on open loop 154 (e.g., spiral 160) is a first site 206 on open loop 154 (e.g., spiral 160), and, when tissue anchor 200 is unconstrained by deployment tool 30 and flexible elongate tension member 202 is tensioned straight, (a) wire 150 extends from distal end 130 of shaft 122 at a second site 218 on open loop 154 (e.g., spiral 160), and (b) if tissue-coupling element 128 and flexible elongate tension member 202 were to be projected onto plane 136 that is perpendicular to central longitudinal axis 134, an angle θ (theta) between the first and the second sites, having a vertex 242 at center point 162, would be between 130 and 180 degrees, such as between 150 and 180 degrees, e.g., between 170 and 180 degrees (labeled in FIG. 5D). For some applications, as shown, second site 218 is at radially-outer end 164 of open loop 154 (e.g., spiral 160).

Alternatively or additionally, for some applications, as labeled in FIG. 5D, when tissue anchor 200 is unconstrained by deployment tool 30 and flexible elongate tension member 202 is tensioned straight, if tissue-coupling element 128 and flexible elongate tension member 202 were to be projected onto plane 136 that is perpendicular to central longitudinal axis 134, an angle φ (phi) between (a) flexible elongate tension member 202 and (b) a tangent 250 to open loop 154

(e.g., spiral 160) at site 206 would be between 45 and 90 degrees, such as between 70 and 90 degrees, e.g., 90 degrees.

Figure 6A:
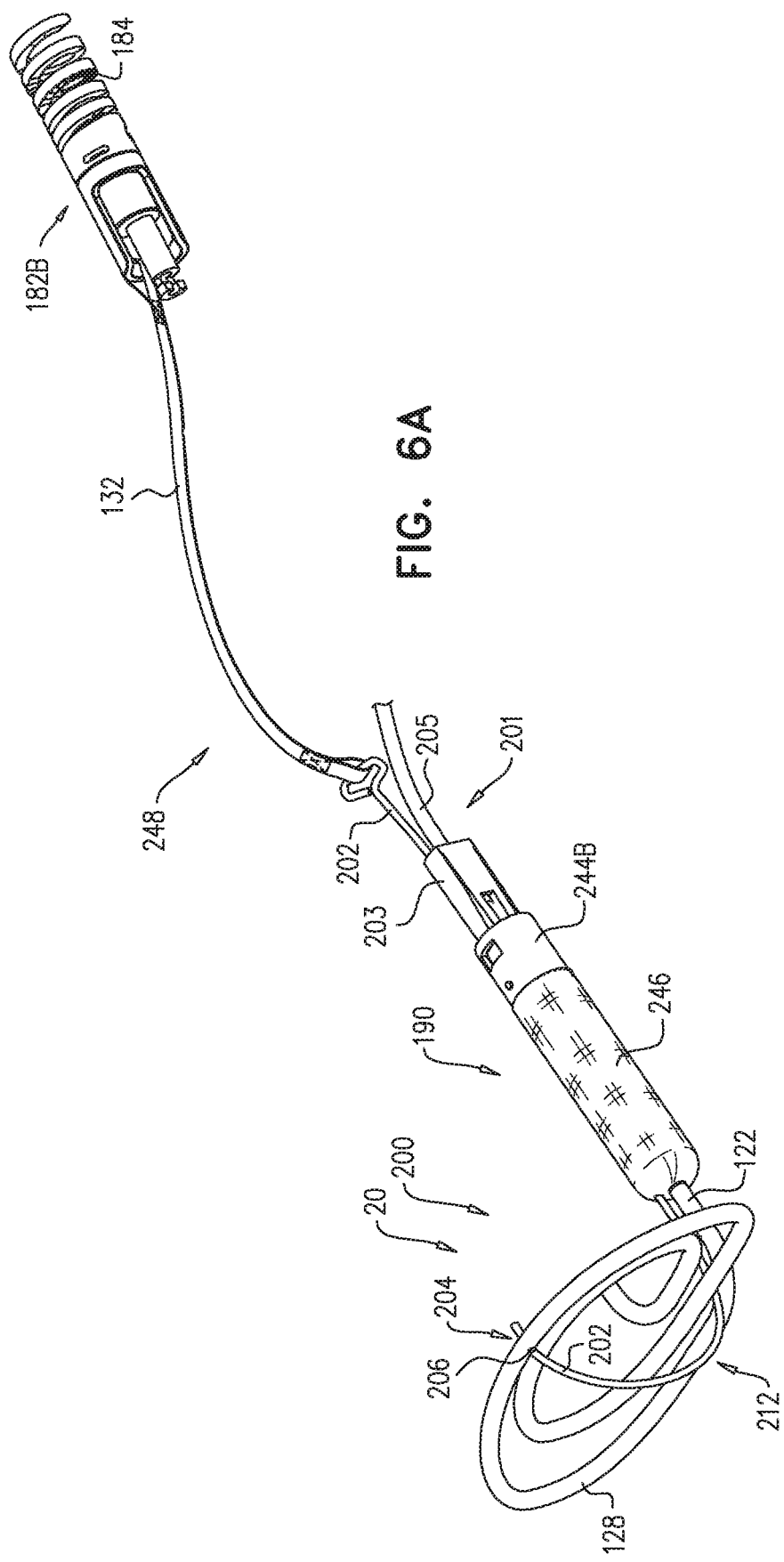

As mentioned above with reference to FIGS. 1A-D and 4A-B, for some application shaft 122 comprises sealing element 190. For some applications, sealing element 190 one or more collars 244 disposed around shaft 122, and, typically, a sleeve 246 that couples the collars 244 together. Sleeve 246 defines a lumen having proximal and distal ends. The flexible elongate tension member 202 slidingly passes through the lumen and its ends. (Sleeve 246 is shown in FIGS. 5A and 6A-B; for clarity of illustration, sleeve 246 is shown as transparent in FIG. 5B, and is not shown in FIG. 5C.) In this configuration, sealing element 190 is typically sized and shaped to be inserted into the incision through the heart wall, and to provide a blood-tight seal. Sleeve 246, if provided, occludes blood flow to provide the seal. For some applications, sleeve 246 promotes hemostasis. Optionally, filament or fiber is provided within sleeve 246 to promote hemostasis. For some applications, collars 244 comprise a distal guide collar 244A and a proximal driver collar 244B, which optionally is a component of or serves as head 124. For some applications, a proximal end of shaft 122 is disposed within proximal driver collar 244B, as shown. For some applications, one or more of collars 244 are radiopaque or comprise a radiopaque marker. For example, sleeve 246 may comprise Dacron, and/or may be coated and/or woven to facilitate clotting.

For other applications, sealing element 190 has the configuration described hereinabove with reference to FIGS. 1A-D and 4A-B, or the configuration described hereinbelow with reference to FIGS. 9A-F or FIG. 9G.

For some applications, a proximally-facing surface defined by tissue-coupling element 128 is convex when tissue anchor 200 is unconstrained by deployment tool 30, such as shown in FIGS. 2C and 5B-C. For other applications, a proximally-facing surface defined by tissue-coupling element 128 is concave when tissue anchor 200 is unconstrained by deployment tool 30, such as shown in FIG. 2B.

For some applications, one or more tethers 132 are provided, which are configured to be coupled to tissue anchor 200. Typically, the one or more tethers 132 are fixed to flexible elongate tension member 202, typically to proximal portion 208 of the tension member, such as at or near (e.g., within 1 cm of) a proximal end of proximal portion 208. This is unlike the configuration described hereinabove with reference to FIGS. 1A-D, in which head 124 of tissue anchor 120 is coupled to the one or more tethers. In the present configuration, when tension is applied to the one or more tethers, the tension is transmitted to flexible elongate tension member 202, rather than to shaft 122 via head 124. In these applications, the one or more tethers are (a) fixed to the second tissue anchor and (b) not fixed to shaft 122 of first tissue anchor 200.

For some applications, a radially-inner end 264 of open loop 154 (e.g., spiral 160) is bent proximally, such as can be best seen in FIG. 5C. Because of the bend, radially-inner end 264 may help tissue-coupling element 128 resist rotation and uncoiling.

Reference is now made to FIGS. 6A-B, which are schematic illustrations of two configurations of a tissue anchor system 248, in accordance with respective applications of the present invention. In these applications, tissue anchor 200 is a first tissue anchor 182A of tissue anchor system 248, which further comprises (a) a second tissue anchor 182B, which is separate and distinct first tissue anchor 182A, and (b) the one or more tethers 132, which are configured to couple (i) flexible elongate tension member 202 of first tissue anchor 182A to (ii) second tissue anchor 182B. For some applications, one of the one or more tethers 132 is fixed to (a) flexible elongate tension member 202 of first tissue anchor 182A to (b) second tissue anchor 182B.

For some applications, such as shown in FIG. 6A, second tissue anchor 182B comprises helical tissue-coupling element 184. For example, second tissue anchor 182B may implement techniques described in PCT Publication WO 2014/108903, which is incorporated herein by reference. For other applications, such as shown in FIG. 6B, second tissue anchor 182B comprises stent 186. For example, second tissue anchor 182B may implement techniques described in one or more of the following applications, which are incorporated herein by reference: US Patent Application Publication 2011/0184510, US Patent Application Publication 2012/0035712, US Patent Application Publication 2013/0018459, US Patent Application Publication 2013/0046380, PCT Publication WO 2014/141239, and/or the patents and patent application publications incorporated hereinbelow by reference.

Figure 7B:
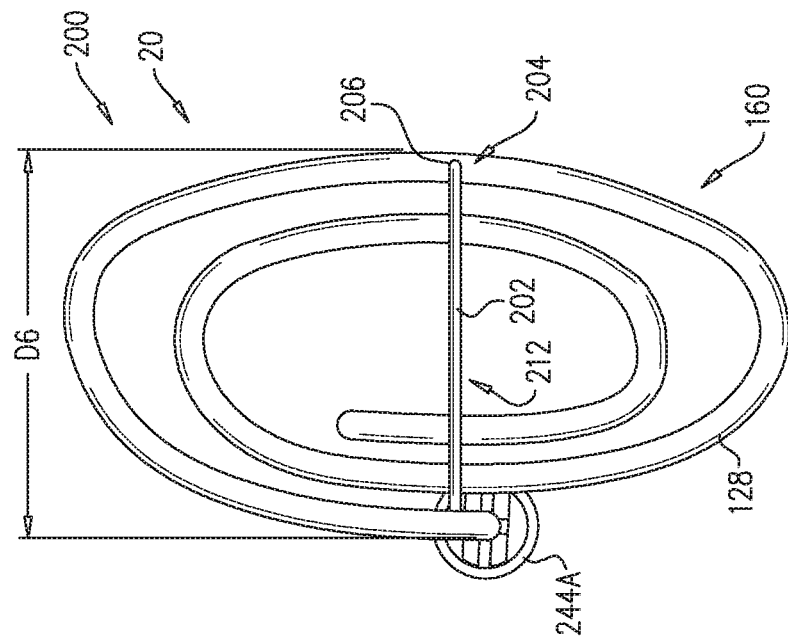
FIGS. 7A-B are schematic illustrations of an open loop of the tissue anchor of FIGS. 5A-D unconstrained and under tension, respectively, in accordance with an application of the present invention.
Figure 7A:
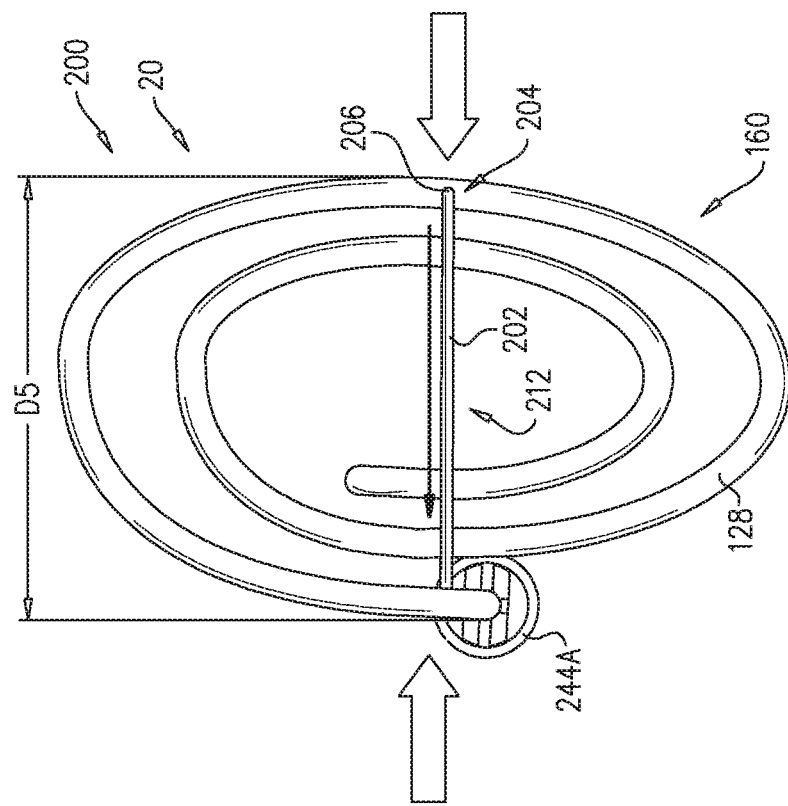

Reference is now made to FIGS. 7A-B, which are schematic illustrations of open loop 154 (e.g., spiral 160) of tissue anchor 200 unconstrained by deployment tool 30 and under tension, respectively, in accordance with an application of the present invention. In the state shown in FIG. 7A, tissue anchor 200 (and open loop 154 (e.g., spiral 160) thereof) is unconstrained by deployment tool 30. In this state, open loop 154 (e.g., spiral 160) has a first outer dimension D5, measured in a direction parallel to flexible elongate tension member 202. After tension is applied to flexible elongate tension member 202, flexible elongate tension member 202 becomes more narrow in the direction of flexible elongate tension member 202, such that open loop 154 (e.g., spiral 160) has a second outer dimension D6, measured in a direction parallel to flexible elongate tension member 202, which is less than first outer dimension D5, e.g., no more than 90% of D5, such as no more than 80% of D5, e.g., no more than 70% of D5, no more than 50% of D5, or no more than 20% of D5. For some applications, the force applied to flexible elongate tension member 202 to achieve this reduction is between 2 and 50 N, such as between 5 and 20 N, e.g., 5 N, 7 N, 10 N, 20 N, or 30 N. The amount of force is dependent on the radius of wire 150, and may increase as a power of the radius, such as a third or fourth power of the radius. For some applications, a smallest radius of wire 150 is chosen that is able to withstand between 5 and 20 N of force.

Reference is now made to FIGS. 8A and 8B, which are schematic illustrations of two configurations of a tissue anchor 258, in accordance with respective applications of the present invention. Tissue anchor 258 is one implementation of tissue anchor 20, described above. Other than as described below, tissue anchor 258 is generally similar to tissue anchor 200, described hereinabove with reference to FIGS. 5A-7B, and may implement any of the features thereof, mutatis mutandis. In addition, tissue anchor 258 may implement any of the features of tissue anchor 120, described hereinabove with reference to FIGS. 1A-4B, mutatis mutandis.

Tissue-coupling element 128 of tissue anchor 258 comprises wire 150, which is shaped as an open loop 256, e.g., a spiral 260. Wire 150 extends from distal end 130 of shaft 122 at a radially-inner end 264 of open loop 256 (e.g., spiral 260), when tissue anchor 220 is unconstrained by deployment tool 30. This is unlike the typical configurations of open loop 154 (e.g., spiral 160), described hereinabove, in which wire 150 extends from distal end 130 of shaft 122 at radially-outer end 164 of open loop 154 (e.g., spiral 160). In the present configurations, when tissue anchor 220 is unconstrained by deployment tool 30, radially-inner end 264 of open loop 256 (e.g., spiral 260) is typically disposed within 15 mm of center point 162, such as coinciding with center point 162.

In the configuration shown in FIG. 8A, tissue anchor 258 comprises exactly one flexible elongate tension member 202, which includes:
- distal portion 204 that is fixed to site 206 on open loop 256 (e.g., spiral 260),
- longitudinal segment 209 of proximal portion 208 that runs alongside the at least a portion 210 of shaft 122 (labeled in FIG. 5C), and
- crossing portion 212, which (a) is disposed between distal and proximal portions 204 and 208 along flexible elongate tension member 202, and (ii) crosses at least a portion of open loop 256 (e.g., spiral 260) when tissue anchor 258 is unconstrained by deployment tool 30.

For some applications, as shown, site 206 is on outermost turn 214 of open loop 256 (e.g., spiral 260), when tissue anchor 258 is unconstrained by deployment tool 30. Flexible elongate tension member 202 may implement any of the features described hereinabove with reference to FIGS. 5A-7B, mutatis mutandis.

In the configuration shown in FIG. 8B, tissue anchor 258 comprises two flexible elongate tension members 202A and 202B, which include:
- respective distal portions 204A and 204B that are fixed to respective sites 206A and 206B on open loop 256 (e.g., spiral 260),
- respective proximal portions 208, which have respective longitudinal segments that run alongside the at least a portion 210 of shaft 122 (labeled in FIG. 5C); these proximal portions may join one another at some point along the proximal portions (such as within or proximal to proximal driver collar 244B), or may otherwise be coupled to one another along respective portion of the proximal portions, and
- respective crossing portions 212A and 212B, which (a) are disposed between respective distal and proximal portions 204A and 208B along flexible elongate tension members 202A and 202B, respectively, and (ii) cross at least respective portions of open loop 256 (e.g., spiral 260) when tissue anchor 258 is unconstrained by deployment tool 30.

For some applications, as shown, sites 206A and 206B are on outermost turn 214 of open loop 256 (e.g., spiral 260), when tissue anchor 258 is unconstrained by deployment tool 30. Flexible elongate tension members 202A and 202B may implement any of the features described hereinabove with reference to FIGS. 5A-7B, mutatis mutandis.

Reference is now made to FIGS. 9A-D, which are schematic illustrations of a tissue anchor 300, in accordance with an application of the present invention. Tissue anchor 300 is one implementation of tissue anchor 20, described above. Other than as described below, tissue anchor 300 is generally similar to tissue anchor 200, described hereinabove with reference to FIGS. 5A-D, and may implement any of the features thereof, mutatis mutandis. For some applications, tissue anchor 300 is implemented using the configuration of FIG. 6A or 6B, mutatis mutandis.

Figure 9A:
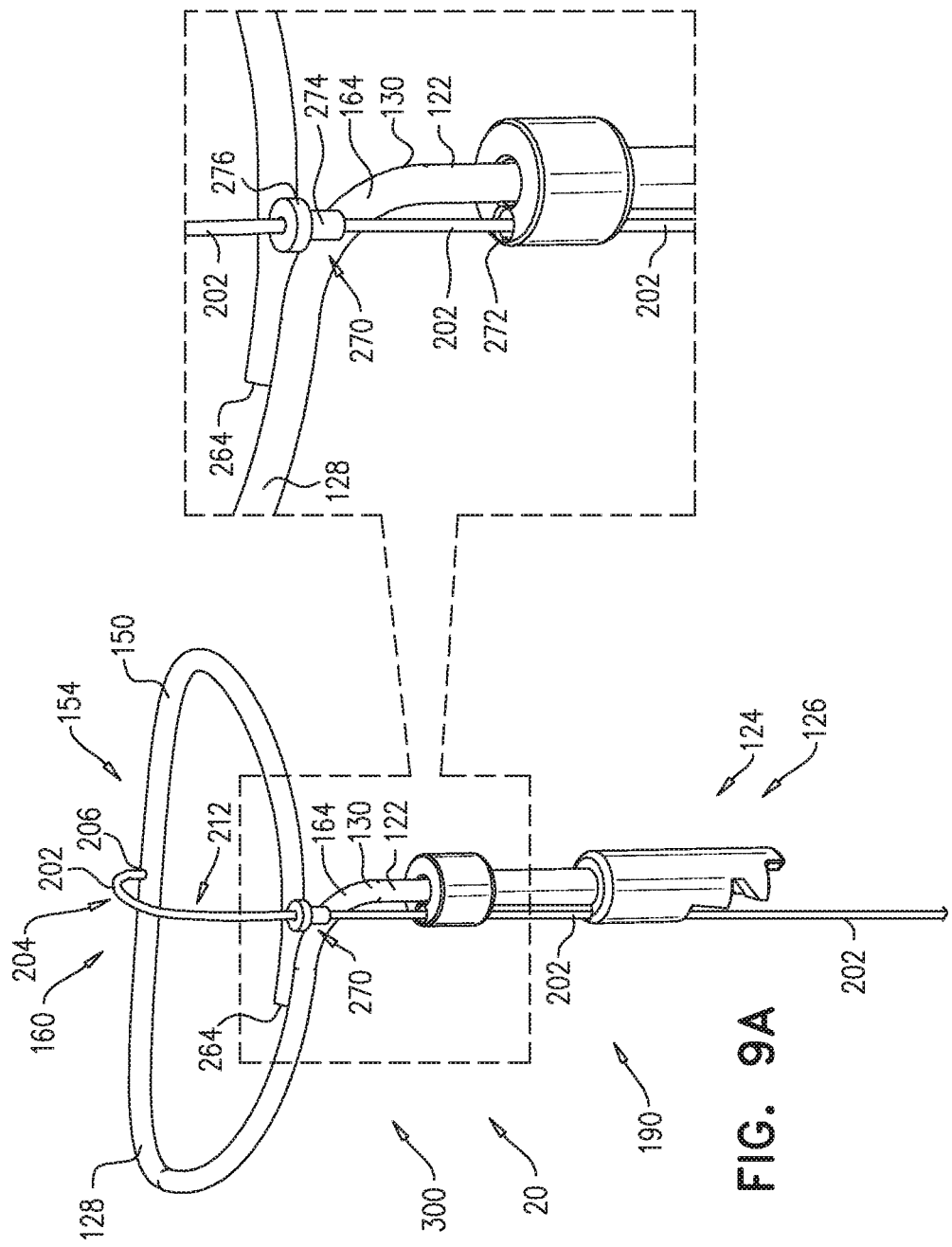
FIGS. 9A-D are schematic illustrations of another tissue anchor, in accordance with an application of the present invention.
Figure 9B:
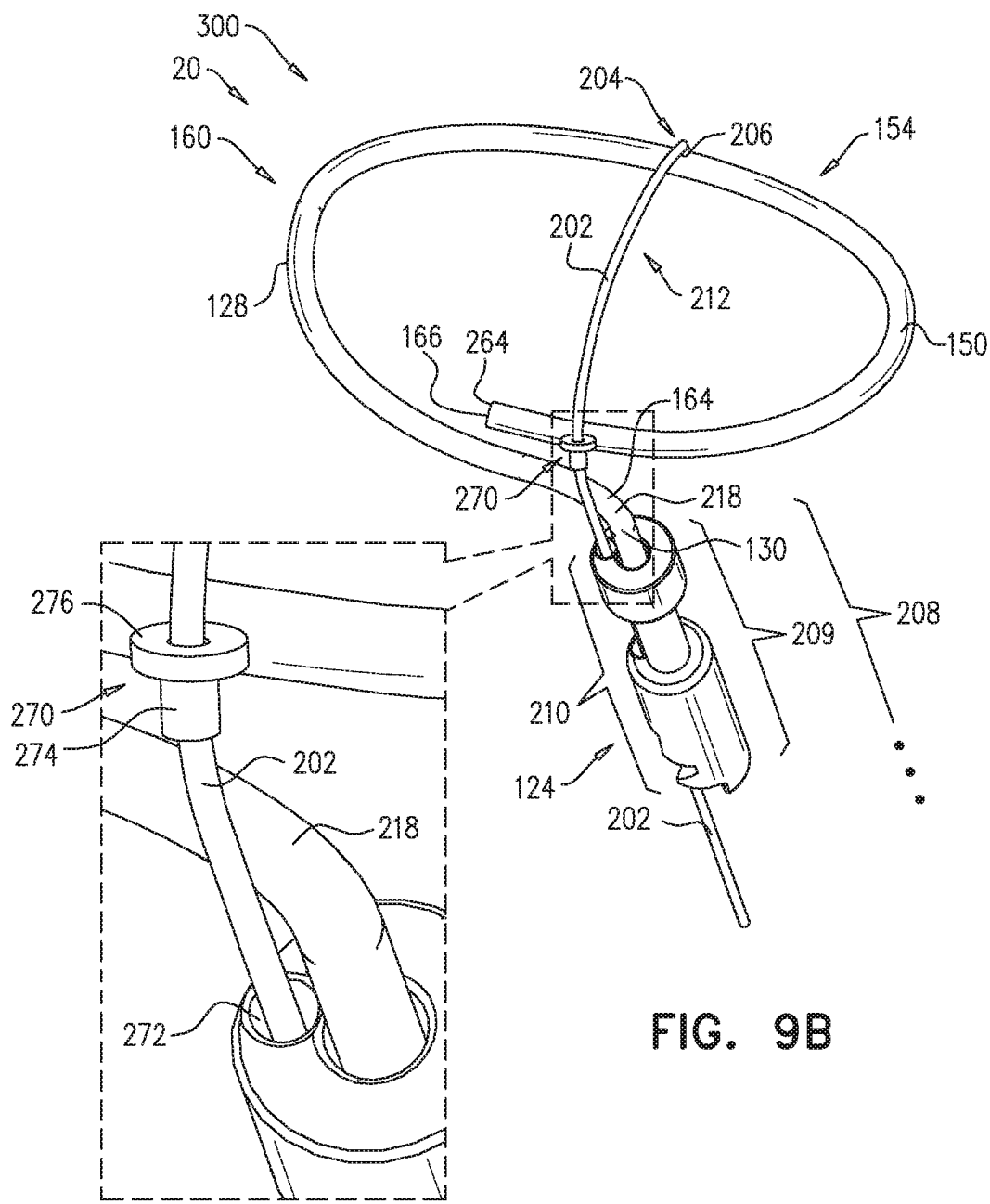
Figure 9C:
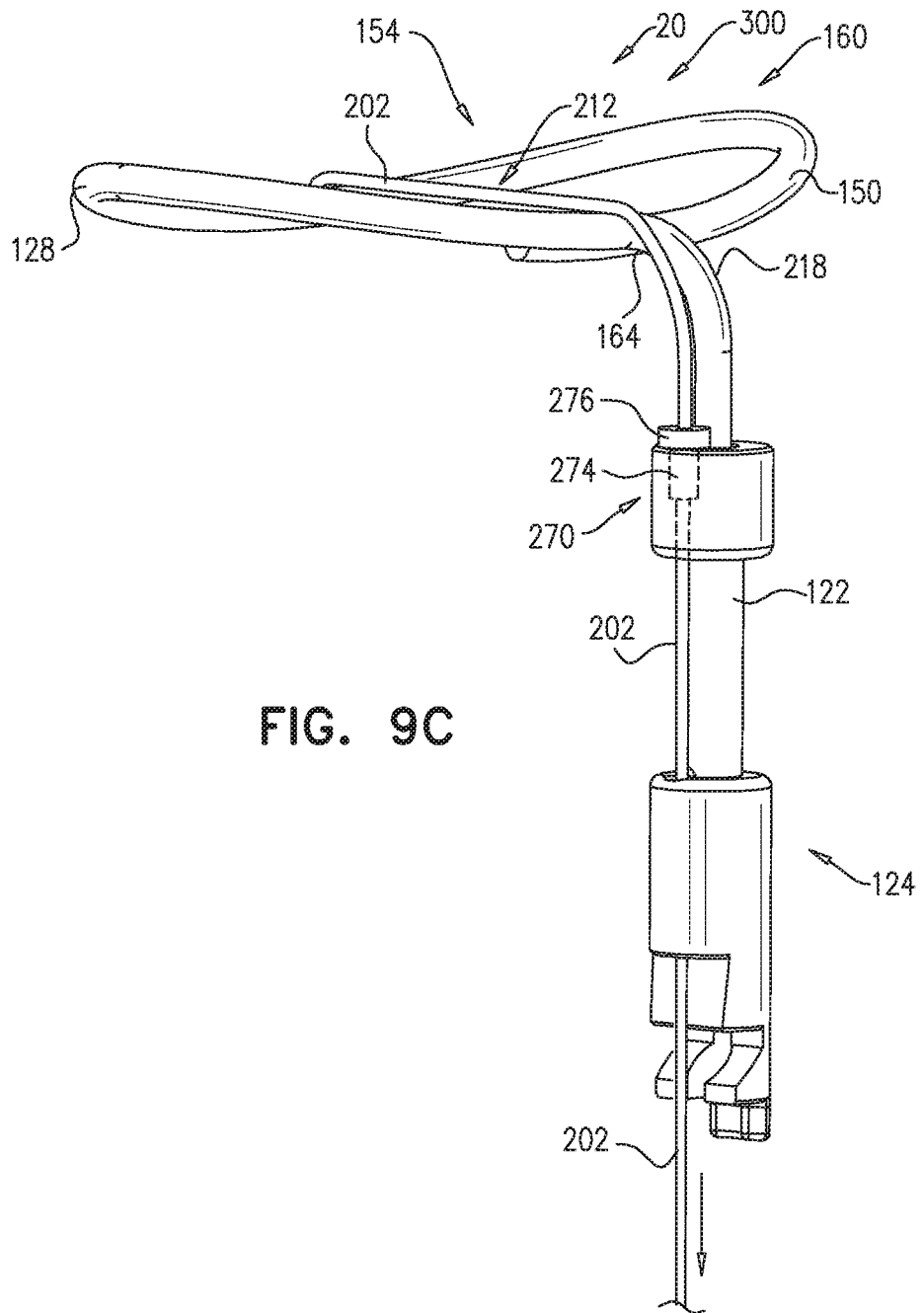

When tissue anchor 300 is unconstrained by deployment tool 30, such as shown in FIGS. 9A-C, wire 150 is shaped as open loop 154 (e.g., a three-dimensional open loop) around center point 162 (labeled in FIGS. 2B and 5D), and, optionally, as spiral 160 (e.g., a three-dimensional spiral) around center point 162 (labeled in FIGS. 2B and 5D). For some applications, such as shown in FIGS. 9A-C, wire 150 extends from distal end 130 of shaft 122 at radially-outer end 164 of open loop 154 (and, optionally, spiral 160) (labeled in FIG. 9A), when tissue anchor 300 is unconstrained by deployment tool 30. For some applications, open loop 154 (and, optionally, spiral 160) has the dimensions described hereinabove with reference to FIGS. 2A-B and/or 3A-B. For some applications, tissue-coupling element 128 has one or more of the characteristics described hereinabove with reference to FIGS. 3A-B. For some applications, the proximally-facing surface defined by tissue-coupling element 128 is generally flat, when tissue anchor 300 is unconstrained by deployment tool 30 (configuration not shown). Optionally, upon coming into full contact with the external surface of the heart, the proximally-facing surface defined by the tissue-coupling element may assume a concave shape conforming to the convex shape of the external surface of the heart.

In the configuration shown in FIGS. 9A-D, tissue anchor 300 further comprises a flexible elongate tension member 202, which includes:
- distal portion 204 that is fixed to site 206 on open loop 154 (such as by welding, soldering, crimping, and/or knotting, and/or as described hereinbelow with reference to FIG. 9E and/or FIG. 9F),
- proximal portion 208, which has longitudinal segment 209 that runs alongside at least portion 210 of shaft 122 (labeled in FIG. 9B, in which the at least a portion 210 of shaft 122 is the entire length of shaft 122), and
- crossing portion 212, which (a) is disposed between distal and proximal portions 204 and 208 along flexible elongate tension member 202, and (ii) crosses at least a portion of open loop 154 when tissue anchor 300 is unconstrained by deployment tool 30.

Although flexible elongate tension member 202 is fixed to wire 150 of tissue-coupling element 128, flexible elongate tension member 202 is typically distinct from wire 150. In other words, flexible elongate tension member 202 and wire 150 are not two longitudinal portions of a single continuous wire, i.e., are not longitudinally contiguous with each other.

Tension is applied to tissue-coupling element 128 of tissue anchor 300 via flexible elongate tension member 202. The applied tension is resisted by the outward force of open loop 154. The applied tension at least partially compresses and stiffens open loop 154. This arrangement of tension distribution may overcome any natural tendency of open loop 154 to straighten (i.e., unwind) if tension were to be applied along central longitudinal axis 134 via shaft 122, and thus may allow the application of a greater load to open loop 154.

Typically, before tension is applied to flexible elongate tension member 202, when tissue anchor 300 is unconstrained by deployment tool 30, flexible elongate tension member 202 is not taut across the at least a portion of open loop 154. For example, flexible elongate tension member 202 may arc distally, such as can best be seen in FIG. 9A.

Typically, tissue anchor 300 is configured to allow relative axial motion between the at least a portion 210 of shaft 122 and longitudinal segment 209 of proximal portion 208 of flexible elongate tension member 202 when tissue anchor 300 is unconstrained by deployment tool 30. Such axial motion allows tension to be applied to flexible elongate tension member 202 without also being applied to shaft 122, and allows open loop 154 to be unwound and flexible elongate tension member 202 to be disposed alongside a portion of flexible elongate tension member 202, as shown in FIG. 9A. Typically, longitudinal segment 209 of proximal portion 208 of flexible elongate tension member 202 is coupled in sliding communication with the at least a portion 210 of shaft 122, when tissue anchor 300 is unconstrained by deployment tool 30. For some applications, tissue anchor 300 comprises one or more annular elements, which are disposed around the at least a portion of shaft 122, and couple flexible elongate tension member 202 in the sliding communication with the at least a portion 210 of shaft 122, when tissue anchor 300 is unconstrained by deployment tool 30. For example, the annular elements may comprise one or more collars, loops, or rings. Shaft 122 (e.g., the collars) is shaped such that flexible elongate tension member 202 runs generally parallel to central longitudinal axis 134 of shaft 122.

For some applications, as shown, site 206 is on an outermost turn of open loop 154, when tissue anchor 300 is unconstrained by deployment tool 30. For some other applications, site 206 is on a second-to-outermost turn of open loop 154, when tissue anchor 300 is unconstrained by deployment tool 30 (configuration not shown).

Typically, a radius of flexible elongate tension member 202 is less than a radius of wire 150, such as less than 50% of the radius of wire 150. Flexible elongate tension member 202 and/or wire 150 may have any of the characteristics described hereinabove with reference to FIGS. 2A-C, 3A-B, and/or 5A-D, including dimensions and relative arrangement with respect to each other.

For some applications, one or more tethers 132 are provided, which are configured to be coupled to tissue anchor 300. Typically, the one or more tethers 132 are fixed to flexible elongate tension member 202, typically to proximal portion 208 of the tension member, such as at or near (e.g., within 1 cm of) a proximal end of proximal portion 208. When tension is applied to the one or more tethers, the tension is transmitted to flexible elongate tension member 202, rather than to shaft 122 via head 124.

For some applications, head 124 is shaped so as to define a passage 272 in which proximal portion 208 of flexible elongate tension member 202 is slidably disposed. Flexible elongate tension member 202 comprises a locking stopper 270, which is axially fixed to proximal portion 208 or crossing portion 212 of flexible elongate tension member 202. Locking stopper 270 and passage 272 are sized and shaped such that the size and shape of passage 272 prevent proximal movement of locking stopper 270 past passage 272. Optionally, locking stopper 270 engages passage 272 (as shown). For some applications, passage 272 is a channel through a portion of head 124 (such as through one or more collars of head 124) (as shown), while for other applications, passage 272 is a groove (e.g., a U-shaped groove) (configuration not shown). For some applications, locking stopper 270 is shaped so as to define a base 274 and a flange 276. The flange is too large to pass through passage 272, while base 274 may or may not be too large to enter the passage. For some applications, locking stopper 270 is manufactured as a separate element that is fixed to flexible elongate tension member 202, such as by crimping, welding, or soldering. For other applications, locking stopper 270 is integral to flexible elongate tension member 202.

For some applications, passage 272 extends to a distal end of head 124 (as shown), while for other applications, passage 272 is disposed more proximally in head 124, such as near a proximal end of head 124 (configuration not shown). Typically, locking stopper 270 is axially fixed to proximal portion 208 or crossing portion 212 of flexible elongate tension member 202 at a distance of at least 7 mm, no more than 22 mm, and/or between 7 and 22 mm from site 206 on the open loop, measured along flexible elongate tension member 202 (i.e., measured along the curvature of flexible elongate tension member 202 if it is curved, such as shown in FIGS. 9A-B). Alternatively or additionally, for some applications, if tissue-coupling element 128 were straightened in an elongated configuration, for example by being disposed in deployment tool 30 such as shown in FIG. 1A mutatis mutandis, locking stopper 270 would be a distance of at least 7 mm, no more than 12 mm, and/or between 7 and 12 mm (e.g., 10 mm) from passage 272. Alternatively or additionally, for some applications, when tissue anchor 300 is unconstrained by deployment tool 30 (and flexible elongate tension member 202 is curved, such as shown in FIGS. 9A-B), locking stopper 270 is disposed at a distance of at least 7 mm, no more than 12 mm, and/or between 7 and 12 mm (e.g., 10 mm) from passage 272. For some applications, when sufficient tension is applied to flexible elongate tension member 202 straighten flexible elongate tension member 202 but not compress open loop 154, locking stopper 270 moves between 5 and 8 mm toward passage 272, such that locking stopper 270 is disposed at a distance of at least 2 mm, no more than 5 mm, and/or between 2 and 5 mm (e.g., 10 mm) from passage 272.

Figure 9D:
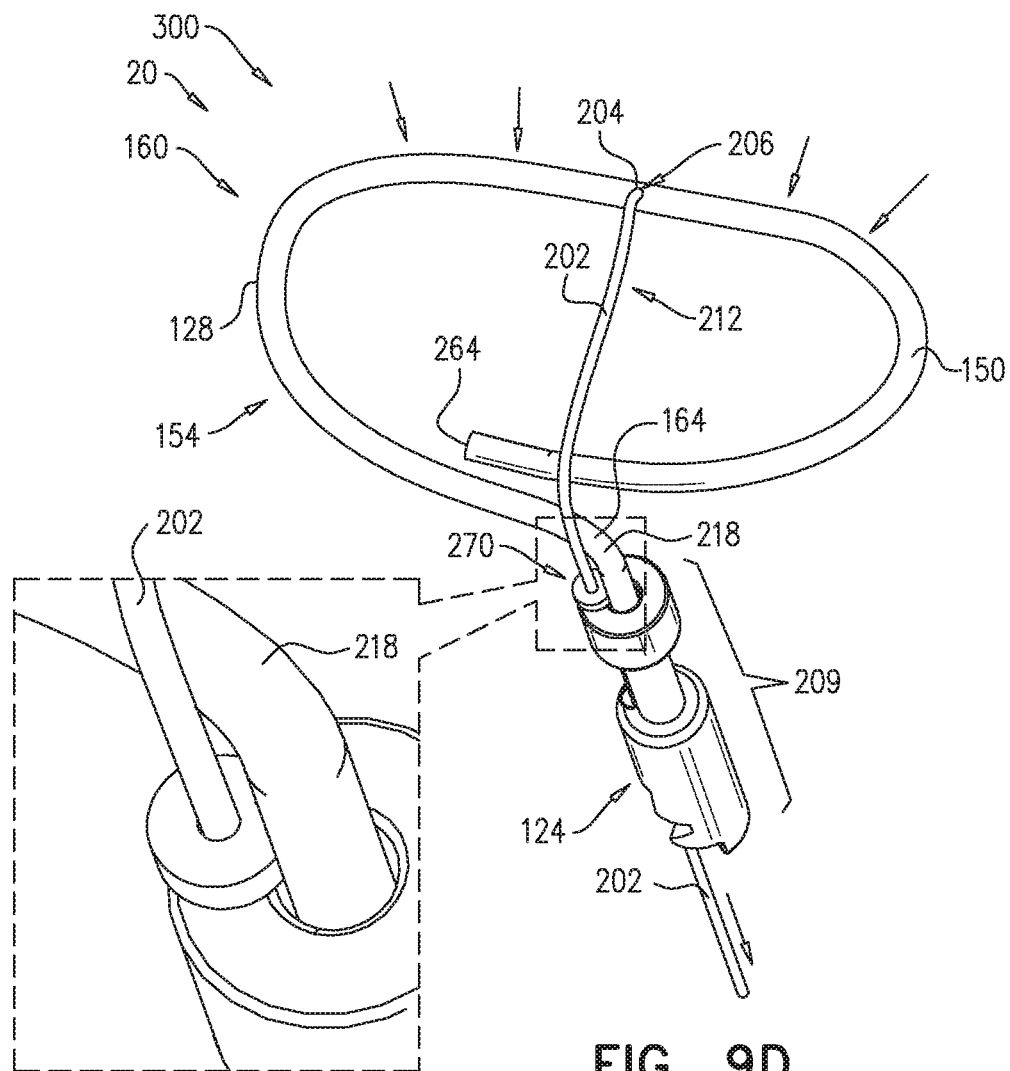

As shown in FIG. 9C-D, tension is applied to tissue-coupling element 128 of tissue anchor 200 via flexible elongate tension member 202. The applied tension is resisted by the outward force of open loop 154. The applied tension at least partially compresses and stiffens open loop 154. This arrangement of tension distribution may overcome any natural tendency of open loop 154 to straighten (i.e., unwind) if tension were to be applied along central longitudinal axis 134 via shaft 122, and thus may allow the application of a greater load to open loop 154. The tension applied to tissue-coupling element 128 thus locks open loop 154 into a desired shape.

Locking stopper 270 limits the total load that can be applied to open loop 154 by flexible elongate tension member 202, thereby reducing excessive, unnecessary strain on open loop 154. For example, the first 1.5 to 5 N of force applied to flexible elongate tension member 202 may sufficiently deform open loop 154 and engage locking stopper 270. Additional load (tension) that is applied by flexible elongate tension member 202 pulls on the entire anchor 300, and does not further increase the load applied across open loop 154 to site 206, and thus does not further compress the open loop. As described hereinbelow with reference to FIGS. 14D and 15A-C, such tension may be applied to pull anchor 300 closer to another tissue anchor, in order to facilitate repair of an atrioventricular valve of the subject, such as tricuspid valve 504.

These techniques thus allow the use of relatively flexible tissue-coupling element, in order to not generate too much outward force inside a delivery tube, which might make axial movement of the tissue-coupling element in the delivery tube difficult or impossible. The tissue-coupling element is tensioned upon delivery, thereby changing its shape and providing a strong tissue-coupling element that cannot unwind easily, and thus remains coupled to the tissue. In addition, minimizing the load on attachment site 206 provides a mechanical advantage that increases the durability of the device under higher loads.

As mentioned above, open loop 154 may have more than one turn and less than 1.5 turns, such as more than one turn, e.g., more than 1.01 turns (363.6 degrees), such as more than 1.02 turns (367.2 degrees), and/or less than 1.25 turns (450 degrees) (one turn equals 360 degrees). Providing open loop 154 with more than one turn, rather than exactly one turn or less than one turn, prevents crossing portion 212 from sliding down off of open loop 154 and onto shaft 122 when tension is applied to crossing portion 212. Such sliding might result in crossing portion 212 cutting into tissue of the heart.

Figure 9E:
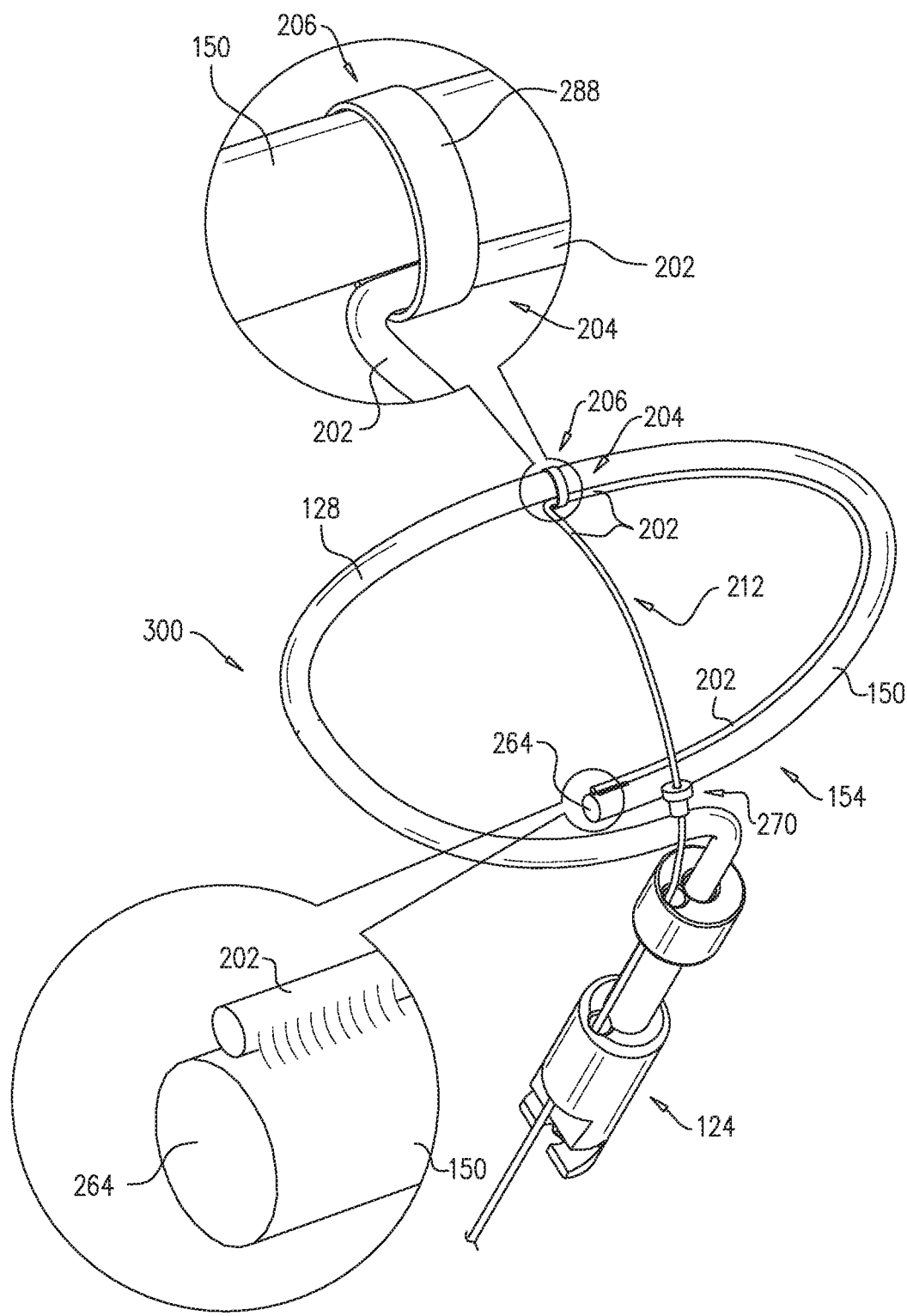
FIGS. 9E and 9F are schematic illustrations of alternative ways to fix a flexible elongate tension member to a site of an open loop of the tissue anchor of FIGS. 9A-D, in accordance with respective applications of the present invention.
Figure 9F:
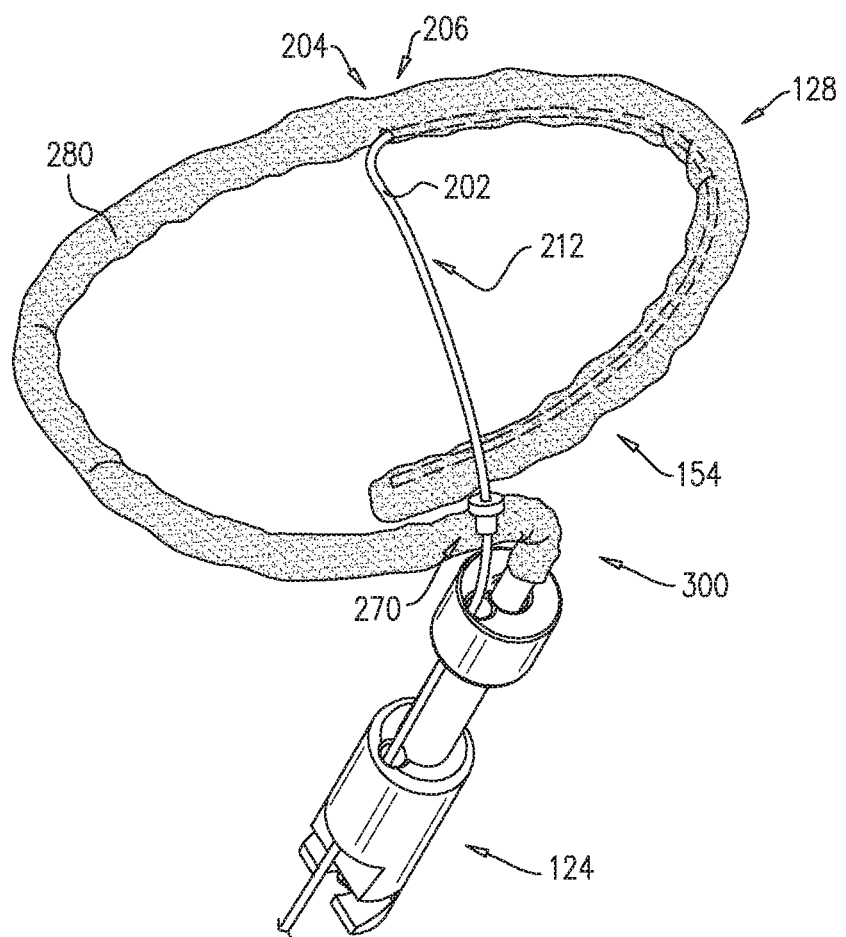

Reference is made to FIGS. 9E and 9F, which are schematic illustrations of alternative ways to fix flexible elongate tension member 202 to site 206 of open loop 154, in accordance with respective applications of the present invention. These techniques may be used for tissue anchor 200 or tissue anchor 300. In the configuration shown in FIG. 9E, distal portion 204 of flexible elongate tension member 202 is fixed to site 206 on open loop 154 by crimping a crimping element 288 around wire 150. In this configuration, a distal portion of flexible elongate tension member 202 beyond site 206 is fixed (e.g., by welding or soldering) to open loop 154, such as near radially-inner end 264 of open loop 154. The portion of flexible elongate tension member 202 between site 206 and radially-inner end 264 may be attached to wire 150, or may be held near wire 150, such as by a sleeve, as described with reference to FIG. 9F. It is noted that site 206 is the site on open loop 154 at which flexible elongate tension member 202 makes functional contact with the loop for applying tension across the loop, rather than other sites along wire 150 to which flexible elongate tension member 202 may also be attached.

The configuration shown in FIG. 9F may be used in combination with the configuration shown in FIG. 9E, or separately. In the configuration shown in FIG. 9F, open loop 154 is covered with a sleeve 280, which may comprise a woven material, comprising, for example, polyester. A distal portion of flexible elongate tension member 202 beyond site 206 is fixed (e.g., by welding or soldering) to open loop 154, such as near radially-inner end 264 of open loop 154 (this area of open loop 154 may facilitate attachment because this area is straighter than other portions of the open loop). Flexible elongate tension member 202 penetrates and exits sleeve 280 at site 206, such as by passing between the fibers of sleeve 280, or through an opening made in sleeve 280, which opening is optionally reinforced. Distal portion 204 of flexible elongate tension member 202 is fixed to site 206 on open loop 154 indirectly by being restrained by sleeve 280. Sleeve 280 may in addition improve tissue growth on the anchor. Optionally, a more proximal portion of flexible elongate tension member 202, after crossing open loop 154, re-enters sleeve 280 through a lateral wall of the sleeve, and exits the proximal end of the sleeve.

Figure 9G:
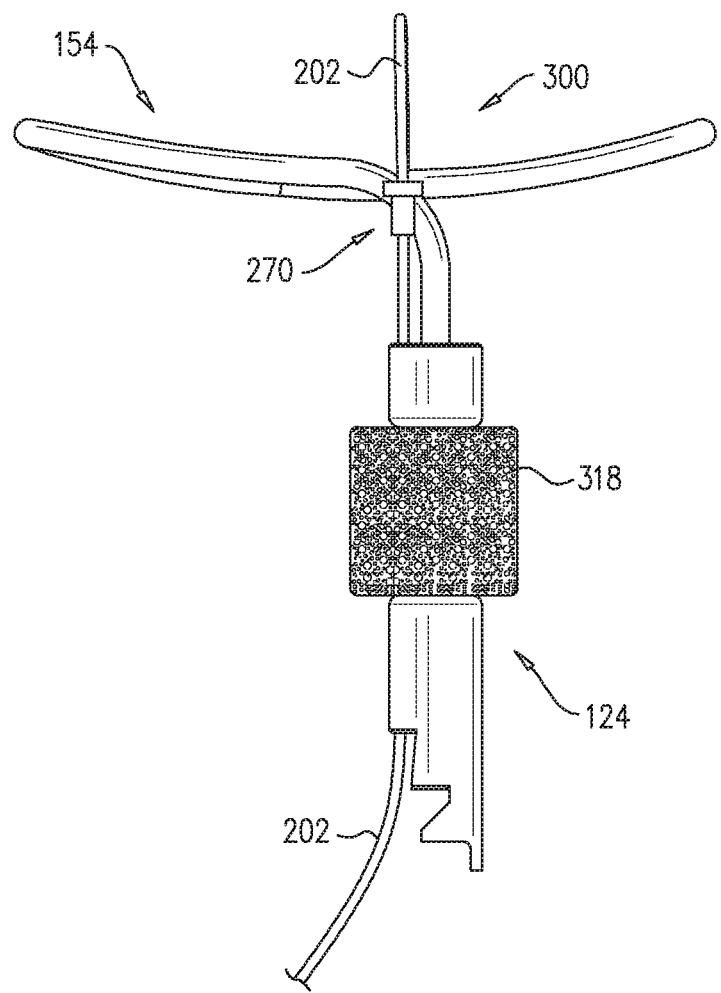
FIG. 9G is a schematic illustration of the anchor of FIGS. 9A-D comprising a sealing element, in accordance with an application of the present invention.

Reference is made to FIG. 9G, which is a schematic illustration of anchor 300 comprising a sealing element 318, in accordance with an application of the present invention. Sealing element 318 is similar in some respects to sealing element 190, described hereinabove with reference to FIGS. 1A-D and 4A-B. Sealing element 318 is configured to form a blood-tight seal between a portion of head 124 inside the heart chamber and wall 194 of the heart. For some applications, sealing element 318 comprises a compressible sponge. For some applications, an outer diameter of sealing element 318, when expanded, equals at least 1.5 times, e.g., at least 2 times, an inner diameter of shaft 34 of deployment tool 30, described hereinabove with reference to FIG. 1A. For some applications, sealing element 318 is disposed on the narrower portion of head 124 between two collars, which can be seen in FIGS. 9A-F.

Figure 9H:
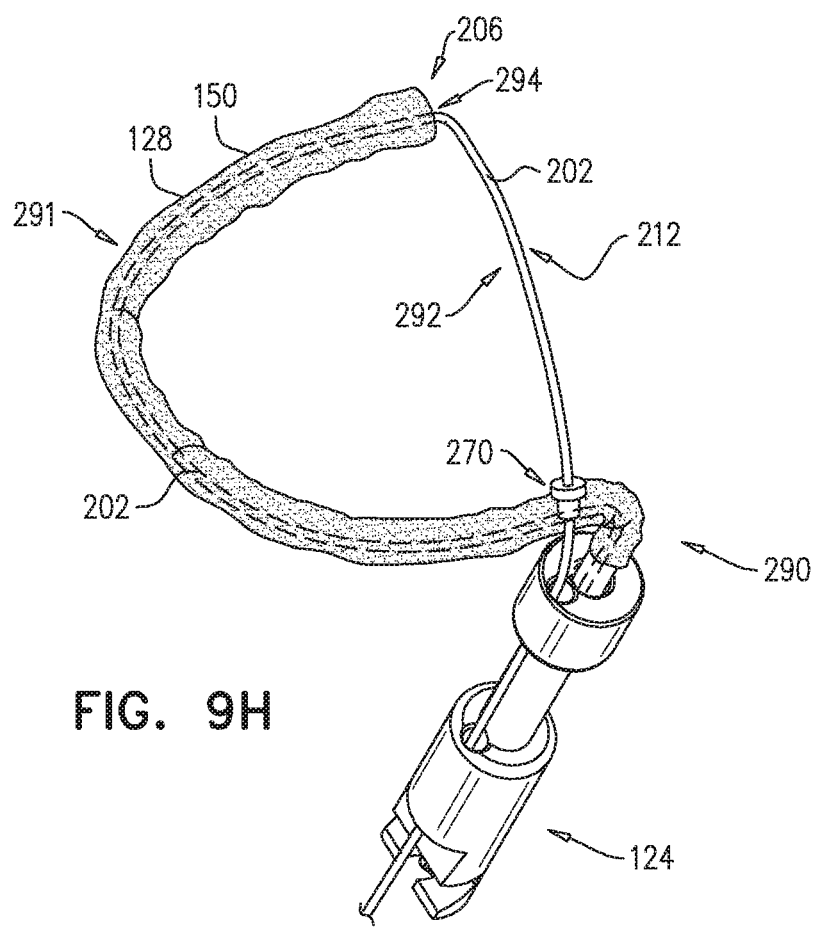
FIG. 9H is a schematic illustration of another tissue anchor, in accordance with an application of the present invention.

Reference is now made to FIG. 9H, which is a schematic illustration of a tissue anchor 290, in accordance with an application of the present invention. Except as described below, anchor 290 is generally similar to anchor 300, described hereinabove with reference to FIGS. 9A-G. Wire 150 of anchor 290 is not shaped as open loop 154. Instead, wire 150 is shaped as an open shape 291, such as a portion of a circle or a portion of an ellipse. Typically, if tissue-coupling element 128 were to be projected onto plane 136 that is perpendicular to central longitudinal axis 134 of shaft 122, open shape 291 would surround at least 170 degrees, no more than 355 degrees, and/or between 170 and 355 degrees of a point 292 in plane 136, such as at least 180 degrees (e.g., at least 190 degrees), no more than 345 degrees, and/or between 180 degrees (e.g., 190 degrees) and 345 degrees. For some applications, such as in which open shape 291 surrounds between 170 and 190 degrees of point 292, site 206 is at a distal end 294 of wire 150. For some of these applications, wire 150 is shaped so as to define a channel, through which a portion of flexible elongate tension member 202 passes and exits wire 150 at distal end 294 of wire 150.

Figure 9I:
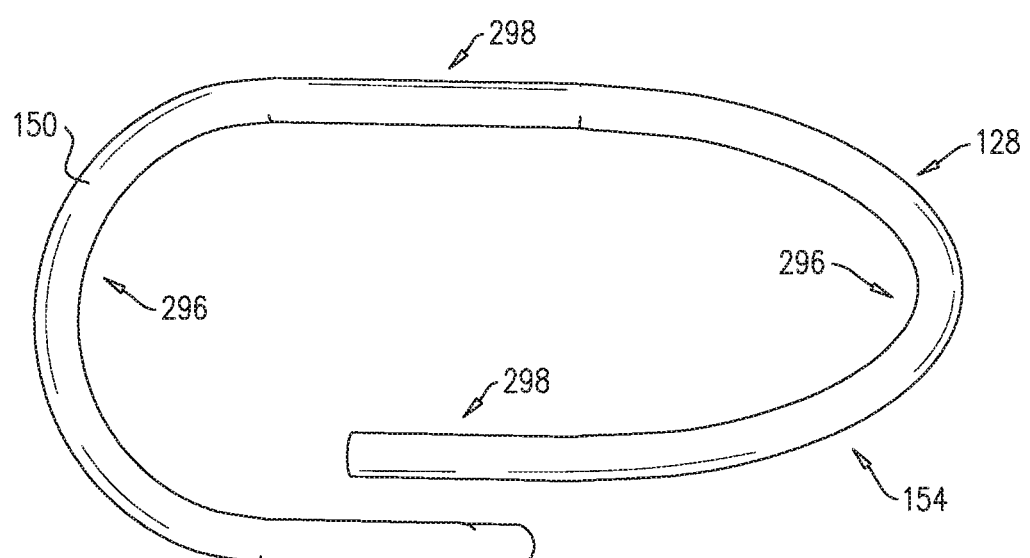
FIG. 9I is a schematic illustration of another configuration of an open loop, in accordance with an application of the present invention.

Reference is now made to FIG. 9I, which is a schematic illustration of another configuration of open loop 154, in accordance with an application of the present invention. This configuration may be used in combination tissue anchors 120, 200, 258, 290, and 300. In this configuration, when the tissue anchor is unconstrained by deployment tool 30, open loop 154 is shaped so as to define one or more curved portions 296 (e.g., two or more curved portions 296) and one or more straight portions 298 (e.g., two or more straight portions 298). Straight portions 298 generally maximize the surface contact with the external surface of the heart and thus provide good anchoring. For some applications, open loop 154 is shaped as a common, conventional paper clip (an oblong shape with straight sides, with approximately 1.5 turns).

Reference is now made to FIGS. 10A-B, which are schematic illustrations of a tissue anchor 220 in several stages of deployment from deployment tool 30, in accordance with an application of the present invention. Tissue anchor 220 is one implementation of tissue anchor 20, described above. Tissue anchor 120 typically comprises (a) a shaft 222, and (b) a tissue-coupling element 228, which extends from a distal end 230 of shaft 222, and which comprises three or more tines 232, such as four or more tines 232.

FIG. 10A shows tissue-coupling element 228 fully constrained by deployment tool 30. When tissue anchor 220 is fully constrained by deployment tool 30, tissue-coupling element 228 typically has an outer diameter of at least 1 mm, no more than 4 mm, and/or between 1 and 4 mm.

FIG. 10B shows tissue-coupling element 228 released from deployment tool 30, while a portion of tissue anchor 220 is still constrained by deployment tool 30. Deployment tool 30 may have any of the features described hereinabove with reference to FIGS. 1A-D.

When tissue anchor 220 is unconstrained by deployment tool 30:
shaft 222 has a central longitudinal axis 234,
tines 232 extend radially outward from central longitudinal axis 234 in respective directions that are fixed with respect to one another, and
tissue-coupling element 228 is shaped such that if tissue-coupling element 228 were to be projected onto a plane 236 that is perpendicular to central longitudinal axis 234, at least 80% (e.g., at least 90%, such at least 95%) of an area 238 of a projection 239 of tissue-coupling element 228 on plane 236 would fall within an angle c (epsilon) of 210 degrees in plane 236 having a vertex 240 at central longitudinal axis 234.

For some applications, at least one pair of circumferentially-adjacent ones of tines 232 (e.g., all pairs) is offset by an angle of at least 30 degrees, no more than 60 degrees, and/or between 30 and 60 degrees. For some applications, the respective angles between circumferentially-adjacent ones of tines 232 vary by less than 10%, e.g., are equal to one another.

For some applications, tissue anchor 220 further comprises a head connected to a proximal portion of shaft 222 (configuration not shown); for example, the head may be head 124, described hereinabove with reference to FIGS. 1A-D. For some applications, the one or more tethers 132, described hereinabove with reference to FIGS. 1A-D, are provided; one of the one or more tethers 132 is configured to be coupled to tissue anchor 220, such as to the head of tissue anchor 220; for example, one of the one or more tethers 132 may be fixed to the head.

For some applications, tissue anchor 220 is a first tissue anchor of a tissue anchor system, which further comprises (a) a second tissue anchor, which is separate and distinct from the first tissue anchor, and (b) the one or more tethers 132, which are configured to couple (a) the first tissue anchor to (b) the second tissue anchor. The one or more tethers and second tissue anchor may implement any of the techniques described hereinabove with reference to FIGS. 4A-B, mutatis mutandis.

For some applications, central longitudinal axis 234 is straight when tissue-coupling element 228 is unconstrained by deployment tool 30, such as shown in FIG. 10B. For some applications, shaft 222 is flexible. For some applications, distal ends 252 of tines 232 do not define respective sharp distal tips; for example, the distal ends may be blunt. Tissue-coupling element 228 is non-helical when tissue anchor 220 is unconstrained by deployment tool 30.

For some applications, a proximally-facing surface defined by tissue-coupling element 228 is concave when tissue anchor 220 is unconstrained by deployment tool 30.

For some applications (labeled in FIG. 10B), when tissue anchor 220 is unconstrained by deployment tool 30:
greatest longitudinal dimension D2 of tissue-coupling element 228, measured parallel to central longitudinal axis 234, is between 0 and 6 mm (such as between 1 and 5 mm), and
greatest lateral dimension D3 of tissue-coupling element 228, measured perpendicular to central longitudinal axis 234, is between 4 and 25 mm (such as between 5 and 24 mm).

For some applications, angle c (epsilon) is a first angle c (epsilon). At least 80% (e.g., at least 90%, such as at least 95%) of area 238 of projection 239 of tissue-coupling element 228 on plane 236 would fall within a second angle (zeta) of 180 degrees in plane 236 having vertex 240 at central longitudinal axis 234.

Reference is again made to FIGS. 10A-B. For some applications, tissue anchor 220 is implanted using techniques described hereinbelow with reference to FIGS. 13A-D, 15A-C, and/or 16, mutatis mutandis.

Reference is now made to FIGS. 11A-C, which are schematic illustrations of several views of a tissue anchor 320, in accordance with an application of the present invention. Tissue anchor 320 is one implementation of tissue anchor 20, described above. Except as described below, tissue anchor 320 is similar to tissue anchor 220, described hereinabove with reference to FIGS. 10A-B, and may incorporate any of the features thereof. A tissue-coupling element 328 of tissue anchor 320 further comprises one or more membranes 342 that are fixed to and extend between circumferentially-adjacent ones of tines 232. The membranes and tines together might be considered to define a structure similar in some respect to a bat wing, or a partial umbrella. The membranes may help evenly distribute the force on the external surface of the heart applied by the tissue-coupling element, and/or may provide a seal to the heart wall. For some applications, membranes 342 comprise a polymer or polymeric (synthetic or natural) mesh to promote tissue integration.

Reference is still made to FIGS. 11A-C. For some applications, tissue anchor 320 is implanted using techniques described hereinbelow with reference to FIGS. 13A-D, 15A-C, and/or 16, mutatis mutandis.

Figure 12A:
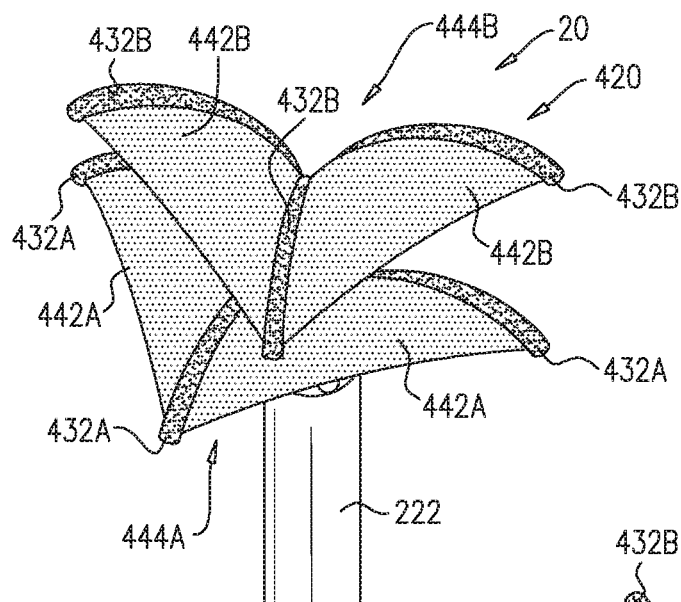
FIGS. 12A-C are schematic illustrations of still another tissue anchor, in accordance with an application of the present invention.
Figure 12B:
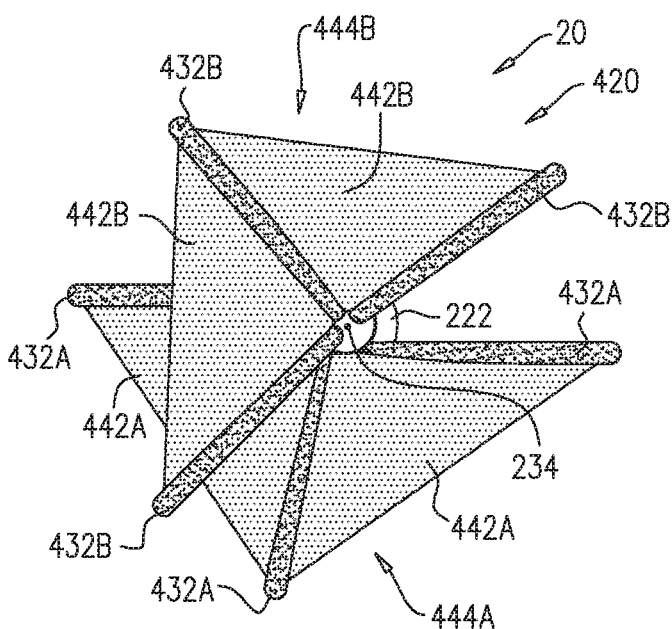
Figure 12C:
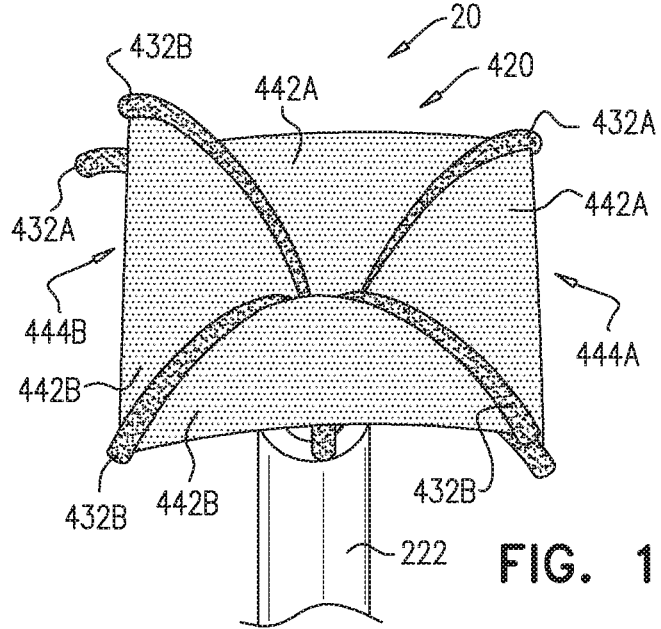

Reference is now made to FIGS. 12A-C, which are schematic illustrations of a tissue anchor 420, in accordance with an application of the present invention. Tissue anchor 420 is one implementation of tissue anchor 20, described above. Except as described below, tissue anchor 420 is similar to tissue anchor 320, described hereinabove with reference to FIGS. 11A-C, and may incorporate any of the features thereof. A tissue-coupling element 428 of tissue anchor 420 comprises:
three or more first tines 432A, such as four or more first tines 432A, which are typically rotationally fixed with respect to one another;
three or more second tines 432B, such as four or more second tines 432B, which are typically rotationally fixed with respect to one another;
one or more first membranes 442A that are fixed to and extend between circumferentially-adjacent ones of first tines 432A, and are not fixed to any of second tines 432B; and
one or more second membranes 442B that are fixed to and extend between circumferentially-adjacent ones of second tines 432B, and are not fixed to any of first tines 432A.

The first membranes and first tines together might be considered to define a structure similar in some respect to a first bat wing 444A, or a first partial umbrella 444A, and the second membranes and second tines together might be considered to define a structure similar in some respect to a second bat wing 444B, or a second partial umbrella 444B.

For some applications, tissue anchor 420 is configured such that second tines 432B are rotatable with respect to first tines 432A. As a result, the first bat wing (or partial umbrella) 444A is rotatable with respect to the second bat wing (or partial umbrella) 444B. Such rotation allows adjustment of the total collective coverage of the first and second membranes (and bat wings), in order to adjust the total angular coverage of tissue-coupling element 428. First tines 432A are disposed at different axial heights from second tines 432B, in order to allow one of the bat wings (or partial umbrellas) to rotate over the other.

For some applications, first tines 432A are rotationally fixed with respect to shaft 222 (although the shaft itself may be rotatable). For some applications, tissue anchor 420 comprises a second shaft, and second tines 432B are rotationally fixed with respect the second shaft. The second shaft is rotatable with respect to shaft 222. Typically, the second shaft is disposed within a lumen of shaft 222, or shaft 222 is disposed within a lumen of the second shaft.

For some applications, when tissue anchor 420 is unconstrained by deployment tool 30, tissue-coupling element 428 is shaped such that:
(a) first membranes 442A extend circumferentially around central longitudinal axis 234 between 90 and 180 degrees, and (b) second membranes 442B extend circumferentially around central longitudinal axis 234 between 90 and 180 degrees; and/or
(a) first membranes 442A extend circumferentially around central longitudinal axis 234 a first number of degrees, (b) second membranes 442B extend circumferentially around central longitudinal axis 234 a second number of degrees, and (c) a sum of the first and second numbers of degrees is between 100 and 350 degrees, such as between 150 and 270 degrees.

For some applications, a proximally-facing surface defined by tissue-coupling element 428 is concave when tissue anchor 420 is unconstrained by deployment tool 30.

For some applications, tissue anchor 420 does not comprise membranes 442A or 442B (configuration not shown). Thus, in these applications, tissue-coupling element 428 of tissue anchor 420 comprises:
three or more first tines 432A, such as four or more first tines 432A, which are rotationally fixed with respect to one another; and
three or more second tines 432B, such as four or more second tines 432B, which are rotationally fixed with respect to one another.

In these applications, tissue anchor 420 is configured such that second tines 432B are rotatable with respect to first tines 432A. Such rotation allows adjustment of the total collective coverage of first tines 432A and second tines 432B, in order to adjust the total angular coverage of tissue-coupling element 428. First tines 432A are disposed at different axial heights from second tines 432B, in order to allow one set of the tines to rotate over the other.

For some of these applications, first tines 432A are rotationally fixed with respect to shaft 222 (although the shaft itself may be rotatable). For some applications, tissue anchor 420 comprises a second shaft, and second tines 432B are rotationally fixed with respect the second shaft. The second shaft is rotatable with respect to shaft 222. Typically, the second shaft is disposed within a lumen of shaft 222, or shaft 222 is disposed within a lumen of the second shaft.

For some of these applications, when tissue anchor 420 is unconstrained by deployment tool 30, tissue-coupling element 428 is shaped such that:
(a) first tines 432A extend circumferentially around central longitudinal axis 234 between 90 and 180 degrees, and (b) second tines 432B extend circumferentially around central longitudinal axis 234 between 90 and 180 degrees; and/or
(a) first tines 432A extend circumferentially around central longitudinal axis 234 a first number of degrees, (b) second tines 432B extend circumferentially around central longitudinal axis 234 a second number of degrees, and (c) a sum of the first and second numbers of degrees is between 100 and 350 degrees, such as between 150 and 270 degrees.

Reference is made to FIGS. 12A-C. For some applications, tissue anchor 420 is implanted using techniques described hereinbelow with reference to FIGS. 13A-D, 15A-C, and/or 16, mutatis mutandis to provide for the rotation of second tines 432B with respect to first tines 432A. Typically, first tines 432A are rotated with respect to the external surface of the heart to avoid overlying coronary blood vessels, such as a right coronary artery (RCA) 590, and second tines 432B are rotated with respect to first tines 432A to adjust the total angular coverage of tissue-coupling element 428 to avoid overlying coronary blood vessels.

Reference is now made to FIGS. 13A-D, which are schematic illustrations of a method for deploying tissue anchor system 180, described hereinabove with reference to FIGS. 4A-B, for repairing a tricuspid valve 504, in accordance with an application of the present invention. In the particular method shown in these figures, first and second tissue anchors 182A and 182B of tissue anchor system 180 comprise first tissue anchor 120 and stent 186, described hereinabove with reference to FIG. 4B. The method may also be used to deploy other tissue anchors described herein, mutatis mutandis. Tissue anchor system 180 further comprises deployment tool 30, for deploying first tissue anchor 182A, and, typically, a second anchor delivery tool for deploying second tissue anchor 182B.

Figure 13A:
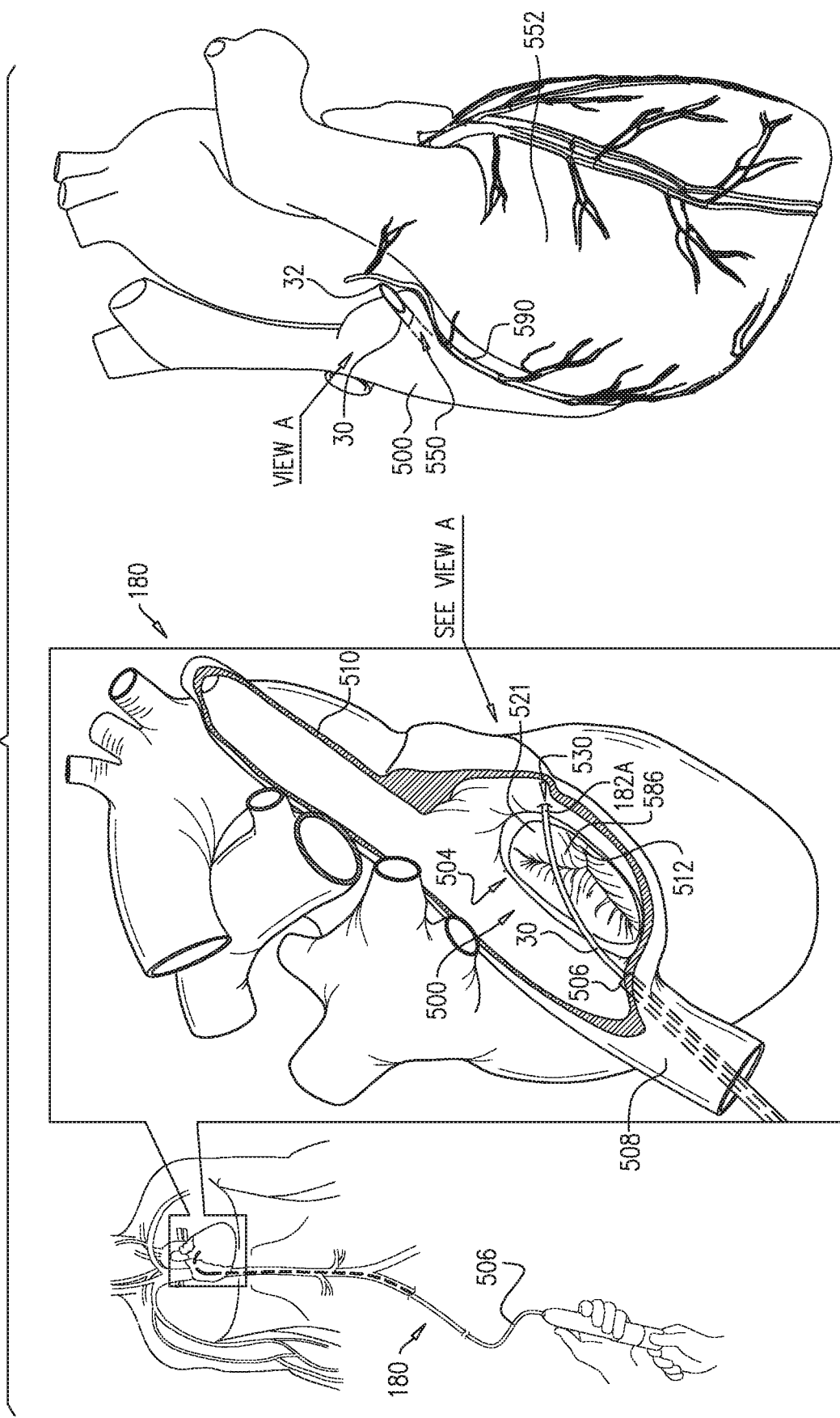

As shown in FIG. 13A, first anchor deployment tool 30 is advanced, during a transcatheter procedure (typically endovascularly, such as percutaneously), via a catheter 506, with the aid of a guidewire, through vasculature of the subject, and into a cardiac chamber, such as a right atrium 500 toward a first implantation site 530 at tricuspid valve 504 through an inferior vena cava 508 from a suitable point of entry. Alternatively, the delivery tool may be advanced through a superior vena cava 510. First tissue anchor 182A is constrained within first anchor deployment tool 30, such as described hereinabove with reference to FIG. 1A. The procedure is typically performed with the aid of imaging, such as fluoroscopy, transesophageal, transthoracic echocardiography, ICE, and/or echocardiography.

Also as shown in FIG. 13A, first anchor deployment tool 30 is advanced through the wall of the heart by advancing sharp distal piercing tip 32 of the tool through first implantation site 530. Successful passage through the wall is typically confirmed using imaging. First implantation site 530 is shown as within 1 cm of the site on the annulus that circumferentially corresponds to a circumferential middle 521 of an anterior leaflet 586; alternative first implantation sites 530 are set forth hereinbelow in Table 1. For some applications, first implantation site 530 is within 10 mm, such as within 5 mm, of RCA 590.

Figure 13B:
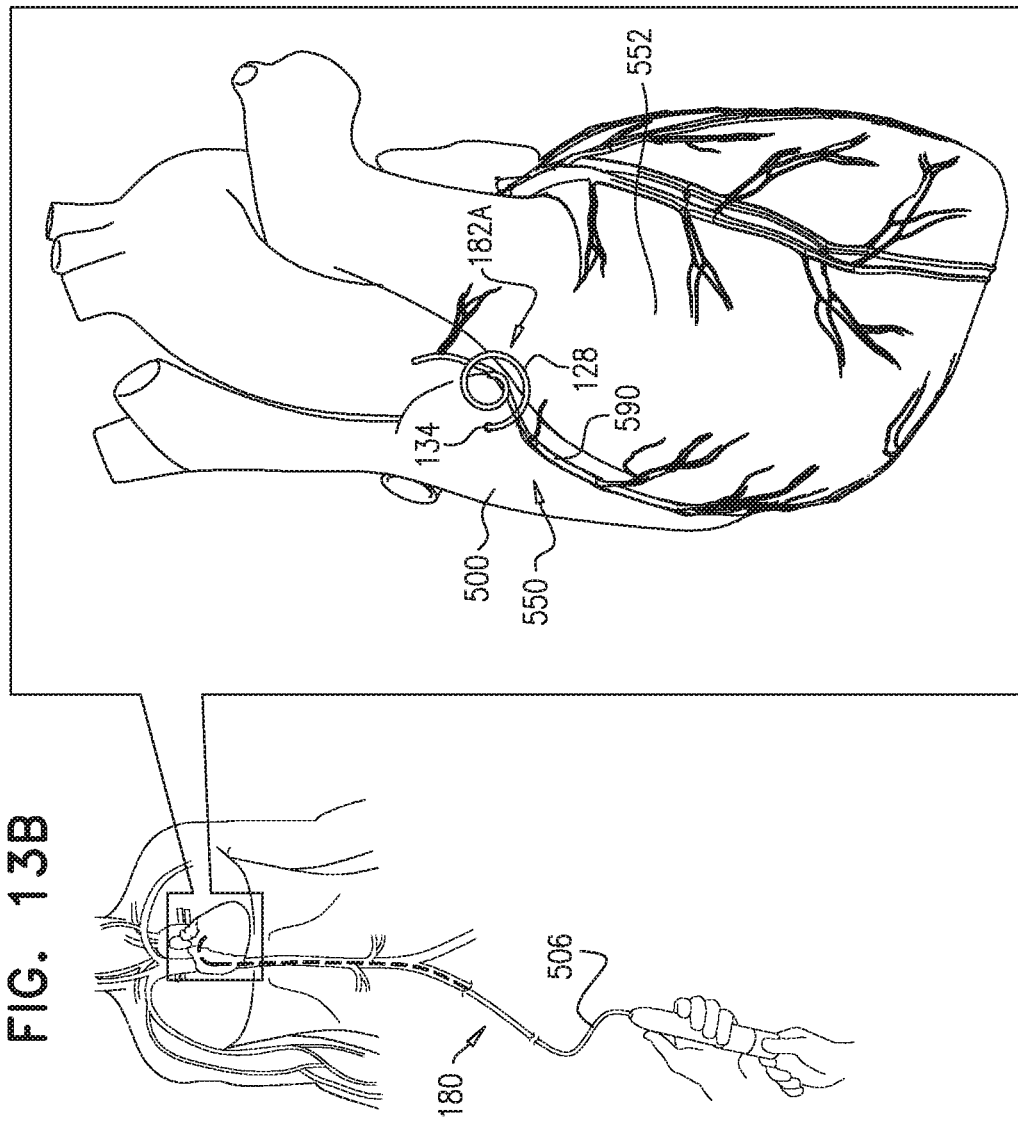

As shown in FIG. 13B, first tissue anchor 182A is partially released from first anchor deployment tool 30 such that tissue-coupling element 128 is unconstrained by first anchor deployment tool 30. The surgeon ascertains, typically using imaging, whether tissue-coupling element 128 overlies a coronary blood vessel, such as RCA 590. In the procedure shown in FIG. 13B, tissue-coupling element 128 does overlie a coronary blood vessel (RCA 590).

For some applications, such as shown in FIGS. 13A-D, first anchor deployment tool 30, and first tissue anchor 182A, exit the heart at an external exit site 550 on right atrium 500. Typically, in these applications, first tissue anchor 182A passes through an atrial portion of the annulus, or an edge of the annulus and the origin of the trabeculae carneae. For other applications, such as described hereinbelow with reference to FIG. 16, first anchor deployment tool 30, and first tissue anchor 182A, exit the heart at external exit site 550 on a right ventricle 552. Typically, in these applications, first tissue anchor 182A passes under RCA 590 in the annulus and exits on the ventricular wall.

If tissue-coupling element 128 overlies a coronary blood vessel (e.g., RCA 590), the surgeon rotates first tissue anchor 182A (clockwise and/or counterclockwise, about central longitudinal axis 134) until tissue-coupling element 128 no longer overlies the coronary blood vessel, as shown in FIG. 13C. The rotation is typically performed by rotating shaft 122. The surgeon brings tissue-coupling element 128 into contact with an external surface 534 of the heart, by proximally retracting first tissue anchor 182A.

After first tissue anchor 182A has been implanted at first implantation site 530, deployment tool 30 is removed from the subject's body, typically leaving catheter 506 in situ.

Figure 13D:
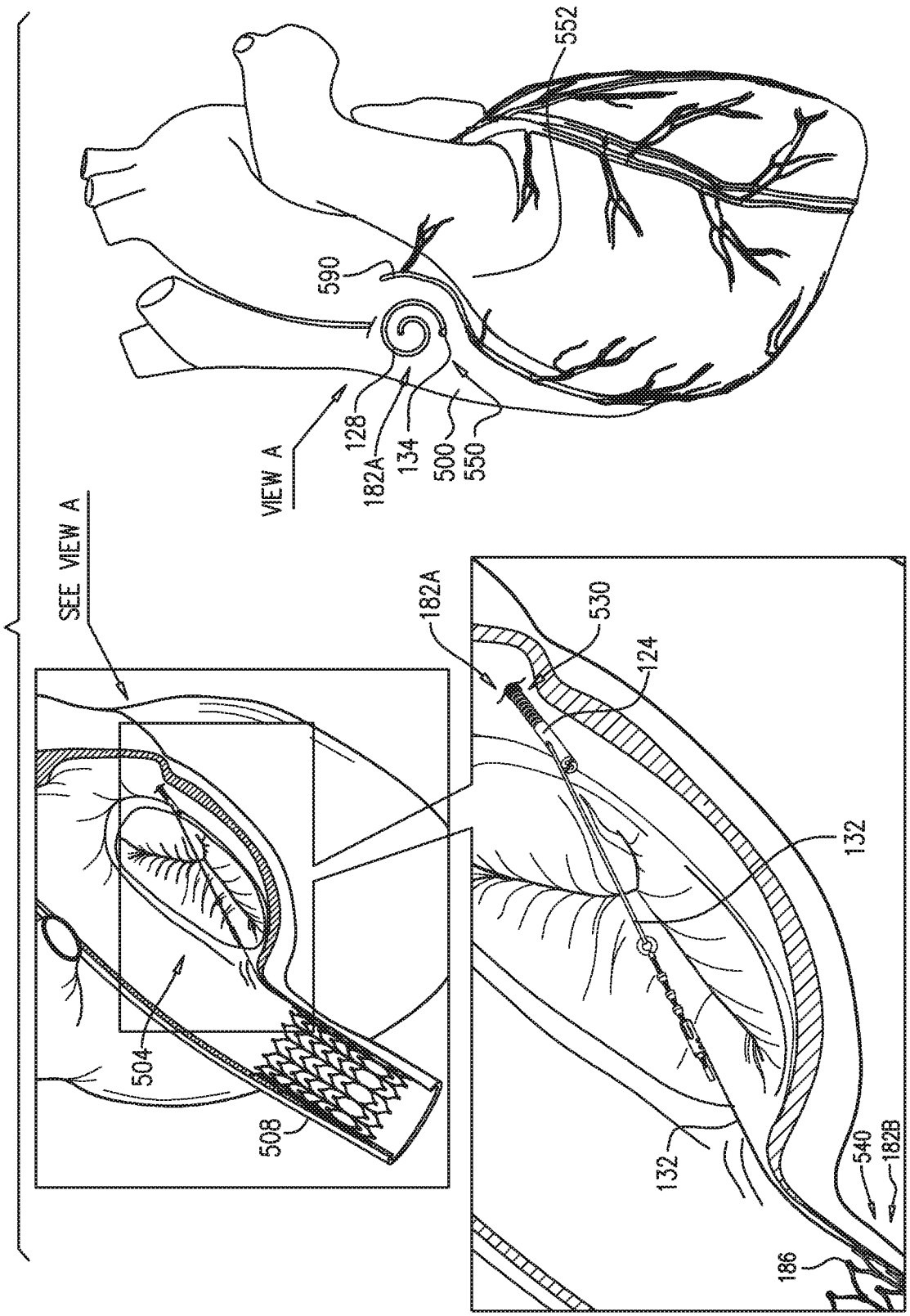

As shown in FIG. 13D, second tissue anchor 182B is implanted in the subject at a second implantation site 540. For example, as shown, second tissue anchor 182B may comprise stent 186, and second implantation site 540 may be inferior vena cava 508; an alternative second implantation site 540 is set forth hereinbelow in Table 1. Tension is applied to the one or more tethers 132 that couple the first tissue anchor 182A (e.g., the head thereof) to second tissue anchor 182B. Application of such tension facilitates repair of an atrioventricular valve of the subject, such as tricuspid valve 504.

For some applications, second tissue anchor 182B is implanted in the subject, and first tissue anchor 182A is coupled to second tissue anchor 182B by the one or more tethers 132 using the techniques described for connecting first and second tissue-engaging elements 60a and 60b in US Patent Application Publication 2014/0114390 with reference to FIGS. 34A-E thereof; the '390 publication is incorporated herein by reference. For some applications, one of the one or more tethers 132 is fixed to one of (a) first tissue anchor 182A and (b) second tissue anchor 182B. For some applications, first and second tissue anchors 182A and 182B are implanted using techniques described in US Patent Application Publication 2012/0035712 with reference to FIGS. 7A-D and/or FIGS. 11A-B thereof; the '715 publication is incorporated herein by reference.

Reference is now made to FIGS. 14A-D, which are schematic illustrations of a method for deploying tissue anchor system 248, described hereinabove with reference to FIGS. 6A-B, for repairing tricuspid valve 504, in accordance with an application of the present invention. In the particular method shown in these figures, first and second tissue anchors 182A and 182B of tissue anchor system 248 comprise first tissue anchor 300, described hereinabove with reference to FIGS. 9A-G, and stent 186, described hereinabove with reference to FIG. 6B. The method may also be used to deploy other tissue anchors described herein, mutatis mutandis. Tissue anchor system 248 further comprises deployment tool 30, for deploying first tissue anchor 182A, and, typically, a second anchor delivery tool for deploying second tissue anchor 182B.

Figure 14A:
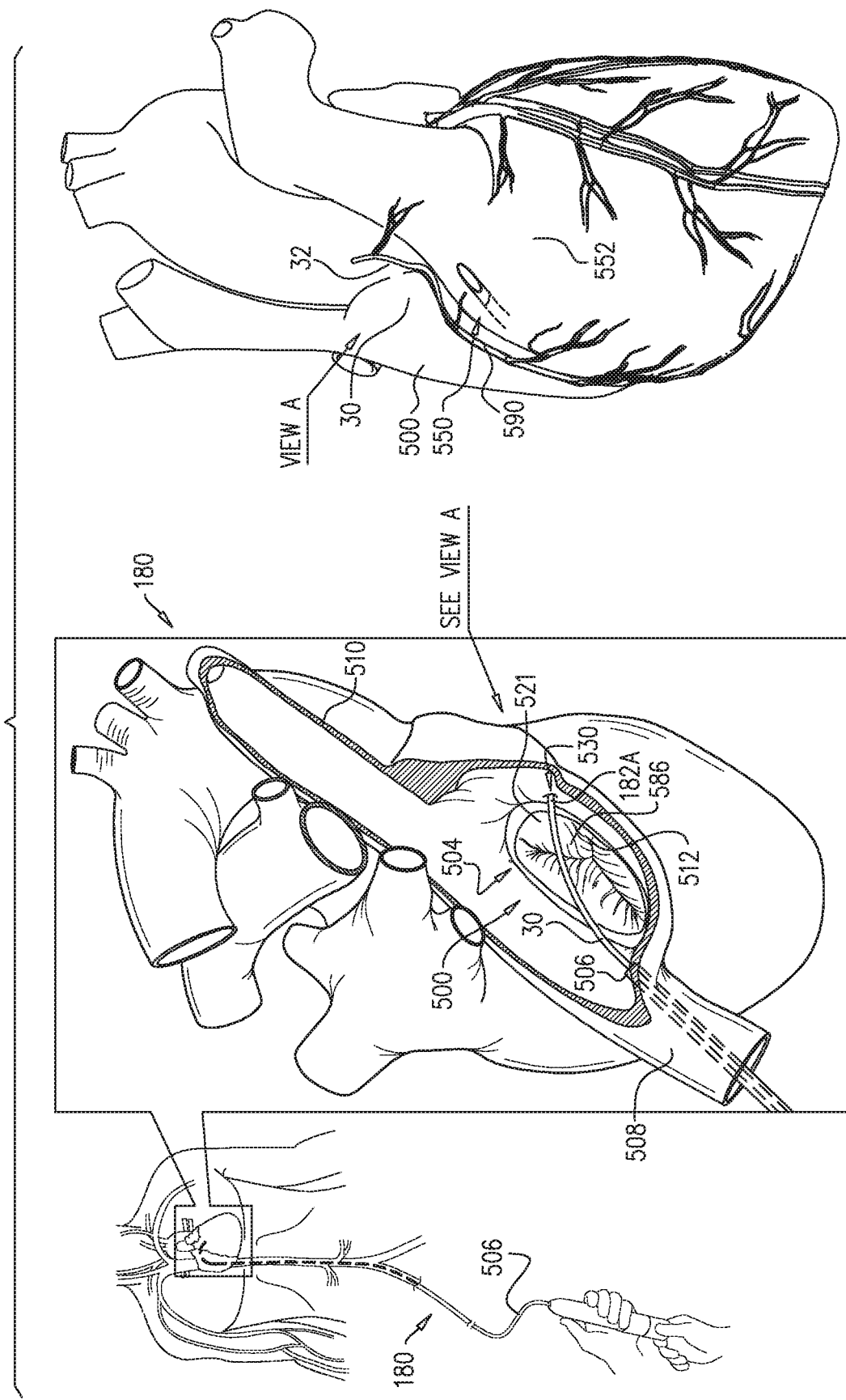
FIGS. 14A-D are schematic illustrations of a method for deploying the tissue anchor system of FIGS. 6A-B for repairing a tricuspid valve, in accordance with an application of the present invention.

As shown in FIG. 14A, first anchor deployment tool 30 is advanced, during a transcatheter procedure (typically endovascularly, such as percutaneously), such as described hereinabove with reference to FIG. 13A. Also as shown in FIG. 14A, first anchor deployment tool 30 is advanced through the wall of the heart by advancing sharp distal piercing tip 32 of the tool through first implantation site 530. Successful passage through the wall is typically confirmed using imaging. First implantation site 530 is shown as within 1 cm of the site on the annulus that circumferentially corresponds to circumferential middle 521 of anterior leaflet 586; alternative first implantation sites 530 are set forth hereinbelow in Table 1. For some applications, first implantation site 530 is within 10 mm, such as within 5 mm, of RCA 590.

Figure 14B:
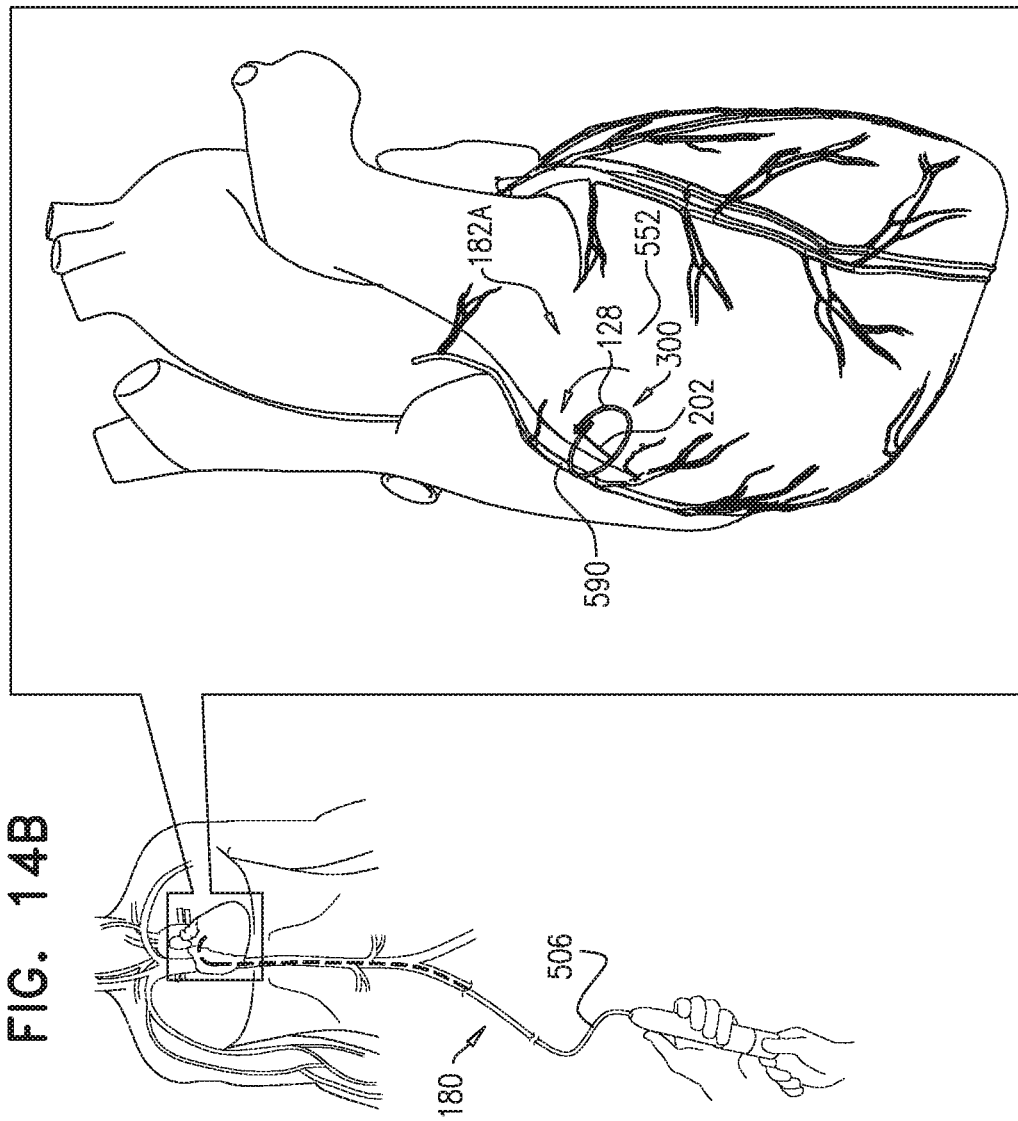

As shown in FIG. 14B, first tissue anchor 182A is partially released from first anchor deployment tool 30 such that tissue-coupling element 128 is unconstrained by first anchor deployment tool 30. The surgeon ascertains, typically using imaging, whether tissue-coupling element 128 overlies a coronary blood vessel, such as RCA 590. In the procedure shown in FIG. 14B, tissue-coupling element 128 does overlie a coronary blood vessel (RCA 590).

For some applications, such as shown in FIGS. 14A-D, first anchor deployment tool 30, and first tissue anchor 182A, exit the heart at external exit site 550 on right atrium 500. Typically, in these applications, first tissue anchor 182A passes through an atrial portion of the annulus, or an edge of the annulus and the origin of the trabeculae carneae. For other applications, such as described hereinbelow with reference to FIG. 16, first anchor deployment tool 30, and first tissue anchor 182A, exit the heart at external exit site 550 on right ventricle 552. Typically, in these applications, first tissue anchor 182A passes under RCA 590 in the annulus and exits on the ventricular wall.

Figure 14C:
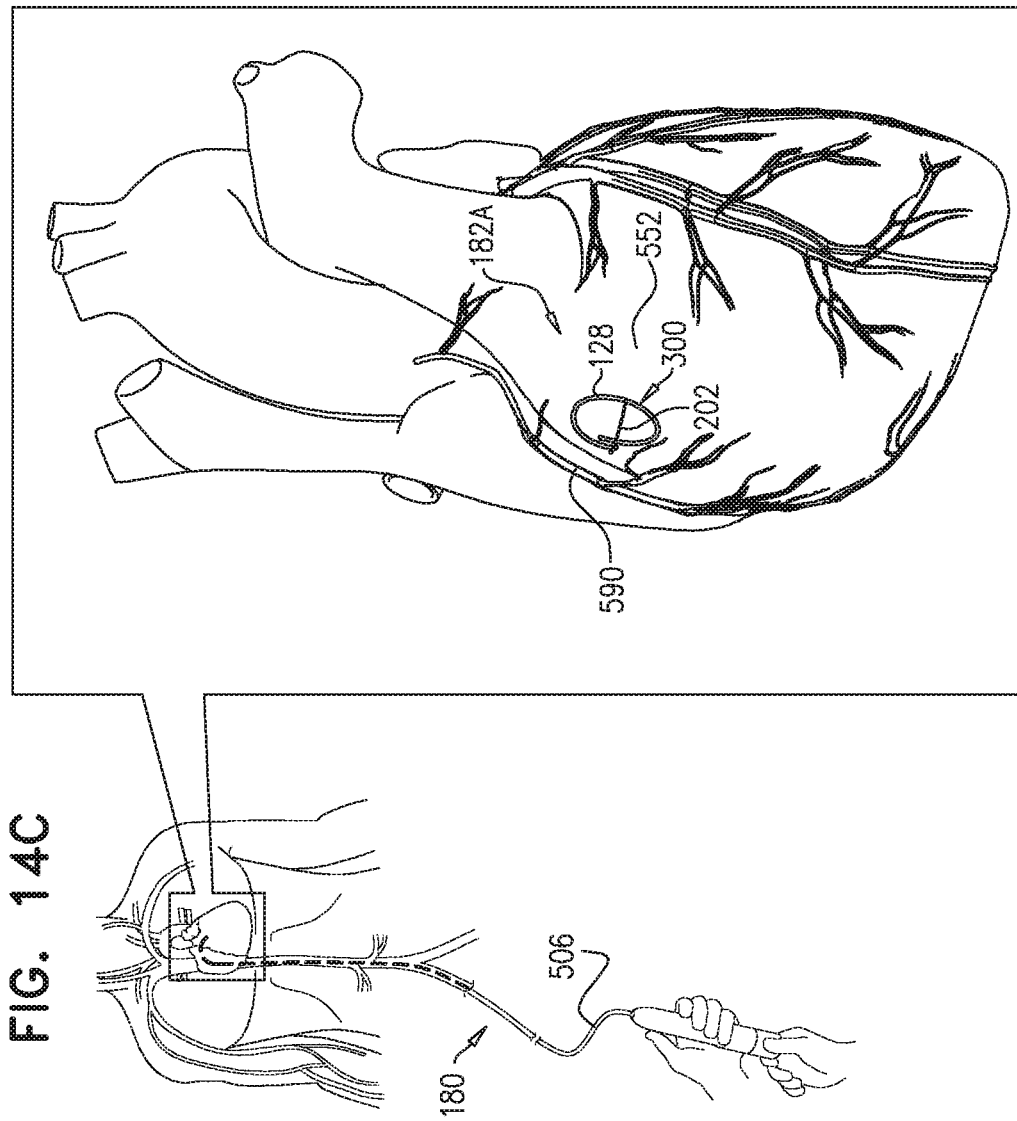

If tissue-coupling element 128 overlies a coronary blood vessel (e.g., RCA 590), the surgeon rotates first tissue anchor 182A (clockwise and/or counterclockwise, about central longitudinal axis 134) until tissue-coupling element 128 no longer overlies the coronary blood vessel, as shown in FIG. 14C. The rotation is typically performed by rotating shaft 122. The surgeon brings tissue-coupling element 128 into contact with an external surface 534 of the heart, by proximally retracting first tissue anchor 182A.

Providing the tissue anchor (e.g., tissue anchor 300) with an elliptical shape (or paper clip shape) reduces the risk of contact with a sensitive anatomic structure, such as a blood vessel, e.g., the RCA.

After first tissue anchor 182A has been implanted at first implantation site 530, driver 201 is decoupled from the anchor head and deployment tool 30 is removed from the subject's body, typically leaving catheter 506 in situ.

Figure 14D:
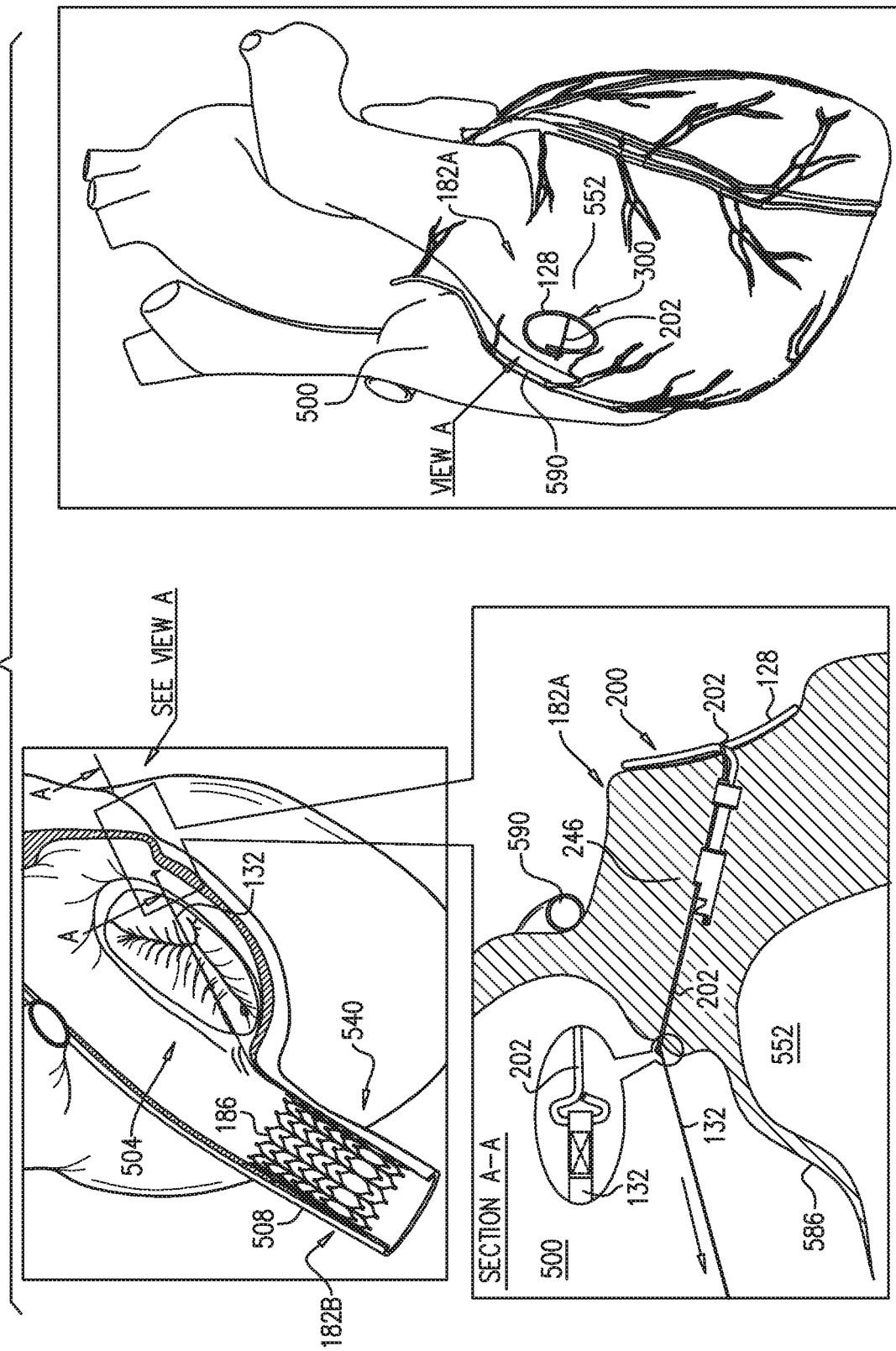

As shown in FIG. 14D, second tissue anchor 182B is implanted in the subject at second implantation site 540. For example, as shown, second tissue anchor 182B may comprise stent 186, and second implantation site 540 may be inferior vena cava 508; an alternative second implantation site 540 is set forth hereinbelow in Table 1. Tension is applied to the one or more tethers 132 that couple the first tissue anchor 182A (e.g., flexible elongate tension member 202 thereof) to second tissue anchor 182B. Typically, the tension is applied without applying tension to shaft 122. Application of such tension facilitates repair of an atrioventricular valve of the subject, such as tricuspid valve 504.

For some applications, second tissue anchor 182B is implanted in the subject, and first tissue anchor 182A is coupled to second tissue anchor 182B by the one or more tethers 132 using the techniques described for connecting first and second tissue-engaging elements 60a and 60b in US Patent Application Publication 2014/0114390 with reference to FIGS. 34A-E thereof; the '390 publication is incorporated herein by reference. For some applications, one of the one or more tethers 132 is fixed to one of (a) first tissue anchor 182A and (b) second tissue anchor 182B. For some applications, first and second tissue anchors 182A and 182B are implanted using techniques described in US Patent Application Publication 2012/0035712 with reference to FIGS. 7A-D and/or FIGS. 11A-B thereof; the '715 publication is incorporated herein by reference.

The following Table 1 sets forth exemplary combinations of (a) anatomical markers for first implantation site 530, (b) second implantation site 540, and (c) external exit sites 550. These sites are listed by way of example and not limitation; the surgeon typically selects the exact sites based on the subject's individual needs and anatomy. Any appropriate location on the heart wall may be used. First implantation site 530 is located within 1 cm of the site on the annulus that circumferentially corresponds to the anatomical marker (i.e., is at the same angular location or "o'clock" as the respective anatomical marker). The direction of the 1 cm from the site on the annulus may be either circumferentially (i.e., clockwise or counterclockwise) around the annulus, up the wall of the right atrium above the annulus, or a combination of circumferentially around the annulus and up the wall of the atrium.

Typically, the surgeon uses the anatomical markers to find the exact location first implantation site 530, which is within 1 cm of the anatomical markers, as described above. For example, the commissures are easily detectable using imaging, and thus represent good anatomical markers. However, the commissures are not appropriate for implantation (because they are too delicate), so, in this example, the anchors are implanted near the annulus, such as up the wall of the atrium, within 1 cm from the commissure.

TABLE 1

| First implantation site 530 anatomical marker | Second implantation site 540 | External exit site 550 |
|---|---|---|
| Circumferential middle 521 of anterior leaflet 586 | Inferior vena cava 508 | Right atrium 500 (site 550A in FIG. 16) |
| An anteroposterior commissure 512 | Inferior vena cava 508 | Right atrium 500 (site 550B in FIG. 16) |
| Circumferential middle 521 of anterior leaflet 586 | Inferior vena cava 508 | Right ventricle 552 (site 550C in FIG. 16) |
| Anteroposterior commissure 512 | Inferior vena cava 508 | Right ventricle 552 (site 550D in FIG. 16) |
| A circumferential middle of a posterior leaflet | Superior vena cava 510 | Right ventricle 552 (site 550C in FIG. 16) |
| Anteroposterior commissure 512 | Superior vena cava 510 | Right ventricle 552 (site 550D in FIG. 16) |
| Circumferential middle 521 of anterior leaflet 586 | A coronary sinus | Right atrium 500 (site 550A in FIG. 16) |

Figure 15A:
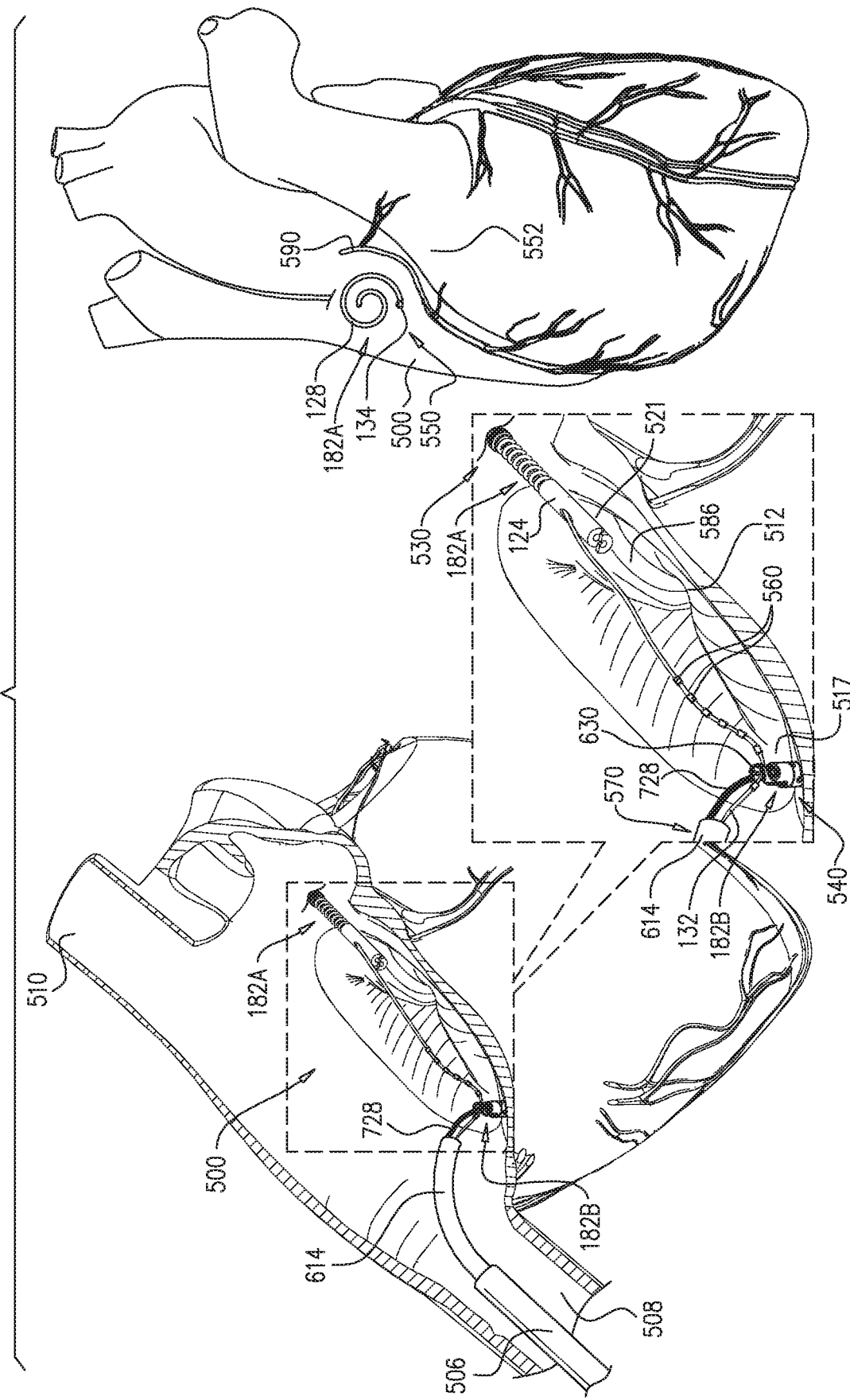
FIGS. 15A-C are schematic illustrations of another method for deploying a tissue anchor system for repairing the tricuspid valve, in accordance with an application of the present invention.
Figure 15B:
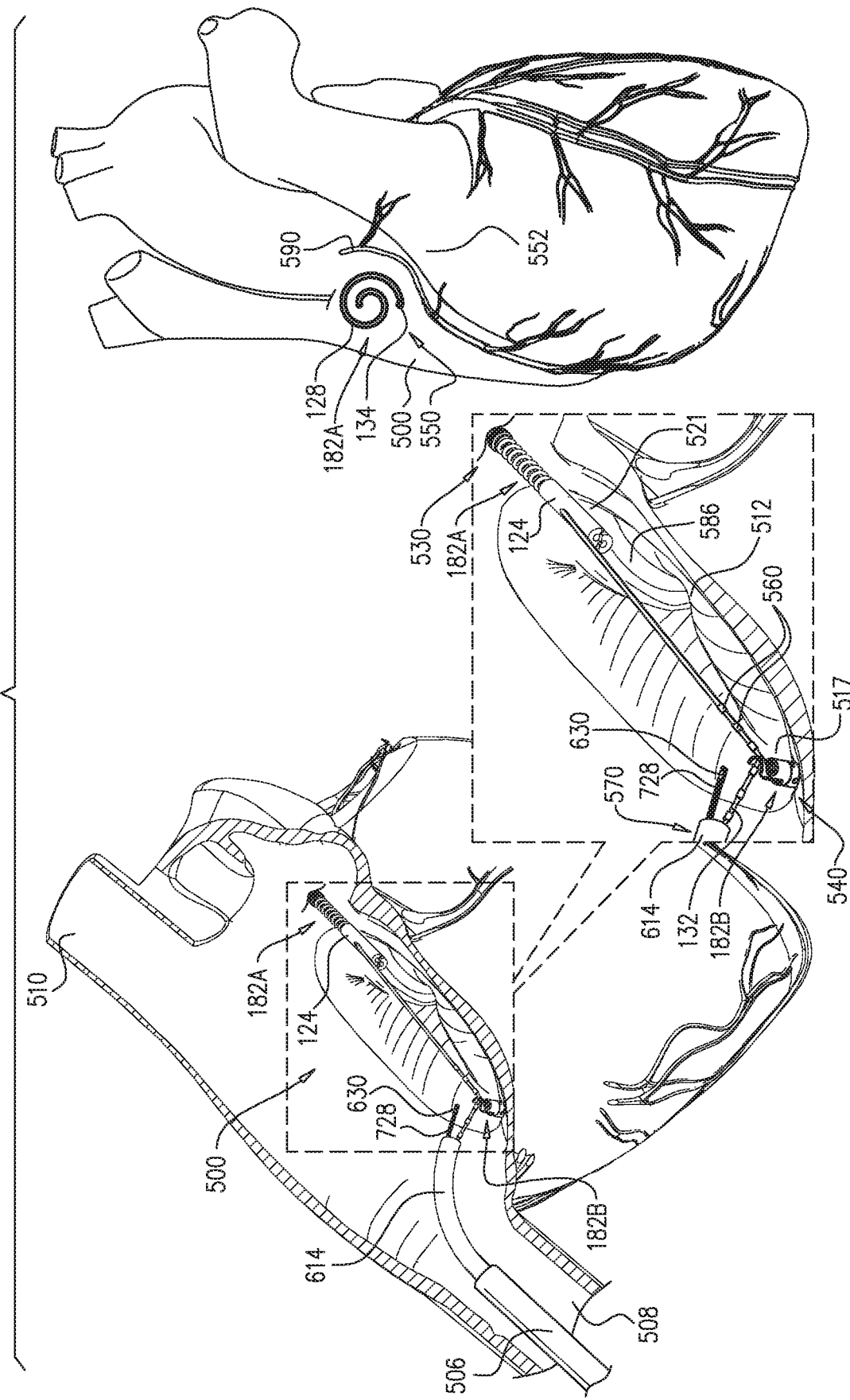
Figure 15C:
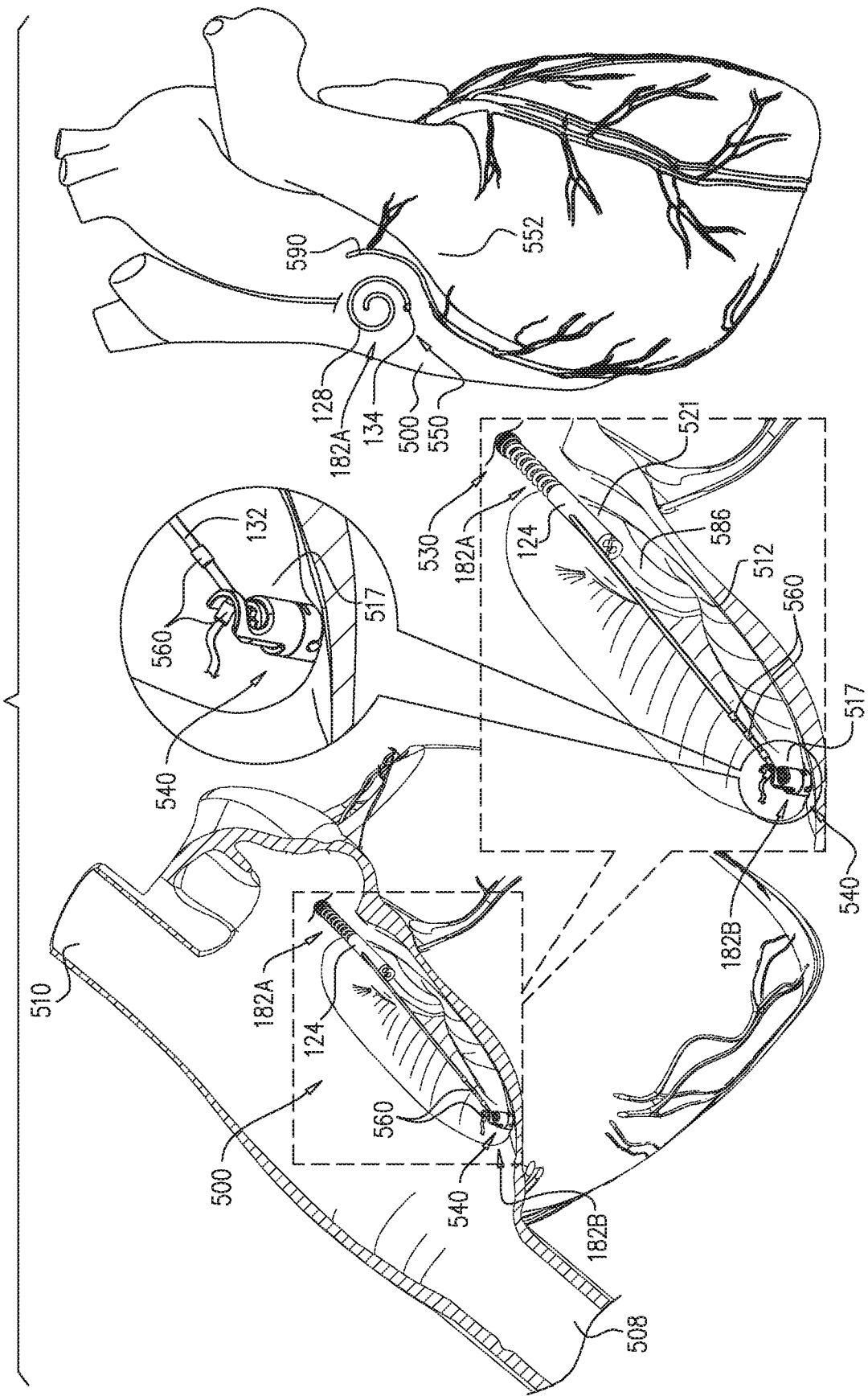

Reference is now made to FIGS. 15A-C, which are schematic illustrations of another method for deploying tissue anchor system 180 or tissue anchor system 248 for repairing tricuspid valve 504, in accordance with an application of the present invention. In the particular method shown in these figures, first tissue anchor 182A of tissue anchor system 180 comprises first tissue anchor 120, and second tissue anchor 182B of tissue anchor system 180 comprises helical tissue-coupling element 184, described hereinabove with reference to FIG. 4A. For some applications, second tissue anchor 182B comprises tissue anchor 724, described hereinbelow with reference to FIGS. 17A-18B. The method may also be used to deploy other tissue anchors described herein, including tissue anchor 200 or 300 of tissue anchor system 248 as the first tissue anchor, mutatis mutandis. Tissue anchor system 180 or tissue anchor system 248 further comprises deployment tool 30, for deploying first tissue anchor 182A, and, typically, a second anchor delivery tool 570 for deploying second tissue anchor 182B. For some applications, second anchor delivery tool 570 comprises a torque-delivery tool 720, described hereinbelow with reference to FIGS. 17A-18B. Tissue anchor system 180 or tissue anchor system 248 allows first and second tissue anchors 182A and 182B to be delivered separately and connected afterwards in situ. This simplifies the procedure for the operator, and allows an approach from two or more different blood vessels such as transfemoral, transjugular, transradial or transapical approaches, which may provide simpler access to the anchoring point.

First tissue anchor 182A is implanted as described hereinabove with reference to FIGS. 13A-D or FIGS. 13A-D, as appropriate. As mentioned above, first implantation site 530 is shown as circumferential middle 521 of anterior leaflet 586; alternative first implantation sites 530 are set forth hereinbelow in Table 2. As mentioned with reference to FIG. 13C, after first tissue anchor 182A has been implanted at first implantation site 530, deployment tool 30 is removed from the subject's body, typically leaving catheter 506 in situ.

As shown in FIG. 15A, second tissue anchor 182B is implanted in the subject at second implantation site 540. For example, second tissue anchor 182B may comprise helical tissue-coupling element 184, described hereinabove with reference to FIG. 4A, and second implantation site 540 may be within 1 cm of a site on the annulus that circumferentially corresponds to a septoposterior commissure 517; alternative second implantation sites 540 are set forth hereinbelow in Table 2. For some applications, the one or more tethers 132 comprise a single tether 132. For some applications, tether 132 defines a plurality of securement protrusions 560 spaced at intervals along tether 132, which protrusions serve as the friction-enhancing features. For some applications, as shown, protrusions 560 comprise respective cylinders on tether 132.

For some applications, outside the subject's body, the surgeon threads a free end of tether 132 through a lateral opening 582 of an outer tether-securing element 580 of second tissue anchor 182B, and then through a lumen of a delivery tube 614. Tether 132 thus connects first and second tissue anchors 182A and 182B.

For some applications, as shown in FIG. 15A, second tissue anchor 182B is implanted at second implantation site 540 using a torque-delivery cable 728 of torque-delivery tool 720, described hereinbelow with reference to FIGS. 17A-18B. Second tissue anchor 182B and torque-delivery cable 728 are introduced over tether 132 and through delivery tube 614, which itself is advanced through catheter 506. A tether-locking mechanism of second tissue anchor 182B is introduced in an unlocked state in which sliding of tether 132 through a lateral opening 782 of second tissue anchor 182B is not inhibited. Second tissue anchor 182B is implanted at second implantation site 540 by rotating torque-delivery cable 728 (including a torque-delivery head 730).

The size of the tricuspid valve orifice is reduced by tensioning tether 132, so as to reduce regurgitation. Such tensioning may be performed by proximally pulling on the free end of tether 132, such that a portion of tether 132 is pulled through lateral opening 582 of second tissue anchor 182B. This tension can be applied remotely, i.e., via catheter 506. Application of such tension facilitates repair of an atrioventricular valve of the subject, such as tricuspid valve 504.

As shown in FIG. 15B, once the tension has been applied, torque-delivery cable 728 (including torque-delivery head 730) is decoupled from second tissue anchor 182B, such as by removing a locking wire. As a result, a spring 770 expands and presses tether 132 against an outer tether-securing element 780, both of which are described hereinbelow with reference to FIGS. 17A-18B. This pressing transitions the tether-locking mechanism to a locked state, in which state the sliding of tether 132 through the second tissue anchor 182B is inhibited. Such locking maintains the distance and tension between second tissue anchor 182B and first tissue anchor 182B.

As shown in FIG. 15C, after tether 132 has been tensioned, an excess portion of tether 132 remains free in the right atrium. It is generally undesirable to leave this excess portion free to move around in the atrium. For some applications, the excess portion of tether 132 is cut and removed from the atrium, using a cutting tool, such as thoracoscopic scissors, as known in the art. Further alternatively, for some applications, the excess portion is secured in a desired disposition in the vasculature of the right atrium, such as in inferior vena cava 508, superior vena cava 510, or a coronary sinus.

The following Table 2 sets forth exemplary combinations of (a) anatomical markers for first implantation site 530, (b) anatomical markers for second implantation site 540, and (c) external exit sites 550. These sites are listed by way of example and not limitation; the surgeon typically selects the exact sites based on the subject's individual needs and anatomy. Each of first and second implantation sites 530 and 540 is located within 1 cm of the site on the annulus that circumferentially corresponds to the respective anatomical marker (i.e., is at the same angular location or "o'clock" as the respective anatomical marker). The direction of the 1 cm from the site on the annulus may be either circumferentially (i.e., clockwise or counterclockwise) around the annulus, up the wall of the right atrium above the annulus, or a combination of circumferentially around the annulus and up the wall of the atrium. For example, as shown in FIG. 15C, septoposterior commissure 517 is near, but not on, the annulus, and second tissue anchor 182B is shown implanted at second implantation site 540, which is at the site on the annulus that circumferentially corresponds to this commissure. Second implantation site 540 could also be up to 1 cm clockwise or counterclockwise around the annulus from this site on the annulus, up to 1 cm up the wall of the atrium, or a combination of these two directions.

Typically, the surgeon uses the anatomical markers to find the exact locations of first and second implantation sites 530 and 540, which are within 1 cm of the anatomical markers, as described above. For example, the commissures are easily detectable using imaging, and thus represent good anatomical markers. However, the commissures are not appropriate for implantation (because they are too delicate), so, in this example, second tissue anchor 182B is implanted on the annulus or up the wall of the atrium, within 1 cm from the commissure.

TABLE 2

| First implantation site 530 anatomical marker | Second implantation site 540 anatomical marker | External exit site 550 |
|---|---|---|
| Circumferential middle 521 of anterior leaflet 586 | Septoposterior commissure 517 | Right atrium 500 |
| Anteroposterior commissure 512 | Septoposterior commissure 517 | Right atrium 500 |
| Circumferential middle 521 of anterior leaflet 586 | Septoposterior commissure 517 | Right ventricle 552 |
| Anteroposterior commissure 512 | Septoposterior commissure 517 | Right ventricle 552 |

Figure 16:
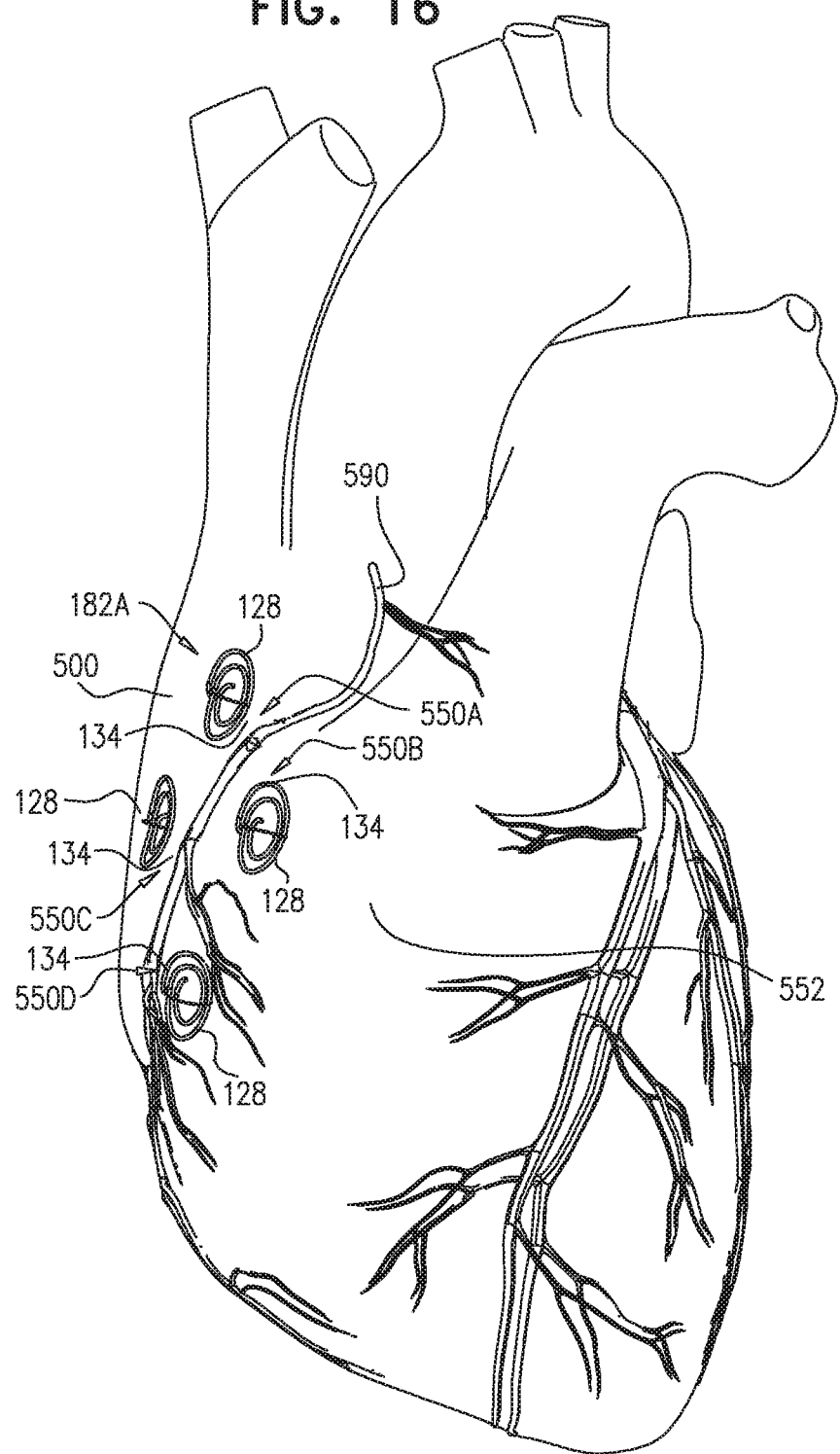
FIG. 16 is a schematic illustration of several external exit sites on a heart, in accordance with respective applications of the present invention.

Reference is now made to FIG. 16, which is a schematic illustration of several external exit sites 550, in accordance with respective applications of the present invention. External exit sites 550 are typically within 10 mm, such as 5 mm, of RCA 590 or branches from the RCA such as the posterior descending artery (PDA) or veins of the right ventricle. External exit sites 550A and 550C are on right atrium 500, and external exit sites 550B and 550D are on right ventricle 552.

For some applications, both first and second tissue anchors 182A and 182B comprise respective tissue anchors 20 (tissue anchors 120, described hereinabove with reference to FIGS. 1A-3B; tissue anchor 200, described hereinabove with reference to FIGS. 5A-7B; tissue anchor 258, described hereinabove with reference to FIGS. 8A-B; tissue anchor 220, described hereinabove with reference to FIGS. 10A-B; tissue anchor 300, described hereinabove with reference to FIGS. 9A-G; tissue anchor 290, described hereinabove with reference to FIG. 9H; tissue anchor 320, described hereinabove with reference to FIGS. 11A-C; tissue anchor 420, described hereinabove with reference to FIGS. 12A-C; or a combination of two different ones of these tissue anchors). For some applications, first tissue anchor 182A is implanted at an implantation site located with 1 cm of the site on the annulus that circumferentially corresponds to an anatomical marker between circumferential middle 521 of anterior leaflet 586 and anteroposterior commissure 512, inclusive. Alternatively or additionally, for some applications, second tissue anchor 182B is implanted at an implantation site located with 1 cm of the site on the annulus that circumferentially corresponds to an anatomical marker between a circumferential middle of a posterior leaflet and septoposterior commissure 517, inclusive.

Further alternatively or additionally, for some applications, second tissue anchor 182B is implanted at an implantation site located above the triangle of Koch, through the septal muscle into the left atrium above the level of the mitral valve. The off-centeredness of tissue anchors 120, 200, 220, 300, 320, and 420 allows the tissue-coupling element to be rotated during implantation so as to avoid contact with the mitral valve if the anchor enters the left atrium lower than expected. For some of these applications, first tissue anchor 182A comprises a stent, such as described hereinabove, which may be connected to second tissue anchor 182B by one or more tethers, at least one of which passes through a pulley, such as described in PCT Publication WO 2015/063580, which is incorporated herein by reference. Alternatively, the anchors are implanted and coupled to one another under tension using the techniques described hereinbelow with reference to FIG. 15B, mutatis mutandis.

For some applications, the head of second tissue anchor 182B comprises proximal anchor head 752, described hereinbelow with reference to FIGS. 17A-18B (and second tissue anchor 182B comprises one of tissue-coupling elements described hereinabove, as mentioned above).

FIGS. 17A-F are schematic illustrations of a tissue-anchor system 710 in an unlocked state, in accordance with an application of the present invention. FIGS. 18A-B are schematic illustrations of tissue-anchor system 710 in a locked state, in accordance with an application of the present invention. Tissue-anchor system 710 comprises torque-delivery tool 720, tether 132, and tissue anchor 724. Torque-delivery tool 720 is configured to implant tissue anchor 724 in cardiac tissue, and to thereafter lock tether 132 to tissue anchor 724, such that sliding of tether 132 with respect to tissue anchor 724 is inhibited. Typically, tether 132 is tensioned after tissue anchor 724 has been implanted in the cardiac tissue, and after the tether has been tensioned, tether 132 is locked to tissue anchor 724.

Torque-delivery tool 720 comprises (a) torque-delivery cable 728, which comprises distal torque-delivery head 730, (b) a distal coupling element 732 that is fixed to a distal end 734 of torque-delivery head 730, and (c) a distal spring depressor 736.

Tissue anchor 724 comprises (a) a tissue-coupling element 750, and (b) a proximal anchor head 752, which is attached to a proximal portion 754 of tissue-coupling element 750. For some applications, tissue-coupling element 750 comprises a helical tissue-coupling element, which punctures and screws into cardiac tissue. For some applications, tissue-coupling element 750 implements features of one or more of the tissue-coupling elements described in PCT Publication WO 2014/108903, which is incorporated herein by reference.

Anchor head 752 comprises an axially-stationary shaft 756 and a tether-locking mechanism 768. Axially-stationary shaft 756 (which can best be seen in FIGS. 17D-F) has (a) a distal portion 758 that is axially fixed with respect to proximal portion 754 of tissue-coupling element 750, and (b) a proximal end 760 that comprises a proximal coupling element 762. Distal and proximal coupling elements 732 and 762 are shaped so as to define corresponding interlocking surfaces, which facilitate coupling of torque-delivery head 730 to axially-stationary shaft 756.

Tether-locking mechanism 768 comprises:
  spring 770 (which can best be seen in FIG. 17D) (for clarity of illustration of other elements, spring 770 is not shown in FIGS. 17E-F; the spring is actually present); and
  outer tether-securing element 780, which (a) is shaped so as to define lateral opening 782 through which tether 132 is disposed, and (b) at least partially radially surrounds axially-stationary shaft 756 and spring 770 (and hammer cap 800, if provided, as described below). For some applications, as shown in the figures, outer tether-securing element 780 is shaped as a partial cylinder.

Figure 17A:
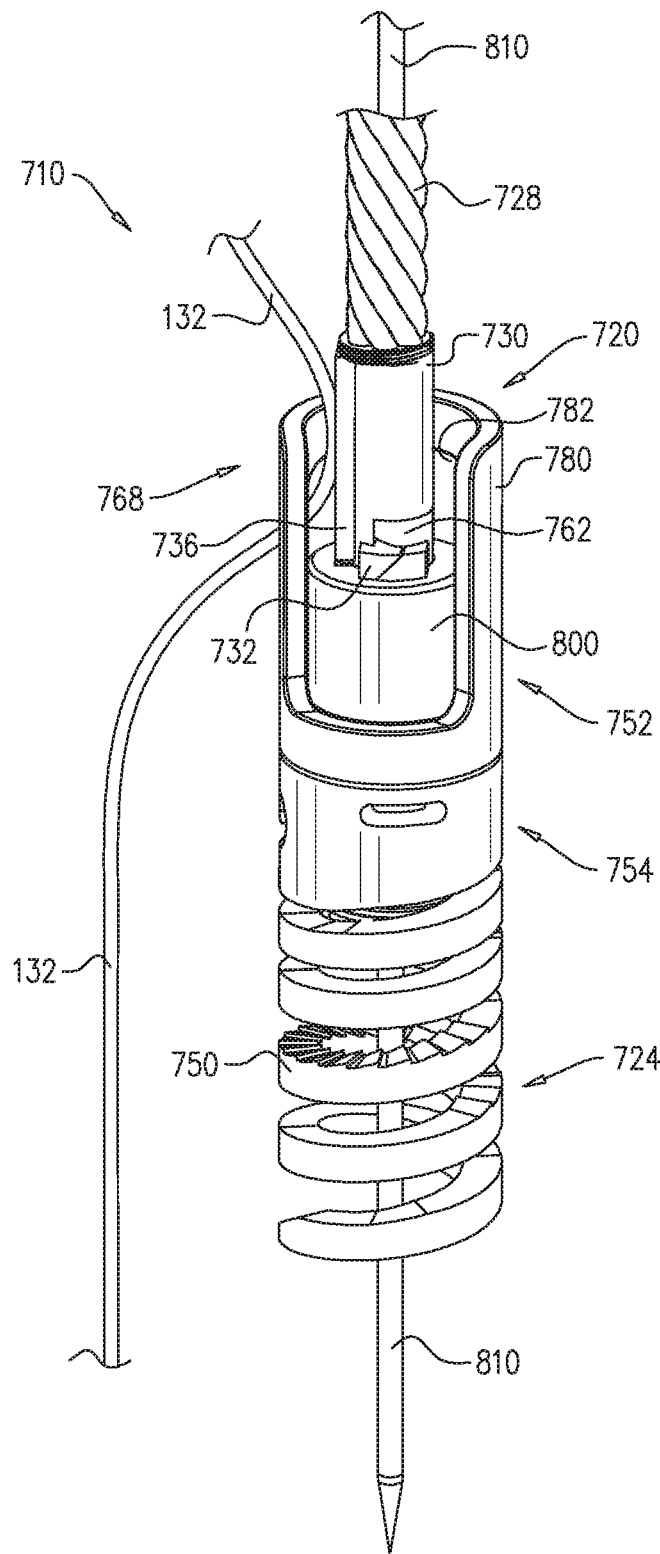
Figure 17B:
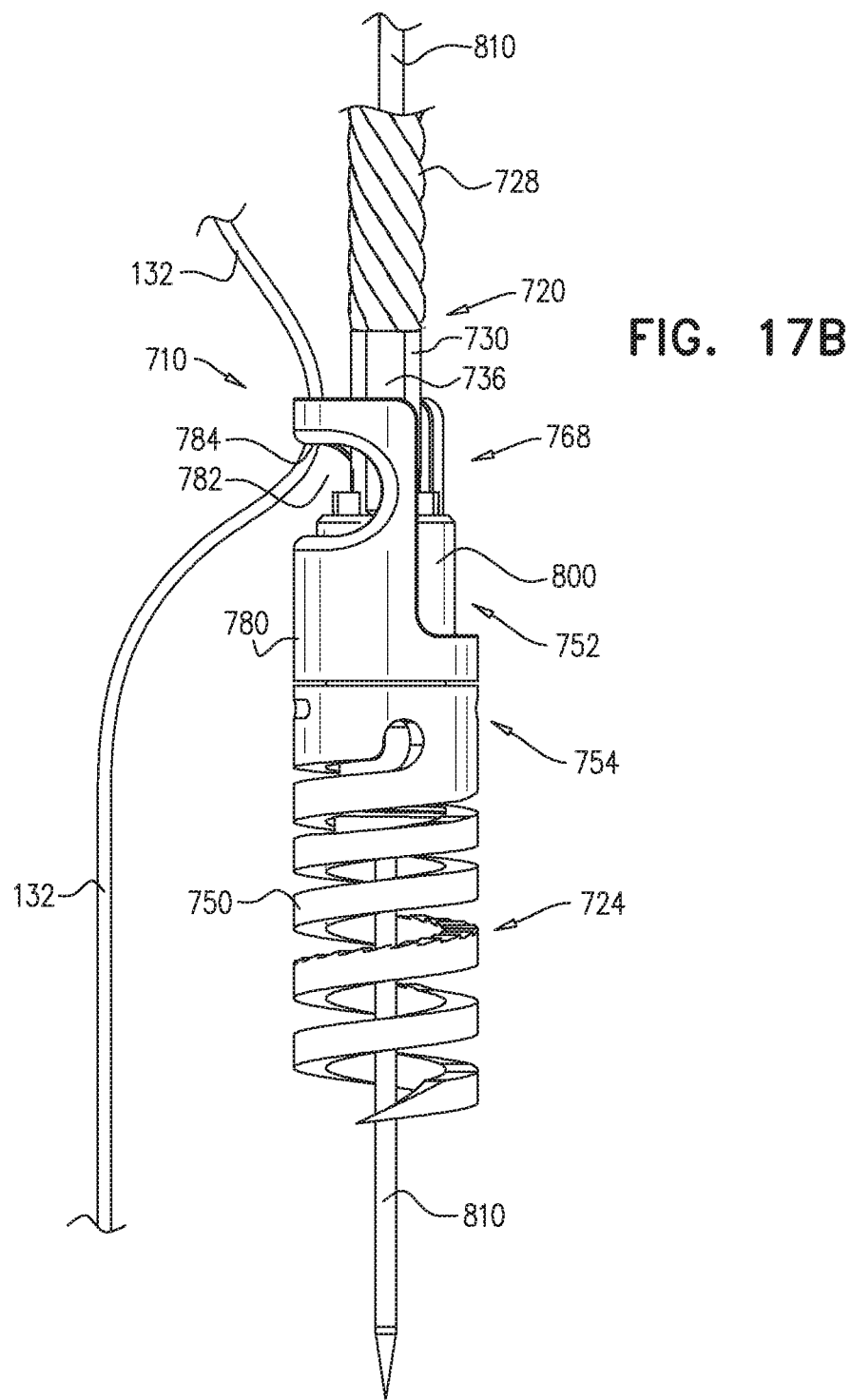
Figure 17C:
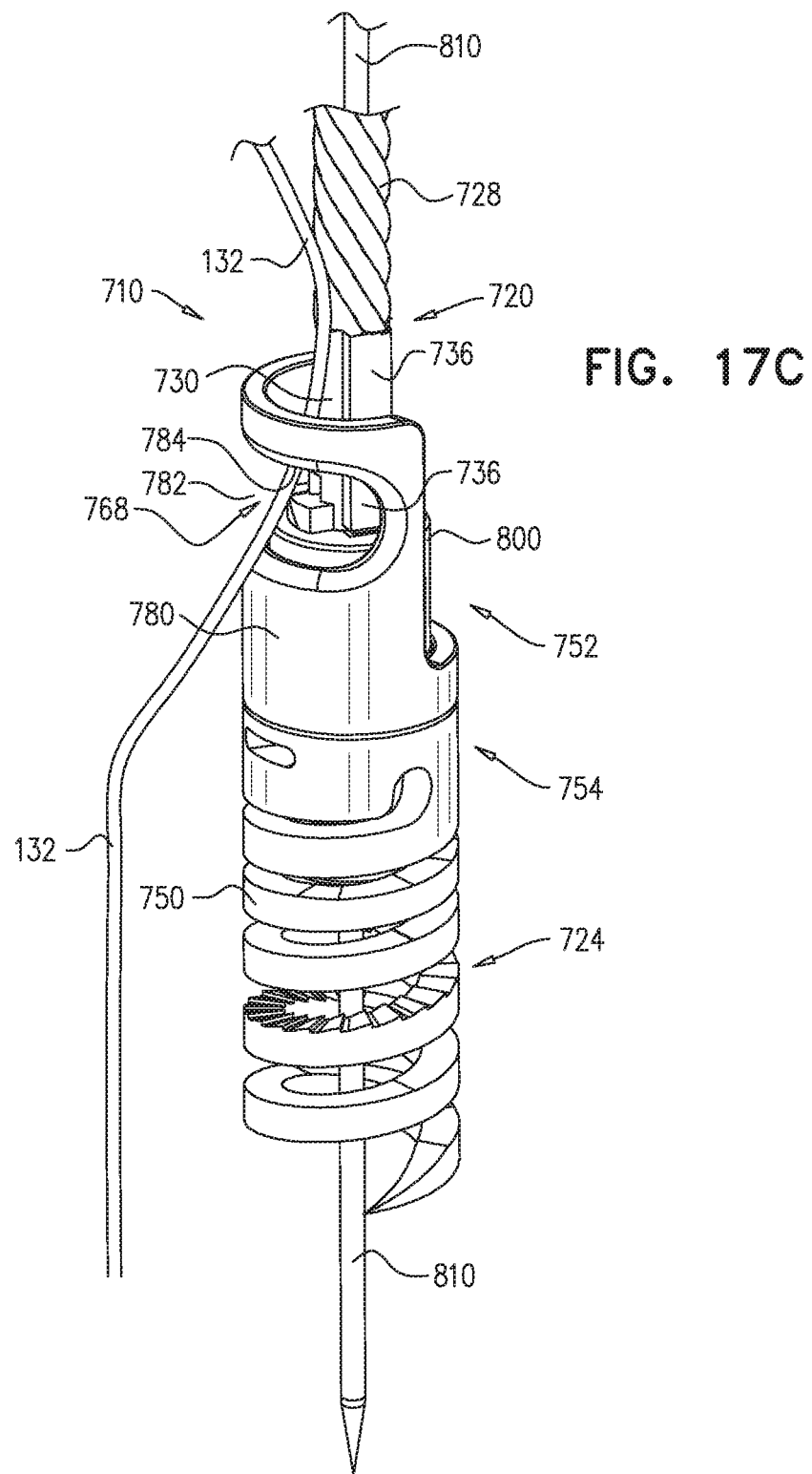
Figure 17D:
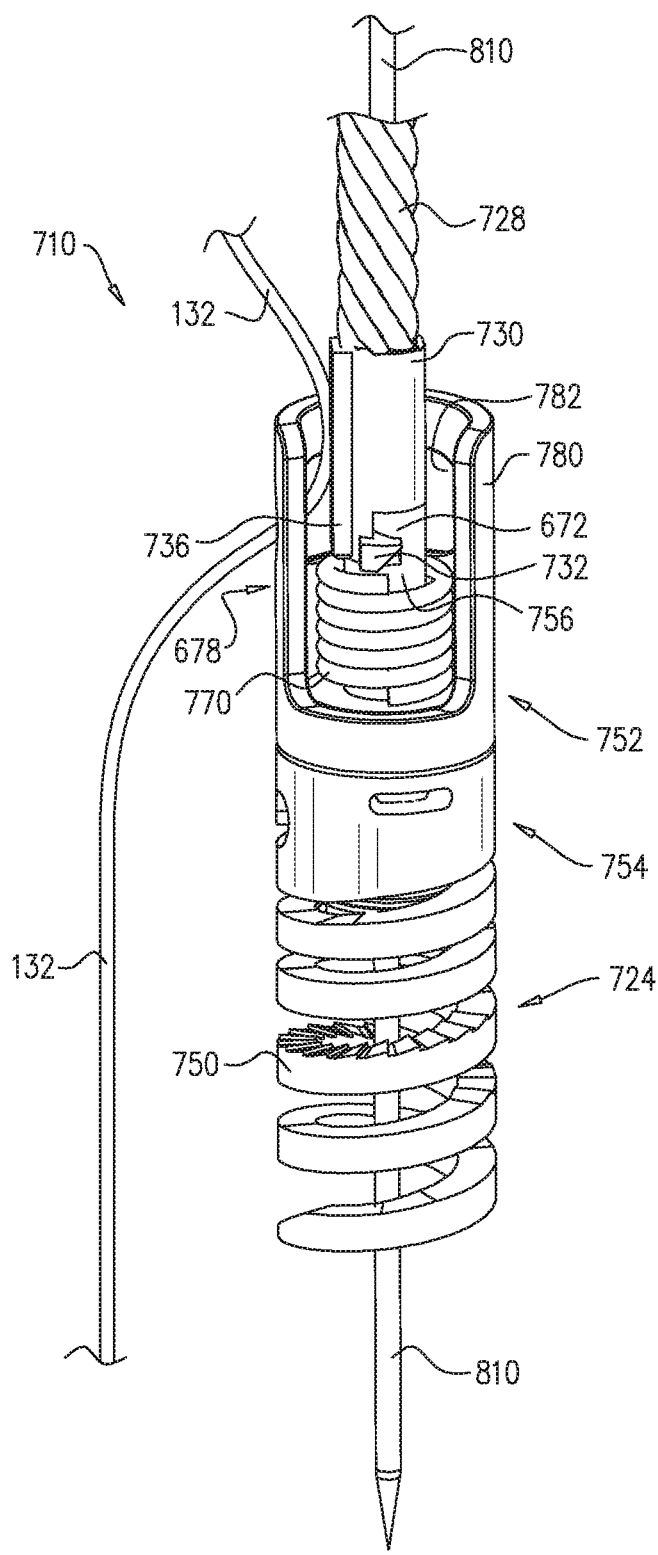
Figure 17E:
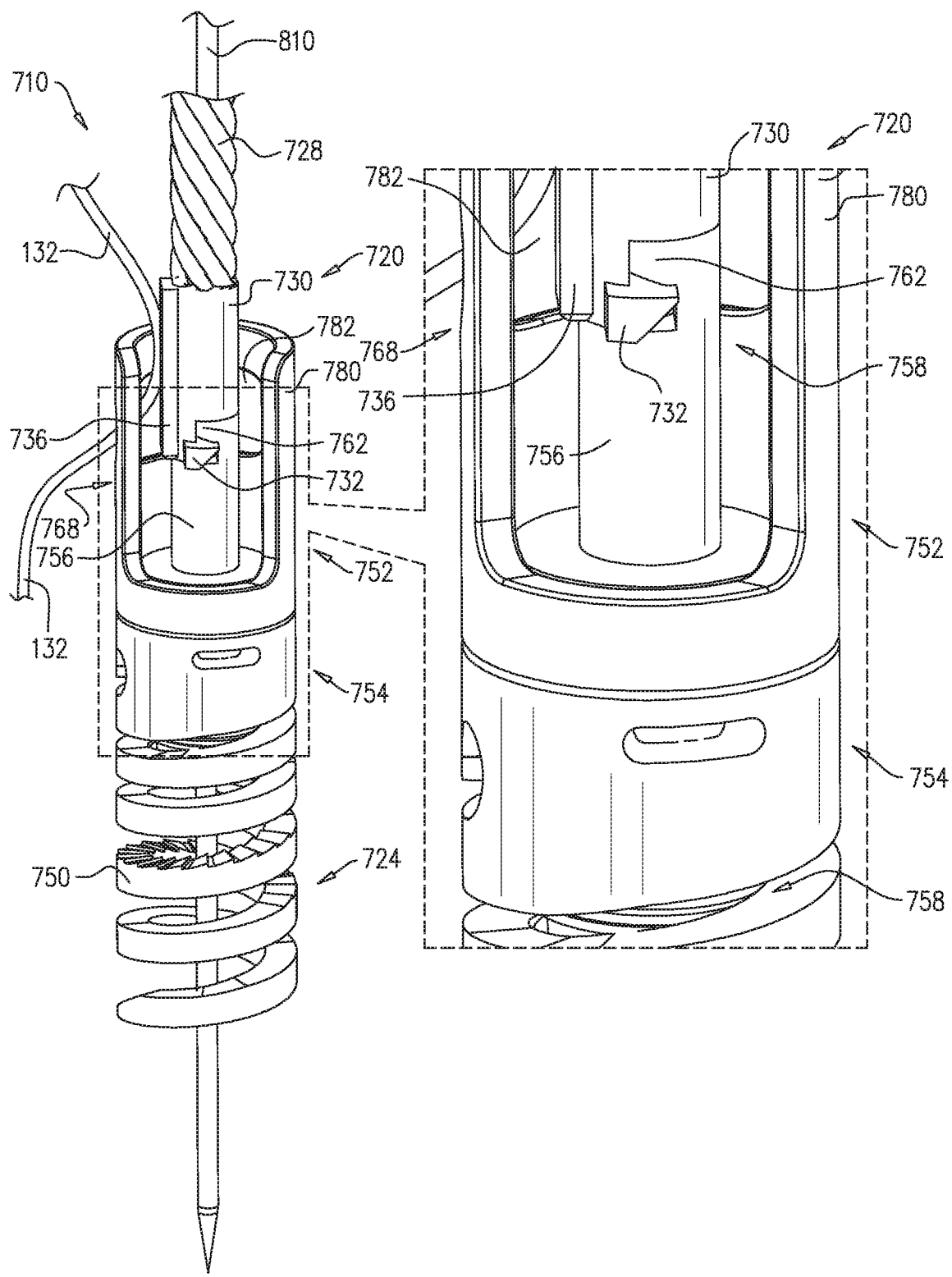
Figure 18A:
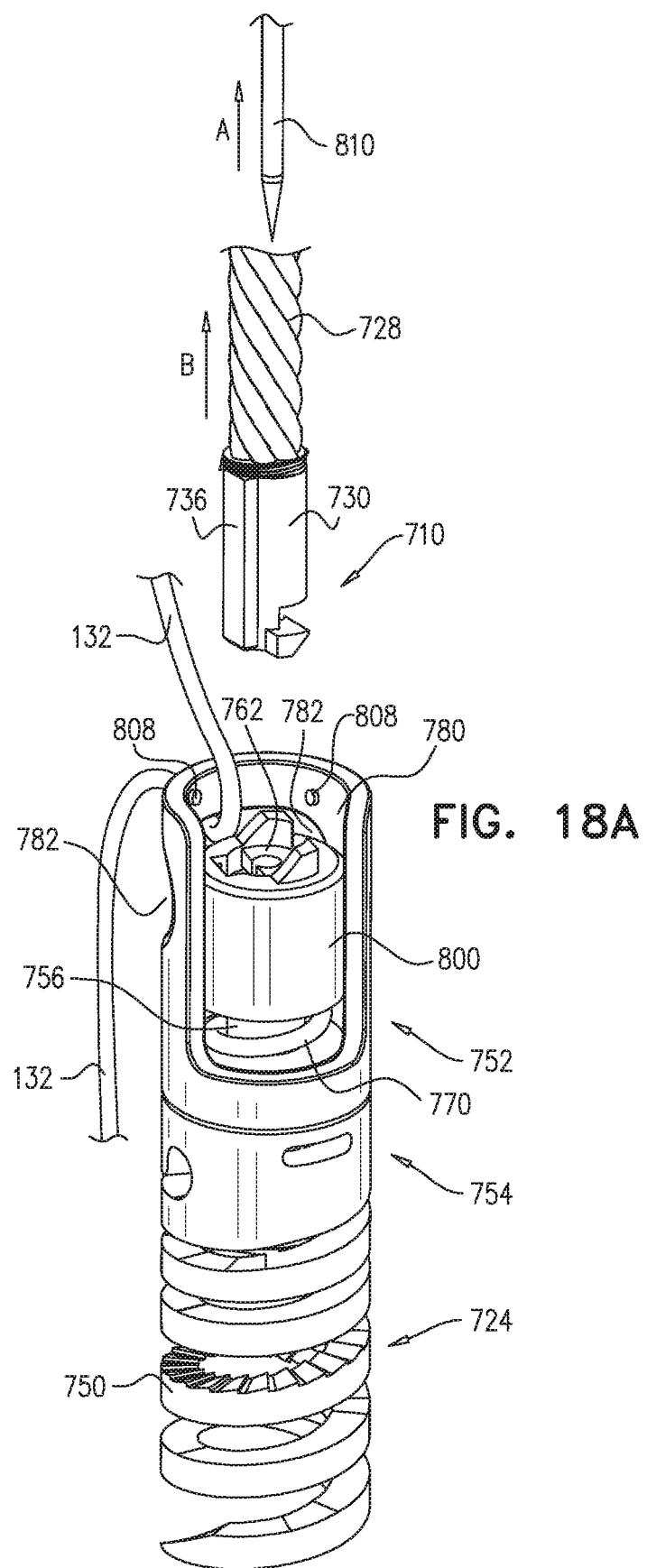
FIGS. 18A-B are schematic illustrations of the tissue-anchor system of FIGS. 17A-F in a locked state, in accordance with an application of the present invention.
Figure 18B:
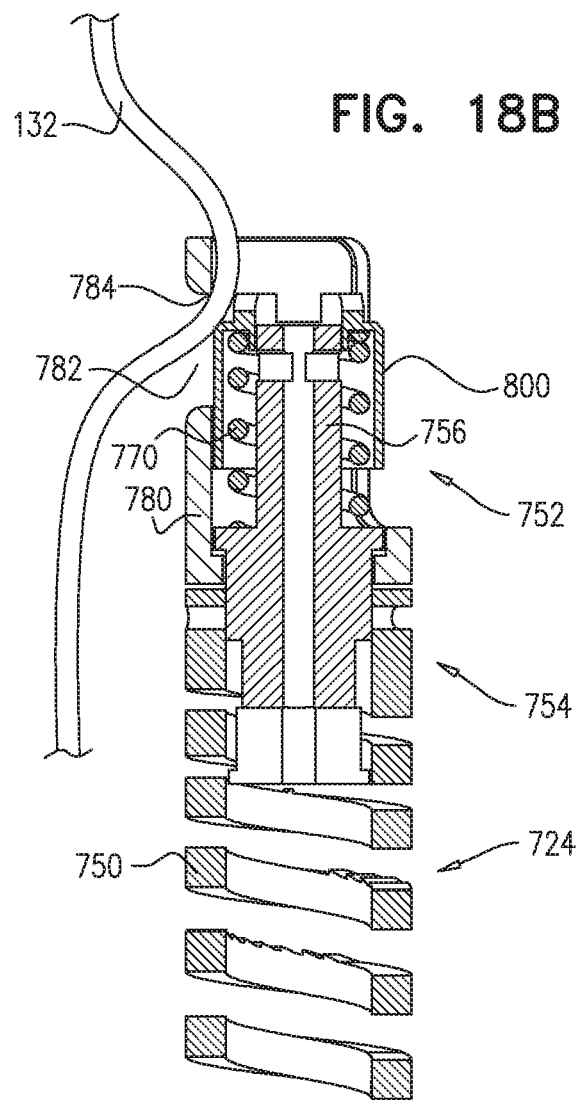

For some applications, at least a portion of spring 770 radially surrounds axially-stationary shaft 756, such as shown in FIG. 17D. For some applications, at least a portion of spring 770 is helical, such as shown in FIGS. 17D and 18A-B (e.g., the entire spring is helical, such as shown in FIGS. 17D and 18A-B), while for other applications, spring 770 is not helical.

Tissue-anchor system 710 is configured to assume:
  an unlocked state, as shown in FIGS. 17A-F, in which (a) distal and proximal coupling elements 732 and 762 are interlockedly coupled with one other, and (b) distal spring depressor 736 restrains spring 770 in an axially-compressed state, in which state spring 770 does not inhibit sliding of tether 132 through lateral opening 782, and
  a locked state, as shown in FIGS. 18A-B, in which (a) distal and proximal coupling elements 732 and 762 are not coupled with one another, (b) distal spring depressor 736 does not restrain spring 770 in the axially-compressed state, and (c) spring 770 is in an axially-expanded state, in which state spring 770 inhibits the sliding of tether 132 through lateral opening 782 by pressing tether 132 against outer tether-securing element 780, such as against a perimeter 784 of lateral opening 782, and/or an inner surface of outer tether-securing element 780.

When tissue-anchor system 710 is in the unlocked state, tether-locking mechanism 768 is also in an unlocked state, in which state spring 770 does not inhibit sliding of tether 132 through lateral opening 782. When tissue-anchor system 710 is in the locked state, tether-locking mechanism 768 is also in a locked state, in which state spring 770 inhibits the sliding of tether 132 through lateral opening 782 by pressing tether 132 against outer tether-securing element 780, such as against perimeter 784 of lateral opening 782, and/or an inner surface of outer tether-securing element 780.

Tissue-anchor system 710 is advanced into the heart in the unlocked state. Tissue anchor 724 is implanted in cardiac tissue, using torque-delivery cable 728 while tissue-anchor system 710 is in the unlocked state. After tissue anchor 724 is implanted, tension is applied to tether 132. Thereafter, torque-delivery cable 728 (including torque-delivery head 730) is decoupled from axially-stationary shaft 756 of tissue anchor 724, thereby allowing spring 770 to expand and press tether 132 against outer tether-securing element 780. This pressing locks tether 132 with respect to tissue anchor 724, and maintains the distance and tension between tissue anchor 724 and one or more other implanted tissue anchors, such as described hereinabove with reference to FIGS. 15A-C. Alternatively, tissue-anchor system 710 is used to implant tissue anchor 24 in non-cardiac tissue of a subject, in which case tissue-anchor system 10 is advanced into another location in the subject's body.

Torque-delivery cable 728 (including torque-delivery head 730) thus serves two functions:
  implanting tissue anchor 724 in cardiac tissue, by applying a rotational force to tissue anchor 724; and
  maintaining tissue-anchor system 710 in the unlocked state, in which state tether 132 can slide with respect to tissue anchor 724, allowing tension to be applied to the tether (and adjusted as necessary).

Similarly, decoupling of torque-delivery cable 728 (including torque-delivery head 730) from axially-stationary shaft 756 of anchor head 752 of tissue anchor 724 simultaneously (1) releases tissue anchor 724 and (2) transitions tissue-anchor system to the locked state.

For some applications, as can be seen in FIGS. 17A-C and FIGS. 18A-B, anchor head 752 further comprises a hammer cap 800, which is fixed to spring 770, and covers at least a portion 802 of spring 770, including a proximal end 804 of spring 770. (For clarity of illustration of other elements, hammer cap 800 is not shown in FIGS. 17D-F; the hammer cap is optionally present.) When tissue-anchor system 710 is in the locked state, spring 770 presses tether 132 against outer tether-securing element 780 by pressing hammer cap 800 against outer tether-securing element 780, such as perimeter 784 of lateral opening 782, and/or an inner surface of outer tether-securing element 780. Hammer cap 800 may prevent entanglement of tether 132 with spring 770. In addition, providing hammer cap 800 may obviate the need to weld a distal end of spring 770 to anchor head 752, because the hammer cap surrounds at least a portion of the spring and thereby couples the spring to the anchor head. For some applications, tether 132 prevents hammer cap 800 from proximally exiting outer tether-securing element 780. Alternatively or additionally, for some applications, one or more small pins 808 (shown in FIG. 18A) are provided that extend radially inward from an inner surface of outer tether-securing element 780; the pins prevent the hammer cap from proximally exiting the outer tether-securing element.

For some applications, tissue-anchor system 710 further comprises a locking wire 810. Torque-delivery cable 728 (including torque-delivery head 730), distal coupling element 732, proximal coupling element 762, and axially-stationary shaft 756 are shaped so as define respective channels 772, 774, 776, and 778 therethrough, which are radially aligned with each other and coaxial with tissue anchor 724. When tissue-anchor system 710 is in the unlocked state, a portion of locking wire 810 is disposed in the channels, thereby preventing decoupling of distal and proximal coupling elements 732 and 762 from one another. Proximal withdrawal and removal of the portion of locking wire 810 from the channels allows the decoupling of distal and proximal coupling elements 732 and 762 from one another.

For some applications, locking wire 810 is shaped so as to define a sharp distal tip 822. For these applications, tissue-coupling element 750 typically is helical, and locking wire 810 is initially removably positioned within a channel defined by the helix. As tissue-coupling element 750 is screwed into tissue, locking wire 810 penetrates and advances into the tissue along with the anchor to a certain depth in the tissue. For some applications, when the shaft penetrates to the certain depth, the locking wire is withdrawn slightly. Typically, after tissue-coupling element 750 has been fully implanted, locking wire 810 is withdrawn entirely from the tissue, and removed from the subject's body. Optionally, sharp distal tip 822 of locking wire 810 is inserted into the tissue slightly, even before insertion of tissue-coupling element 750, in order to inhibit sliding of the tissue-coupling element on the surface of the tissue before commencement of insertion of the tissue-coupling element into the tissue.

For some applications, outer tether-securing element 780 is rotatable with respect to tissue-coupling element 750 and axially-stationary shaft 756, in order to provide rotational freedom of movement to tether 132 after implantation of tissue anchor 724, particularly during tensioning of tether 132. This rotational freedom of movement avoids twisting of the tether around the anchor head, and facilitates ideal orientation of the tether with another tissue anchor.

For some applications, outer tether-securing element 780 has an outer diameter of at least 1 mm, no more than 6 mm, and/or between 1 and 6 mm. For some applications, tissue anchor 724 has an outer diameter of at least 2 mm, no more than 8 mm, and/or between 2 and 8 mm.

Although the techniques described herein have been described as being used to remodel the tricuspid valve, these techniques may also be used to remodel the mitral valve, mutatis mutandis. In addition, the tissue anchors described herein may be implanted on the surface of any wall of the heart or other organ where tension is to be applied, and rotationally repositioned to avoid obstructions of anatomic structures such as blood vessels or conduction systems, or pre-existing implants.

As used in the present application, including in the claims, when a range of values is specified using the word "between," the range includes the endpoint values.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Pat. No. 8,475,525 to Maisano et al.;
U.S. Pat. No. 8,961,596 to Maisano et al.;
U.S. Pat. No. 8,961,594 to Maisano et al.;
International Application PCT/IL2011/000064, filed Jan. 20, 2011, which published as PCT Publication WO 2011/089601, and U.S. application Ser. No. 13/574,088 in the national stage thereof, which published as US Patent Application Publication 2013/0046380;
U.S. application Ser. No. 13/553,081, filed Jul. 19, 2012, which published as US Patent Application Publication 2013/0018459;
International Application PCT/IL2012/000282, filed Jul. 19, 2012, which published as PCT Publication WO 2013/011502;
U.S. Provisional Application 61/750,427, filed Jan. 9, 2013;
U.S. Provisional Application 61/783,224, filed Mar. 14, 2013;
International Application PCT/IL2013/050470, filed May 30, 2013, which published as PCT Publication WO 2013/179295;
U.S. Provisional Application 61/897,491, filed Oct. 30, 2013;
U.S. Provisional Application 61/897,509, filed Oct. 30, 2013;
U.S. application Ser. No. 14/143,355, filed Dec. 30, 2013, which published as US Patent Application Publication 2014/0114390;
International Application PCT/IL2014/050027, filed Jan. 9, 2014, which published as PCT Publication WO 2014/108903;
International Application PCT/IL2014/050233, filed Mar. 9, 2014, which published as PCT Publication WO 2014/141239;
U.S. Provisional Application 62/014,397, filed Jun. 19, 2014;
International Application PCT/IB2014/002351, filed Oct. 28, 2014, which published as PCT Publication WO 2015/063580;
U.S. application Ser. No. 14/525,668, filed Oct. 28, 2014, which published as US Patent Application Publication 2015/0119936;
U.S. Provisional Application 62/086,269, filed Dec. 2, 2014;
U.S. Provisional Application 62/131,636, filed Mar. 11, 2015;
U.S. Provisional Application 62/167,660, filed May 28, 2015; and
International Application PCT/IB2015/001196, filed Jun. 14, 2015, which published as PCT Publication WO 2015/193728.

Patents and patent application publications incorporated by reference in the present patent application are to be considered an integral part of the application except that to the extent any terms are defined in these incorporated patents and patent application publications in a manner that conflicts with the definitions made explicitly or implicitly in the present specification, only the definitions in the present specification should be considered. In particular, the definition of "spiral" provided in U.S. Provisional Application 62/086,269, filed Dec. 2, 2014, and U.S. Provisional Application 62/167,660, filed May 28, 2015 should not be considered.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   introducing, during a transcatheter procedure, a tissue anchor into a cardiac chamber of a heart of a subject, while a tissue-coupling element of the tissue anchor is constrained by a deployment tool;
   delivering the tissue-coupling element distally through a wall of the heart;
   at least partially releasing the tissue anchor from the deployment tool such that the tissue-coupling element is unconstrained by the deployment tool;
   after delivering the tissue-coupling element through the wall of the heart and at least partially releasing the tissue anchor from the deployment tool:
      ascertaining whether the tissue-coupling element overlies a coronary blood vessel; and
      if the tissue-coupling element overlies the coronary blood vessel, rotating the tissue anchor until the tissue-coupling element no longer overlies the coronary blood vessel; and
      thereafter, proximally pulling the tissue-coupling element by applying tension to the tissue anchor.

2. The method according to claim 1, wherein applying the tension facilitates repair of an atrioventricular valve of the subject.

3. The method according to claim 1,
   wherein the tissue anchor is a first tissue anchor, and wherein the method further comprises implanting a second tissue anchor in the subject, which second tissue anchor is separate and distinct from the first tissue anchor, and
   wherein applying the tension to the tissue anchor comprises applying the tension to one or more tethers that couple the first tissue anchor to the second tissue anchor.

4. The method according to claim 1, wherein delivering the tissue-coupling element through the wall of the heart comprises advancing a sharp distal piercing tip of the deployment tool through the wall while the tissue-coupling element is disposed within the deployment tool.

5. The method according to claim 1, wherein ascertaining whether the tissue-coupling element overlies the coronary blood vessel comprises ascertaining whether the tissue-coupling element overlies a right coronary artery.

6. The method according to claim 1, wherein the tissue anchor comprises a shaft and the tissue-coupling element is supported at a distal end of the shaft, and wherein rotating the tissue anchor if the tissue-coupling element overlies the coronary blood vessel comprises rotating the shaft.

7. The method according to claim 6, wherein the tissue-coupling element comprises a wire.

* * * * *